(12) United States Patent
Papaioannou et al.

(10) Patent No.: US 11,370,803 B2
(45) Date of Patent: *Jun. 28, 2022

(54) HETEROARYL PLASMA KALLIKREIN INHIBITORS

(71) Applicant: Takeda Pharmaceutical Company Limited, Osaka (JP)

(72) Inventors: Nikolaos Papaioannou, Newton, MA (US); Jeremy Mark Travins, Southborough, MA (US); Sarah Jocelyn Fink, Arlington, MA (US); John Mark Ellard, Buntingford (GB); Alastair Rae, Saffron Walden (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/024,189

(22) Filed: Sep. 17, 2020

(65) Prior Publication Data

US 2021/0079022 A1 Mar. 18, 2021

Related U.S. Application Data

(60) Provisional application No. 62/902,333, filed on Sep. 18, 2019.

(51) Int. Cl.
*C07D 519/00* (2006.01)
(52) U.S. Cl.
CPC .................. *C07D 519/00* (2013.01)
(58) Field of Classification Search
CPC .................. C07D 471/04; C07D 519/00
USPC ...................................................... 514/300
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,212,162 A | 5/1993 | Missel et al. | |
| 5,403,841 A | 4/1995 | Lang et al. | |
| 7,166,596 B2 | 1/2007 | Yu et al. | |
| 8,153,658 B2 | 4/2012 | Hachiya et al. | |
| 10,259,803 B2 | 4/2019 | McDonald et al. | |
| 10,301,284 B2 | 5/2019 | McDonald et al. | |
| 10,730,874 B2 * | 8/2020 | Papaioannou | C07D 519/00 |
| 2010/0039029 A1 | 2/2010 | Yang et al. | |
| 2014/0213611 A1 | 7/2014 | Evans et al. | |
| 2016/0106102 A1 | 4/2016 | Kuebbeler et al. | |
| 2016/0168123 A1 | 6/2016 | Edwards et al. | |
| 2016/0200704 A1 | 7/2016 | Mcdonald et al. | |
| 2017/0029406 A1 | 2/2017 | Mcdonald et al. | |
| 2017/0305863 A1 | 10/2017 | Evans et al. | |
| 2018/0155348 A1 | 6/2018 | Li et al. | |
| 2018/0319782 A1 | 11/2018 | Davie et al. | |
| 2019/0127366 A1 | 5/2019 | Mcdonald et al. | |
| 2019/0169162 A1 | 6/2019 | Beaton et al. | |
| 2019/0284182 A1 | 9/2019 | Papaioannou et al. | |
| 2020/0239463 A1 | 7/2020 | Travins et al. | |
| 2020/0317667 A1 | 10/2020 | Papaioannou et al. | |
| 2021/0078999 A1 | 3/2021 | Papaioannou et al. | |

FOREIGN PATENT DOCUMENTS

| | | |
|---|---|---|
| CN | 105777632 A | 7/2016 |
| EP | 1908471 A1 | 4/2008 |
| EP | 1908762 A2 | 4/2008 |
| JP | S62181284 A | 8/1987 |
| JP | 2000256286 A | 9/2000 |
| JP | 2012111731 A | 6/2012 |
| WO | WO-92/20350 A1 | 11/1992 |
| WO | WO-96/05309 A2 | 2/1996 |
| WO | WO-97/36876 A1 | 10/1997 |
| WO | WO-02/00651 A2 | 1/2002 |
| WO | WO-2002/051831 A1 | 7/2002 |
| WO | WO-2005/005443 A1 | 1/2005 |
| WO | WO-2005/115382 A1 | 12/2005 |
| WO | WO-2006/091898 A2 | 8/2006 |
| WO | WO-2007/009236 A1 | 1/2007 |
| WO | WO-2007/128460 A1 | 11/2007 |
| WO | WO-2008/059854 A1 | 5/2008 |
| WO | WO-2008/116665 A1 | 10/2008 |
| WO | WO-2008/154642 A2 | 12/2008 |
| WO | WO-2009/023179 A2 | 2/2009 |
| WO | WO-2010/065760 A1 | 6/2010 |
| WO | WO-2010/091409 A1 | 8/2010 |
| WO | WO-2010/124082 A1 | 10/2010 |
| WO | WO-2010/124086 A1 | 10/2010 |
| WO | WO-2010/124102 A1 | 10/2010 |
| WO | WO-2010/124108 A1 | 10/2010 |
| WO | WO-2010/124112 A1 | 10/2010 |

(Continued)

OTHER PUBLICATIONS

Hampton, S. L. et al., KVD900 as a Single Dose, Rapid, Oral, Plasma Kallikrein Inhibitor for the On-Demand Treatment of Hereditary Angioedema Attacks: Pharmacokinetic and Pharmcodynamic results from a Phase 1 Single Ascending Dose Study, presented at AAAAI 2019, San Francisco, CA, Feb. 22-25, Poster (2019).
International Search Report for PCT/US2019/021897 (Substituted Imidazopyridines as Inhibitors of Plasma Kallikrein and Uses Thereof, filed Mar. 12, 2019), issued by ISA/EPO, 6 pages (dated May 9, 2019).
International Search Report for PCT/US2020/051249 filed Sep. 17, 2020, 5 pages, (dated Nov. 23, 2020).
International Search Report for PCT/US2020/051293 filed Sep. 17, 2020, 5 pages, (dated Nov. 10, 2020).
Li, Z. et al., Diversity-oriented synthesis of β-lactams and γ-lactams by post-Ugi nucleophilic cyclization: Lewis acids as regioselective switch, European Journal of Organic Chemistry, 18: 3957-3962 (2015).

(Continued)

*Primary Examiner* — Kahsay Habte
(74) *Attorney, Agent, or Firm* — Choate, Hall & Stewart LLP; John P. Rearick; Nicholas J. Pace

(57) ABSTRACT

The present invention provides compounds and compositions thereof which are useful as inhibitors of plasma kallikrein and which exhibit desirable characteristics for the same.

17 Claims, No Drawings

(56) References Cited

FOREIGN PATENT DOCUMENTS

| | | |
|---|---|---|
| WO | WO-2010/124114 A1 | 10/2010 |
| WO | WO-2010/124116 A1 | 10/2010 |
| WO | WO-2010/137738 A1 | 12/2010 |
| WO | WO-2011/135303 A2 | 11/2011 |
| WO | WO-2012/016133 A2 | 2/2012 |
| WO | WO-2012/051361 A1 | 4/2012 |
| WO | WO-2012/058645 A1 | 5/2012 |
| WO | WO-2012/082689 A1 | 6/2012 |
| WO | WO-2012/092471 A2 | 7/2012 |
| WO | WO-2012/116257 A1 | 8/2012 |
| WO | WO-2012/129562 A2 | 9/2012 |
| WO | WO-2012/139425 A1 | 10/2012 |
| WO | WO-2013/081094 A1 | 6/2013 |
| WO | WO-2013/101974 A1 | 7/2013 |
| WO | WO-2013/127269 A1 | 9/2013 |
| WO | WO-2014/187928 A1 | 11/2014 |
| WO | WO-2015/063093 A1 | 5/2015 |
| WO | WO-2015/095449 A1 | 6/2015 |
| WO | WO-2015/099196 A1 | 7/2015 |
| WO | WO-2015/103317 A1 | 7/2015 |
| WO | WO-2015/188051 A1 | 12/2015 |
| WO | WO-2016/011209 A1 | 1/2016 |
| WO | WO-2016/029146 A1 | 2/2016 |
| WO | WO-2016/083816 A1 | 6/2016 |
| WO | WO-2017/001924 A1 | 1/2017 |
| WO | WO-2017/001926 A2 | 1/2017 |
| WO | WO-2017/001936 A2 | 1/2017 |
| WO | WO-2017/161028 A1 | 9/2017 |
| WO | WO-2017/207983 A1 | 12/2017 |
| WO | WO-2017/207985 A1 | 12/2017 |
| WO | WO-2017/208005 A1 | 12/2017 |
| WO | WO-2018/011628 A1 | 1/2018 |
| WO | WO-2018/015818 A2 | 1/2018 |
| WO | WO-2018/141002 A2 | 8/2018 |
| WO | WO-2018/161033 A1 | 9/2018 |
| WO | WO-2018/229543 A2 | 12/2018 |
| WO | WO-2018/234808 A1 | 12/2018 |
| WO | WO-2019/028362 A1 | 2/2019 |
| WO | WO-2019/106375 A1 | 6/2019 |
| WO | WO-2019/106377 A1 | 6/2019 |
| WO | WO-2019/178129 A1 | 9/2019 |
| WO | WO-2021/055589 A1 | 3/2021 |
| WO | WO-2021/055621 A1 | 3/2021 |

OTHER PUBLICATIONS

Longhurst, H. et al., Oral Plasma Inhibitor BCX7353 is Safe and Effective as an On-Demand Treatment of Angioedema Attacks in Hereitary Angioedema (HAE) Patients: Results of the ZENITH-1 Trial, Presented at AAAAI 2019, San Francisco, CA, Feb. 22-25, Poster, (2019).

Nirogi, R. et al., Synthesis and SAR of Imidazo[1,5-a]pyridine derivatives as 5-HT4 receptor partial agonists for the treatment of cognitive disorders associated with Alzheimer's disease, European Journal of Medicinal Chemistry, 103: 289-301 (2015).

* cited by examiner

HETEROARYL PLASMA KALLIKREIN INHIBITORS

I. CROSS REFERENCE TO RELATED APPLICATIONS

This application claims priority to and the benefit of U.S. Provisional Patent Application Ser. No. 62/902,333, filed on Sep. 18, 2019, entitled "HETEROARYL PLASMA KALLIKREIN INHIBITORS," the entire content of which is incorporated herein by reference in its entirety.

II. BACKGROUND OF THE INVENTION

Plasma Kallikrein (pKal) is a serine protease zymogen in blood that is converted to its catalytically active form by coagulation factor XIIa, and contributes to the innate inflammatory response and intrinsic cascade of blood coagulation. The mechanisms that lead to the activation of this pathway in vivo include interactions with polyphosphates released from activated platelets and deficiency of C1 inhibitor (C1-INH), the primary physiological inhibitor of pKal. pKal-mediated cleavage of high-molecular weight kininogen generates the potent vasodilator and pro-inflammatory nonapeptide bradykinin (BK), which activates the bradykinin 2 receptor. Subsequent cleavage of BK by carboxypeptidases generates des-Arg9-BK, which activates the B1 receptor. Both B1 and B2 receptors are expressed by vascular, glial, and neuronal cell types, with the highest levels of retinal expression detected in the ganglion cell layer and inner and outer nuclear layers. Activation of B1 and B2 receptors causes vasodilation and increases vascular permeability.

pKal is also associated with a number of disorders, such as hereditary angioedema (HAE), an autosomal dominant disease characterized by painful, unpredictable, recurrent attacks of inflammation affecting the hands, feet, face, abdomen, urogenital tract, and the larynx. Prevalence for HAE is uncertain but is estimated to be approximately 1 case per 50,000 persons without known differences among ethnic groups. HAE is caused by deficient (Type I) or dysfunctional (Type II) levels of C1-INH, which inhibits pKal, bradykinin, and other serine proteases in the blood. Individuals with hereditary angioedema (HAE) are deficient in C1-INH and consequently undergo excessive bradykinin generation, which in turn cause painful, debilitating, and potentially fatal swelling attacks. If left untreated, HAE can result in a mortality rate as high as 40% primarily due to upper airway obstruction.

III. SUMMARY OF THE INVENTION

The present disclosure is based on, at least in part, the development of a number of compounds which bind to plasma kallikrein and effectively inhibit its activity. Accordingly, provided herein are compounds and uses thereof for targeting pKal and/or treating pKal-mediated diseases and disorders.

In some embodiments, the present invention provides a compound of Formula (I):

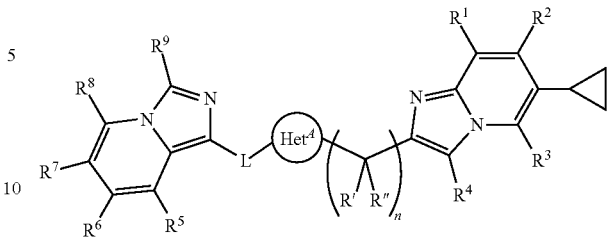

(I)

or a pharmaceutically acceptable salt thereof, wherein each of $Het^4$, L, R', R", $R^1$, $R^2$, $R^3$, $R^4$, $R^5$, $R^6$, $R^7$, $R^8$, and $R^9$ is defined and described in classes and subclasses herein. In certain embodiments, the present invention provides compounds of Formulae (I)-(III-b), as defined and described in classes and subclasses herein.

In some embodiments, the present invention also provides methods of using compounds of Formulae (I)-(III-b).

IV. DETAILED DESCRIPTION OF CERTAIN EMBODIMENTS

A. Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^t$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic C3-C7 hydrocarbon that is completely saturated or that contains one or more units of unsaturation, but which is not aromatic, that has a single point of attachment to the rest of the molecule.

Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-" refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O(CH$_2$)$_{0-4}$C(O)OR$^\circ$; —O(CH$_2$)$_{0-4}$OR$^\circ$;

—(CH$_2$)$_{0-4}$CH(OR$^o$)$_2$; —(CH$_2$)$_{0-4}$SR$^o$; —(CH$_2$)$_{0-4}$Ph, which may be substituted with R$^o$; —(CH$_2$)$_{0-4}$O(CH$_2$)$_{0-1}$Ph which may be substituted with R$^o$; —CH=CHPh, which may be substituted with R$^o$; —(CH$_2$)$_{0-4}$O(CH$_2$)$_{0-1}$-pyridyl which may be substituted with R$^o$; —NO$_2$; —CN; —N$_3$; —(CH$_2$)$_{0-4}$N(R$^o$)$_2$; —(CH$_2$)$_{0-4}$N(R$^o$)C(O)R$^o$; —N(R$^o$)C(S)R$^o$; —(CH$_2$)$_{0-4}$N(R$^o$)C(O)NR$^o{}_2$; —N(R$^o$)C(S)NR$^o{}_2$; —(CH$_2$)$_{0-4}$N(R$^o$)C(O)OR$^o$; —N(R$^o$)N(R$^o$)C(O)R$^o$; —N(R$^o$)N(R$^o$)C(O)NR$^o{}_2$; —N(R$^o$)N(R$^o$)C(O)OR$^o$; —(CH$_2$)$_{0-4}$C(O)R$^o$; —C(S)R$^o$; —(CH$_2$)$_{0-4}$C(O)OR$^o$; —(CH$_2$)$_{0-4}$C(O)SR$^o$; —(CH$_2$)$_{0-4}$C(O)OSiR$^o{}_3$; —(CH$_2$)$_{0-4}$OC(O)R$^o$; —OC(O)(CH$_2$)$_{0-4}$SR$^o$, —SC(S)SR$^o$; —(CH$_2$)$_{0-4}$SC(O)R$^o$; —(CH$_2$)$_{0-4}$C(O)NR$^o{}_2$; —C(S)NR$^o{}_2$; —C(S)SR$^o$; —SC(S)SR$^o$, —(CH$_2$)$_{0-4}$OC(O)NR$^o{}_2$; —C(O)N(OR$^o$)R$^o$; —C(O)C(O)R$^o$; —C(O)CH$_2$C(O)R$^o$; —C(NOR$^o$)R$^o$; —(CH$_2$)$_{0-4}$SSR$^o$; —(CH$_2$)$_{0-4}$S(O)$_2$R$^o$; —(CH$_2$)$_{0-4}$S(O)$_2$OR$^o$; —(CH$_2$)$_{0-4}$OS(O)$_2$R$^o$; —S(O)$_2$NR$^o{}_2$; —(CH$_2$)$_{0-4}$S(O)R$^o$; —N(R$^o$)S(O)$_2$NR$^o{}_2$; —N(R$^o$)S(O)$_2$R$^o$; —N(OR$^o$)R$^o$; —C(NH)NR$^o{}_2$; —P(O)$_2$R$^o$; —P(O)R$^o{}_2$; —OP(O)R$^o{}_2$; —OP(O)(OR$^o$)$_2$; SiR$^o{}_3$; —(C$_{1-4}$ straight or branched alkylene)O—N(R$^o$)$_2$; or —(C$_{1-4}$ straight or branched alkylene)C(O)O—N(R$^o$)$_2$, wherein each R$^o$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of R$^o$, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^o$ (or the ring formed by taking two independent occurrences of R$^o$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR'$_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^o$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6 membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(RT)S(O)$_2$R; wherein each R is independently hydrogen, C$_{1-6}$ aliphatic which may be substituted as defined below, unsubstituted-OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12 membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^\bullet$, -(haloR$^\bullet$), —OH, —OR$^\bullet$, —O(haloR$^\bullet$), —CN, —C(O)OH, —C(O)OR*, —NH$_2$, —NHR$^\bullet$, —NR$^\bullet{}_2$, or —NO$_2$, wherein each R$^{574}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

The symbol "∽", except when used as a bond to depict unknown or mixed stereochemistry, denotes the point of attachment of a chemical moiety to the remainder of a molecule or chemical formula.

The articles "a" and "an" are used herein to refer to one or to more than one (i.e., to at least one) of the grammatical object of the article. By way of example, "an element" means one element or more than one element.

A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

As will be understood from context, a "reference" sample or subject is one that is sufficiently similar to a particular sample or subject of interest to permit a relevant comparison. In some embodiments, information about a reference sample is obtained simultaneously with information about a particular sample. In some embodiments, information about a reference sample is historical. In some embodiments, information about a reference sample is stored, for example in a computer-readable medium. In some embodiments, comparison of a particular sample of interest with a reference sample establishes identity with, similarity to, or difference of the particular sample of interest relative to the reference.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood, e.g., whole blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from a subject. In some embodiments, obtained cells are or include cells from a subject from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood (e.g., whole blood), lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, the phrase "therapeutic agent" refers to any agent that has a therapeutic effect and/or elicits a desired biological and/or pharmacological effect, when administered to a subject.

As used herein, the term "therapeutically effective amount" refers to an amount of a therapeutic agent that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

B. Compounds

In some embodiments, a provided compound is of Formula (I):

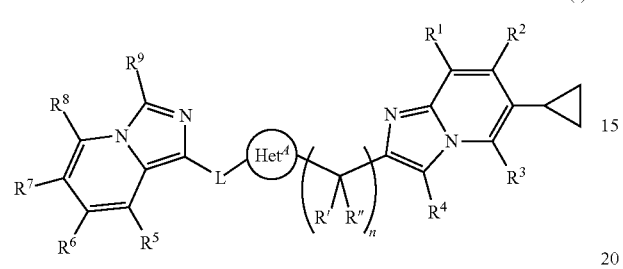

(I)

or a pharmaceutically acceptable salt thereof, wherein:

Het$^A$ is selected from a 3- to 7-membered saturated or partially unsaturated monocyclic heterocyclyene having 1-2 heteroatoms selected from oxygen, nitrogen, or sulfur, a 5- to 6-membered monocyclic heteroarylene having 1-4 heteroatoms selected from oxygen, nitrogen, or sulfur, a 7- to 10-membered saturated or partially unsaturated bicyclic heterocyclylene having 1-4 heteroatoms selected from oxygen, nitrogen, or sulfur, and a 7- to 10-membered bicyclic heteroarylene having 1-5 heteroatoms selected from oxygen, nitrogen, or sulfur, wherein Het$^A$ is substituted with 0-4 R$^A$ groups;

each R$^A$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

L is an optionally substituted C$_{1-6}$ hydrocarbon chain, wherein 1-3 methylene units are independently replaced with —Cy—, —O—, —NR—, —C(O)—, —S(O)$_2$—, —C(O)NR—, —NRC(O)—, —S(O)$_2$NR—, and —NRS(O)$_2$—;

—Cy— is 3- to 7-membered saturated or partially unsaturated monocyclic carbocyclylene, 3- to 7-membered saturated or partially unsaturated monocyclic heterocyclylene having 1-2 heteroatoms selected from oxygen, nitrogen, or sulfur, or 5- to 6-membered heteroarylene having 1-4 heteroatoms selected from oxygen, nitrogen, or sulfur;

R' and R" are independently selected from hydrogen, halogen, —OR, —NR$_2$, —SR, and optionally substituted C$_{1-6}$ aliphatic; wherein R' may be taken together with a monocyclic Het$^A$ to form an optionally substituted fused 7- to 10-membered saturated or partially unsaturated bicyclic heterocyclylene having 1-4 heteroatoms selected from oxygen, nitrogen, or sulfur; R$^1$, R$^2$, R$^3$, R$^4$, R$^5$, R$^6$, R$^7$, R$^8$, and R$^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;

n is 0 or 1.

In some embodiments, Het$^A$ is selected from the group consisting of 3- to 7-membered saturated or partially unsaturated monocyclic heterocyclylene having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein Het$^A$ is substituted with 0-4 R$^A$ groups.

In some embodiments, Het$^A$ is selected from the group consisting of 5- to 6-membered heteroarylene having 1-4 heteroatoms selected from oxygen, nitrogen, or sulfur, and 7- to 10-membered bicyclic heteroarylene having 1-4 heteroatoms selected from oxygen, nitrogen, or sulfur, wherein Het$^A$ is substituted with 0-4 R$^A$ groups.

In some embodiments, Het$^A$ is a 5- to 6-membered heteroarylene having 1-4 heteroatoms selected from oxygen, nitrogen, or sulfur.

In some embodiments, Het$^A$ is a 6-membered heteroarylene having 1-4 heteroatoms selected from oxygen, nitrogen, or sulfur, wherein Het$^A$ is substituted with 0-3 R$^A$ groups. In some embodiments, Het$^A$ is a 6-membered heteroarylene having 1 nitrogen, wherein Het$^A$ is substituted with 0-3 R$^A$ groups. In some embodiments, Het$^A$ is pyridinediyl. In some embodiments, Het$^A$ is selected from either:

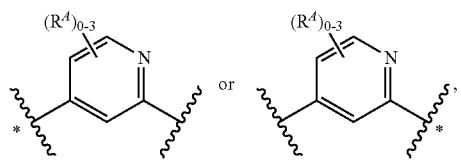

wherein * represents to point of attachment to L.

In some embodiments, $Het^4$ is a 5-membered heteroarylene having 1-4 heteroatoms selected from oxygen or nitrogen. In some embodiments, $Het^4$ is a 5-membered heteroarylene having 1-4 nitrogens. In some embodiments, $Het^4$ is a 5-membered heteroarylene having 1-4 nitrogens, wherein when $Het^4$ comprises 3 nitrogens, it is not a 1,2,4-triazolediyl. In some embodiments, $Het^4$ is a 5-membered heteroarylene having 1-3 nitrogens. In some embodiments, $Het^4$ is a 5-membered heteroarylene having 1-2 nitrogens. In some embodiments, $Het^4$ is a 5-membered heteroarylene having 1 nitrogen. In some embodiments, $Het^4$ is a 5-membered heteroarylene having 2 nitrogens. In some embodiments, $Het^4$ is a 5-membered heteroarylene having 3 nitrogens. In some embodiments, $Het^4$ is a 5-membered heteroarylene having 4 nitrogens.

In some embodiments, $Het^4$ is selected from the group consisting of:

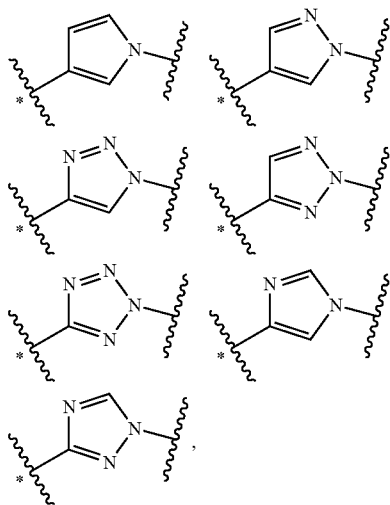

wherein * represents to point of attachment to L.

In some embodiments, $Het^4$ is a 5-membered monocyclic heteroarylene having 1-4 heteroatoms selected from oxygen, nitrogen, or sulfur, wherein $Het^4$ is substituted with 0-2 $R^A$ groups. In some embodiments, $Het^4$ is a 5-membered monocyclic heteroarylene having 1-3 heteroatoms selected from nitrogen, wherein $Het^4$ is substituted with 0-2 $R^A$ groups. In some embodiments, $Het^4$ is a 5-membered monocyclic heteroarylene having 2-3 heteroatoms selected from nitrogen, wherein $Het^4$ is substituted with 0-2 $R^A$ groups.

In some embodiments, $Het^4$ is a pyrrolediyl substituted with 0-3 $R^A$ groups. In some embodiments, $Het^4$ is a pyrazolediyl substituted with 0-2 $R^A$ groups. In some embodiments, $Het^4$ is a triazolediyl substituted with 0-1 $R^A$ groups. In some embodiments, $Het^4$ is a thiazolediyl substituted with 0-1 $R^A$ groups. In some embodiments, $Het^4$ is an unsubstituted tetrazolediyl. In some embodiments, $Het^4$ is an unsubstituted oxadiazolediyl. In some embodiments, $Het^4$ is an unsubstituted thiadiazolediyl. In some embodiments, $Het^4$ is an imidazolediyl substituted with 0-2 $R^A$ groups. In some embodiments, $Het^4$ is a oxazolediyl substituted with 0-1 $R^A$ groups. In some embodiments, $Het^4$ is an isoxazolediyl substituted with 0-1 $R^A$ groups. In some embodiments, $Het^4$ is an unsubstituted pyrazolediyl. In some embodiments, $Het^4$ is an unsubstituted 1,2,3-triazolediyl.

In some embodiments, $Het^4$ is selected from:

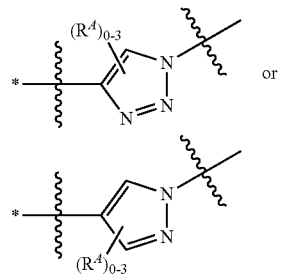

wherein * represents to point of attachment to L.

In some embodiments, $Het^4$ is a 7- to 10-membered bicyclic heteroarylene having 1-4 heteroatoms selected from oxygen, nitrogen, or sulfur wherein $Het^4$ is substituted with 0-4 $R^A$ groups. In some embodiments, $Het^4$ is a 9-membered bicyclic heteroarylene having 1-4 heteroatoms selected from oxygen, nitrogen, or sulfur wherein $Het^4$ is substituted with 0-4 $R^A$ groups. In some embodiments, $Het^4$ is a 9-membered bicyclic heteroarylene having 2 nitrogens wherein $Het^4$ is substituted with 0-4 $R^A$ groups. In some embodiments, $Het^4$ is a pyrrolopyridinediyl substituted with 0-4 $R^A$ groups.

In some embodiments, $Het^4$ is selected from the group consisting of:

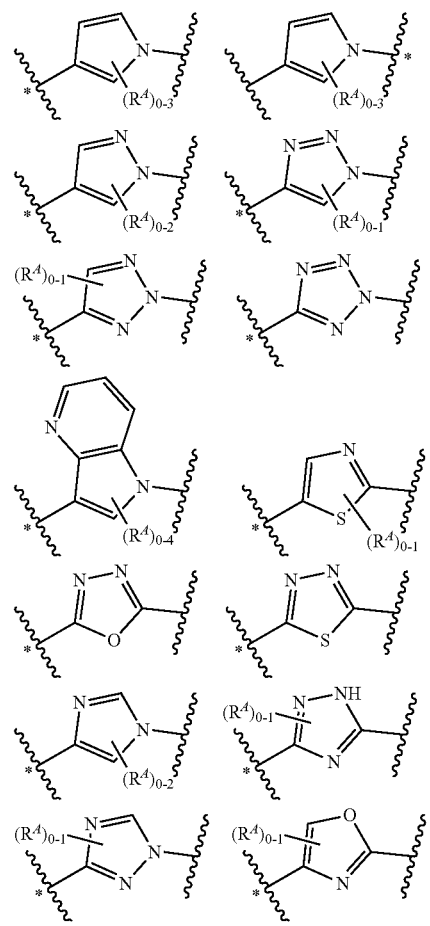

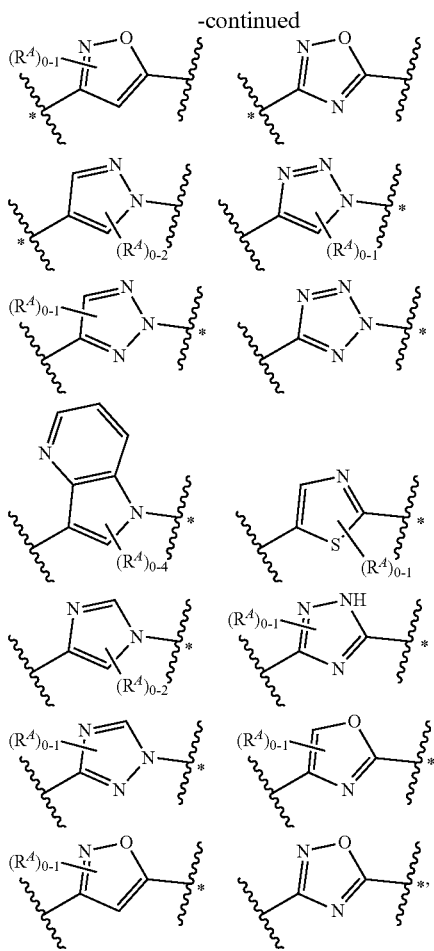

wherein * represents to point of attachment to L.

In some embodiments, each $R^A$ is independently selected from an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, substituents on an optionally substituted $R^A$ group are independently halogen, $(CH_2)_{0-4}R^\circ$, —$(CH_2)_{0-4}OR^\circ$; and —$(CH_2)_{0-4}C(O)OR^\circ$, wherein each $R^\circ$ is independently hydrogen, $C_{1-6}$ aliphatic, or a 5-6 membered saturated, partially unsaturated, or aryl ring having 0-4 heteroatoms independently selected from nitrogen, oxygen, or sulfur.

In some embodiments, a single instance of $R^A$ is $C_{1-6}$ aliphatic substituted with —$(CH_2)_{0-4}OR^\circ$, wherein $R^\circ$ is hydrogen or $C_{1-6}$ aliphatic.

In some embodiments, a single instance of $R^A$ is $C_{1-6}$ aliphatic substituted with —$(CH_2)_{0-4}C(O)OR^\circ$, wherein $R^\circ$ is hydrogen or $C_{1-6}$ aliphatic.

In some embodiments, a single instance of $R^A$ is $C_{1-6}$ aliphatic is substituted with 5-6 membered saturated, partially unsaturated, or aryl ring having 0-4 heteroatoms independently selected from nitrogen, oxygen, or sulfur.

In some embodiments, a single instance of $R^A$ is optionally substituted 3- to 7-membered saturated or partially unsaturated monocyclic carbocyclyl. In some embodiments, a single instance of $R^A$ is optionally substituted cyclopropyl.

In some embodiments, a single instance of $R^A$ is cyclopropyl substituted with-$(CH_2)_{0-4}C(O)OR^\circ$ and $R^\circ$ is hydrogen or $C_{1-6}$ aliphatic.

In some embodiments, a single instance of $R^A$ is $C_{1-6}$ aliphatic substituted with halogen. In some embodiments, $R^A$ is $C_{1-3}$ aliphatic substituted with halogen. In some embodiments, $R^A$ is $C_1$ aliphatic substituted with halogen. In some embodiments, $R^A$ is $C_1$ aliphatic substituted with fluorine. In some embodiments, $R^A$ is-$CHF_2$.

In certain embodiments, L is selected from —$C(R)_2NRC(O)$-#, —$C(R)_2C(O)NRC(R)_2$-#, —$C(R)_2NRC(O)C(R)_2$-#, —$C(R)_2NRC(R)_2$-#, —$C(R)_2C(R)_2NRC(R)_2$-#, —$C(O)NRC(R)_2$-#, —$C(R)_2C(O)NR$-#, —$NRC(O)C(R)_2$-#, —$CR_2C(O)NRC(R)_2$-#, —$SO_2NRC(R)_2$-#, and —$C(R)_2NRSO_2$-#, wherein # represents the point of attachment to $Het^A$.

In certain embodiments, L is selected from —$C(R)_2NRC(O)$-#, —$C(R)_2C(O)NRC(R)_2$-#, —$C(R)_2NRC(R)_2$-#, —$C(R)_2C(R)_2NRC(R)_2$-#, —$C(O)NRC(R)_2$-#, —$C(R)_2C(O)NR$-#, —$CR_2C(O)NRC(R)_2$-#, —$SO_2NRC(R)_2$-#, and —$C(R)_2NRSO_2$-#, wherein # represents the point of attachment to $Het^A$.

In certain embodiments, L is selected from —$C(R)_2C(O)NRC(R)_2$-#, —$C(R)_2NRC(R)_2$-#, —$C(R)_2C(R)_2NRC(R)_2$-#, —$C(O)NRC(R)_2$-#, —$C(R)_2C(O)NRC(R)_2$-#, —$SO_2NRC(R)_2$-#, and —$C(R)_2NRSO_2$-#, wherein # represents the point of attachment to $Het^A$ In some embodiments, L is other than —$C(R)_2NRC(O)$-# or —$C(R)_2C(O)NR$-#. In some embodiments, L is other than-$CH_2NRC(O)$-# or —$CH_2C(O)NR$-#.

In some embodiments, when L is —$C(R)_2NRC(O)$-# or —$C(R)_2C(O)NR$-#, one of the following (a), (b), or (c) applies:

(a) n is 0;
(b) at least one of $R^5$, $R^6$, $R^7$, $R^8$, and $R^9$ is CN; or
(c) $R^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

In some embodiments, when L is —$C(R)_2NRC(O)$-# or —$C(R)_2C(O)NR$-#, n is 0.

In some embodiments, when L is —$C(R)_2NRC(O)$-# or —$C(R)_2C(O)NR$-#, R' is taken together with a monocyclic $Het^A$ to form an optionally substituted fused 7- to 10-membered saturated or partially unsaturated bicyclic heterocyclylene having 1-4 heteroatoms selected from oxygen, nitrogen, or sulfur.

In some embodiments, when L is-$CH_2NRC(O)$-# or —$CH_2C(O)NR$-#, R' is taken together with a monocyclic $Het^A$ to form an optionally substituted fused 7- to 10-membered saturated or partially unsaturated bicyclic heterocyclylene having 1-4 heteroatoms selected from oxygen, nitrogen, or sulfur.

In certain embodiments, when L is —(CR$_2$)$_m$NRC(O)— and m is 0 to 2 (e.g., 0 or 2), one of the following (a), (b), or (c) applies:
  (a) n is 0;
  (b) at least one of R$^5$, R$^6$, R$^7$, R$^8$, and R$^9$ is CN; or
  (c) R$^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

In certain embodiments, when L is —(CR$_2$)$_m$NRC(O)— and m is 0, then n is 0. In certain embodiments, when L is —(CR$_2$)$_m$NRC(O)— and m is 1, then n is 0. In certain embodiments, when L is —(CR$_2$)$_m$NRC(O)— and m is 2, then n is 0.

In certain embodiments, when L is —(CR$_2$)$_m$NRC(O)— and m is 0 to 2 (e.g., 0 or 2), R' is taken together with a monocyclic Het$^4$ to form an optionally substituted fused 7- to 10-membered saturated or partially unsaturated bicyclic heterocyclylene having 1-4 heteroatoms selected from oxygen, nitrogen, or sulfur.

In some embodiments, L is —C(R)$_2$C(O)NRC(R)$_2$-#, wherein each R is independently hydrogen or C$_{1-3}$ aliphatic optionally substituted with halogen. In some embodiments, L is —CH$_2$C(O)NHCH(CF$_3$)-#. In some embodiments, L is —CH$_2$C(O)NHCH(CH$_3$)-#.

In some embodiments, L is —C(R)$_2$NRC(R)$_2$-#, wherein each R is independently hydrogen or C$_{1-3}$ aliphatic optionally substituted with halogen. In some embodiments, L is —CH$_2$NHCH(CF$_3$)-#. In some embodiments, L is —CH$_2$NHCH$_2$-#. In some embodiments, L is —CH$_2$NHCH(CH$_3$)-#. In some embodiments, L is —CH(CF$_3$)NHCH$_2$-#.

In certain embodiments, L is —C(R)$_2$NRSO$_2$-#, wherein each R is independently hydrogen or C$_{1-3}$ aliphatic optionally substituted with halogen. In certain embodiments, L is-CH$_2$NHSO$_2$-#.

In some embodiments, L is —SO$_2$NRC(R)$_2$-#, wherein each R is independently hydrogen or C$_{1-3}$ aliphatic optionally substituted with halogen. In some embodiments, L is —SO$_2$NHCH$_2$-#. In some embodiments, L is —SO$_2$NHCH(CH$_3$)-#.

In some embodiments, L is —C(O)NRC(R)$_2$-#, wherein each R is independently hydrogen or C$_{1-3}$ aliphatic optionally substituted with halogen. In some embodiments, L is —C(O)NHCH$_2$-#.

In certain embodiments, L is —C(R)$_2$C(O)NRC(R)$_2$-#, wherein each R is independently hydrogen or C$_{1-3}$ aliphatic optionally substituted with halogen. In certain embodiments, L is —CH$_2$C(O)NHCH$_2$-#.

In some embodiments, R' and R" are each hydrogen. In some embodiments, R" is hydrogen and R' is taken together with a monocyclic Het$^4$ to form a fused 7- to 10-membered saturated or partially unsaturated bicyclic heterocyclylene having 1-4 heteroatoms selected from oxygen, nitrogen, or sulfur. In some embodiments, n is 1, R" is hydrogen and R' is taken together with a monocyclic Het$^4$ to form a fused 7- to 10-membered saturated or partially unsaturated bicyclic heterocyclylene having 1-4 heteroatoms selected from oxygen, nitrogen, or sulfur. In some embodiments, n is 1, R" is hydrogen and R' is taken together with a monocyclic Het$^4$ to form a fused 8-membered saturated or partially unsaturated bicyclic heterocyclylene having 1-4 heteroatoms selected from oxygen, nitrogen, or sulfur.

In some embodiments, R' and R" are independently selected from hydrogen, halogen, —OR, —SR, —NR$_2$, and optionally substituted C$_{1-6}$ aliphatic, wherein each R is independently selected from hydrogen and C$_{1-6}$ aliphatic. In some embodiments, R' and R" are independently selected from hydrogen, fluorine, —OH, —SH, —NH$_2$, and C$_{1-6}$ aliphatic substituted with —(CH$_2$)$_{0-4}$C(O)OR$^o$, wherein R$^o$ is hydrogen or C$_{1-6}$ aliphatic. In some embodiments, R' and R" are independently selected from hydrogen, fluorine, —OH, and C$_{1-6}$ aliphatic substituted with —(CH$_2$)$_{0-4}$C(O)OR$^o$, wherein R$^o$ is hydrogen, methyl or ethyl.

In some embodiments, when n is 0, Het$^4$ is a 7- to 10-membered saturated or partially unsaturated bicyclic heterocyclylene having 1-4 heteroatoms selected from oxygen, nitrogen, or sulfur.

In some embodiments, n is 0. In some embodiments, n is 1.

In some embodiments, R$^1$, R$^2$, R$^3$, and R$^4$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur. In some embodiments, R$^1$, R$^2$, R$^3$, and R$^4$ are independently selected from hydrogen, halogen, —CN, —C(O)$_2$R, or an optionally substituted group selected from C$_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur.

In some embodiments, substituents on an optionally substituted R$^1$, R$^2$, R$^3$, and R$^4$ are each independently halogen, —CN, (CH$_2$)$_{0-4}$R$^o$, —(CH$_2$)$_{0-4}$OR$^o$, —(CH$_2$)$_{0-4}$N(R$^o$)$_2$, —(CH$_2$)$_{0-4}$O(CH$_2$)$_{1-4}$N(R$^o$)$_2$ and —(CH$_2$)$_{0-4}$C(O)OR$^o$, wherein each R$^o$ is independently hydrogen, C$_{1-6}$ aliphatic, or a 3- to 5-membered saturated, partially unsaturated, or aryl ring having 1-2 heteroatoms independently selected from nitrogen, oxygen, or sulfur.

In some embodiments, substituents on an optionally substituted R$^1$, R$^2$, R$^3$, and R$^4$ are each independently —F, —CN, —R$^o$, —OR$^o$, —N(R$^o$)$_2$, —COOR$^o$, or —OC(R$^o$)$_2$C(R$^o$)$_2$N(R$^o$)$_2$ wherein each R$^o$ is independently hydrogen, C$_{1-6}$ aliphatic, or a 4-membered saturated ring having 1-2 heteroatoms independently selected from nitrogen, oxygen, or sulfur. In some embodiments, substituents on an optionally substituted R$^1$, R$^2$, R$^3$, and R$^4$ are each independently selected from —F, —CN, —CH₃, —OH, —NH₂, —COOH, —COOCH₂CH₂, —OCH₂CH₂NH₂, —OCH₂CH₂N(CH₃)₂, and

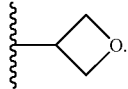

In some embodiments, each of $R^1$, $R^2$, $R^3$, and $R^4$ is independently selected from hydrogen, halogen, —CN, —C(O)R, —C(O)₂R, —N(R)₂, —OR, or an optionally substituted group selected from $C_{1-6}$ aliphatic, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur, wherein each R is independently hydrogen or $C_{1-6}$ aliphatic.

In some embodiments, substituents on an optionally substituted $R^1$, $R^2$, $R^3$, or $R^4$ group are independently selected from halogen, —(CH₂)₀₋₄OR°, —O(CH₂)₀₋₄OR°, —(CH₂)₀₋₄C(O)OR°, and —(CH₂)₀₋₄N(R°)₂ wherein each R° is independently hydrogen, $C_{1-6}$ aliphatic, or two independent occurrences of R°, taken together with their intervening atom(s), form an optionally substituted 3-12 membered saturated, partially unsaturated, or aryl mono- or bicyclic ring having 0-4 heteroatoms independently selected from nitrogen, oxygen, or sulfur, which may be further substituted.

In some embodiments, R' is selected from hydrogen, halogen, —CN, —C(O)₂R, —C(O)N(R)₂, —N(R)₂, —OR, —SR, —S(O)₂N(R)₂, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur. In some embodiments, $R^1$ is selected from hydrogen, halogen, —CN, —C(O)₂R, or an optionally substituted group selected from $C_{1-6}$ aliphatic, 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur.

In some embodiments, a substituent on an optionally substituted $R^1$ is —F, —CN, —R°, —OR°, —N(R°)₂, —COOR°, or —OC(R°)₂C(R°)₂N(R°)₂ wherein each R° is independently hydrogen, $C_{1-6}$ aliphatic, or a 4-membered saturated ring having 1-2 heteroatoms independently selected from nitrogen, oxygen, or sulfur. In some embodiments, substituents on an optionally substituted $R^1$ is selected from —F, —CN, —CH₃, —OH, —NH₂, —COOH, —COOCH₂CH₂, —OCH₂CH₂NH₂, —OCH₂CH₂N(CH₃)₂, and a

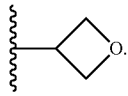

In some embodiments, $R^5$, $R^6$, $R^7$, $R^8$, and $R^9$ are independently selected from hydrogen, halogen, —CN, —N(R)₂, —OR, or an optionally substituted group selected from $C_{1-6}$ aliphatic, 3- to 7-membered saturated or partially unsaturated monocyclic carbocyclyl, wherein each R is independently hydrogen or $C_{1-6}$ aliphatic. In some embodiments, $R^7$, $R^8$, and $R^9$ are hydrogen.

In some embodiments, $R^5$ is selected from hydrogen or halogen. In some embodiments, $R^5$ is hydrogen. In some embodiments $R^5$ is halogen. In some embodiments $R^5$ is F. In some embodiments $R^5$ is Cl. In some embodiments $R^5$ is Br. In some embodiments $R^5$ is I.

In some embodiments, $R^6$ is selected from halogen or an optionally substituted $C_{1-6}$ aliphatic. In some embodiments $R^6$ is halogen. In some embodiments $R^6$ is F. In some embodiments $R^6$ is Cl. In some embodiments $R^6$ is Br. In some embodiments $R^6$ is I. In some embodiments, $R^6$ is optionally substituted $C_{1-6}$ aliphatic. In some embodiments, $R^6$ is optionally substituted $C_{1-5}$ aliphatic. In some embodiments, $R^6$ is optionally substituted $C_{1-4}$ aliphatic. In some embodiments, $R^6$ is optionally substituted $C_{1-3}$ aliphatic. In some embodiments, $R^6$ is optionally substituted $C_{1-2}$ aliphatic. In some embodiments, $R^6$ is alkynyl.

In certain embodiments, each of $R^1$, $R^2$, $R^3$, $R^4$, $R^5$, $R^7$, $R^8$, and $R^9$ are hydrogen. In certain embodiments, each of $R^1$, $R^2$, $R^3$, $R^4$, $R^7$, $R^8$, and $R^9$ are hydrogen. In certain embodiments, each of $R^2$, $R^3$, $R^4$, $R^5$, $R^7$, $R^8$, and $R^9$ are hydrogen.

In some embodiments, $R^9$ is hydrogen, $R^6$ is —F, —Cl, or —Br, and $R^5$, $R^7$, and $R^8$ are independently selected from hydrogen, halogen, —CN, —C(R)=N(R), —C(O)R, —C(O)₂R, —C(O)N(R)₂, —NO₂, —N(R)—N(R)₂, —N(R)₂, —N(R)C(O)R, —N(R)C(O)₂R, —N(R)C(O)N(R)₂, —N(R)S(O)₂R, —OR, —OC(O)R, —OC(O)N(R)₂, —SR, —S(O)R, —S(O)₂R, —S(O)N(R)₂, —S(O)₂N(R)₂, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur.

In some embodiments, $R^1$ is an optionally substituted group selected from 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur. In some embodiments, $R^1$ is an optionally substituted 5-membered heteroaryl having 2-4 heteroatoms selected from oxygen or nitrogen. In some embodiments, $R^1$ is an optionally substituted piperizinyl. In some embodiments, $R^1$ is an optionally substituted triazolyl.

In some embodiments, $R^1$ is optionally substituted $C_{1-6}$ aliphatic. In some embodiments, substituents on an optionally substituted $R^1$ group are independently halogen, —(CH₂)₀₋₄R°, —(CH₂)₀₋₄OR°; and —(CH₂)₀₋₄C(O)OR°, wherein each R° is independently hydrogen, $C_{1-6}$ aliphatic, or a 5-6 membered saturated, partially unsaturated, or aryl ring having 0-4 heteroatoms independently selected from nitrogen, oxygen, or sulfur.

In some embodiments, $R^5$ and $R^6$ are each independently halogen. In some embodiments, $R^5$ is F and $R^6$ is Cl. In some embodiments, $R^6$ is Cl. In some embodiments, $R^6$ is CN.

In some embodiments, a provided compound, or a pharmaceutically acceptable salt thereof, has a structure of Formula (I-a), Formula (I-b), Formula (I-c), or Formula (I-d):

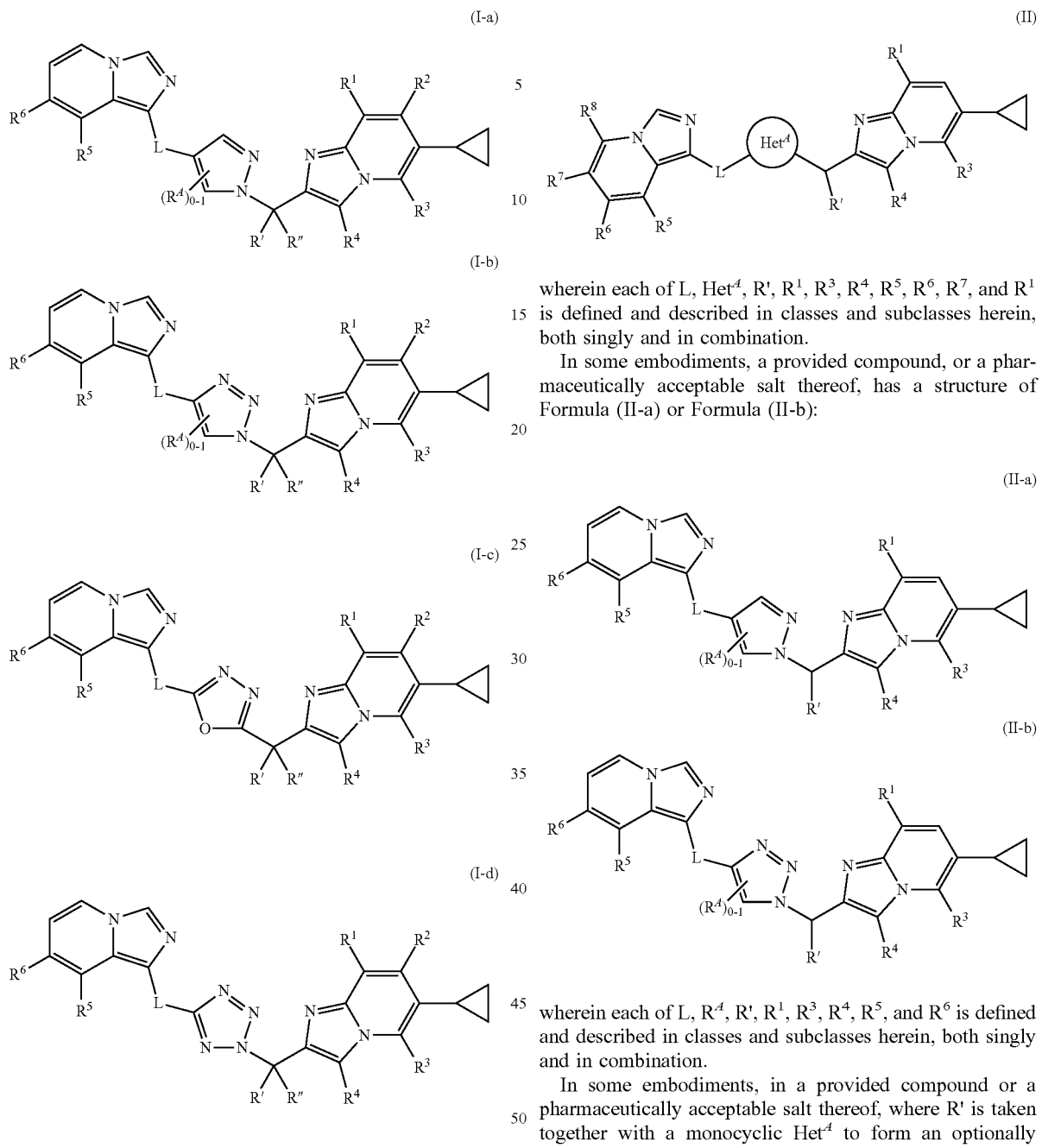

wherein each of L, R⁴, R', R", R¹, R², R³, R⁴, R⁵, and R⁶ is defined and described in classes and subclasses herein, both singly and in combination.

It will be understood that, unless otherwise specified or prohibited by the foregoing definition of Formula (I), embodiments of variables L, R⁴, Het⁴, R', R", R¹, R², R³, R⁴, R⁵, R⁶, R⁷, and R⁸ as defined above and described in classes and subclasses herein, also apply to compounds of Formula (I-a), Formula (I-b), Formula (I-c), Formula (I-d), Formula (II), Formula (II-a), Formula (II-b), Formula (III), Formula (III-a), and Formula (III-b), both singly and in combination.

In some embodiments, a provided compound, or a pharmaceutically acceptable salt thereof, has a structure of Formula (II):

wherein each of L, Het⁴, R', R¹, R³, R⁴, R⁵, R⁶, R⁷, and R¹ is defined and described in classes and subclasses herein, both singly and in combination.

In some embodiments, a provided compound, or a pharmaceutically acceptable salt thereof, has a structure of Formula (II-a) or Formula (II-b):

wherein each of L, R⁴, R', R¹, R³, R⁴, R⁵, and R⁶ is defined and described in classes and subclasses herein, both singly and in combination.

In some embodiments, in a provided compound or a pharmaceutically acceptable salt thereof, where R' is taken together with a monocyclic Het⁴ to form an optionally substituted fused ring, the compound has a structure of Formula (III):

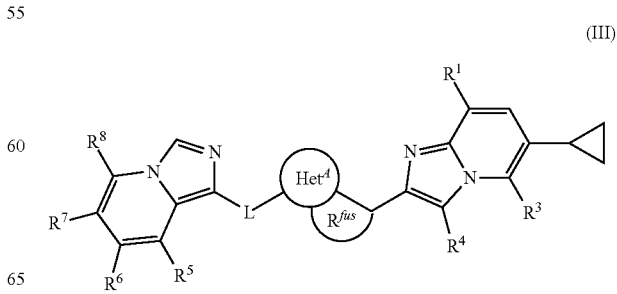

wherein R$^{fus}$ is fused with Het$^A$ to form a fused 7- to 10-membered saturated or partially unsaturated bicyclic heterocyclylene having 1-4 heteroatoms selected from oxygen, nitrogen, or sulfur, and each of L, Het$^A$, R$^1$, R$^3$, R$^4$, R$^5$, R$^6$, R$^7$, and R$^8$ is defined and described in classes and subclasses herein, both singly and in combination.

In some embodiments, a provided compound, or a pharmaceutically acceptable salt thereof, has a structure of Formula (III-a) or Formula (III-b):

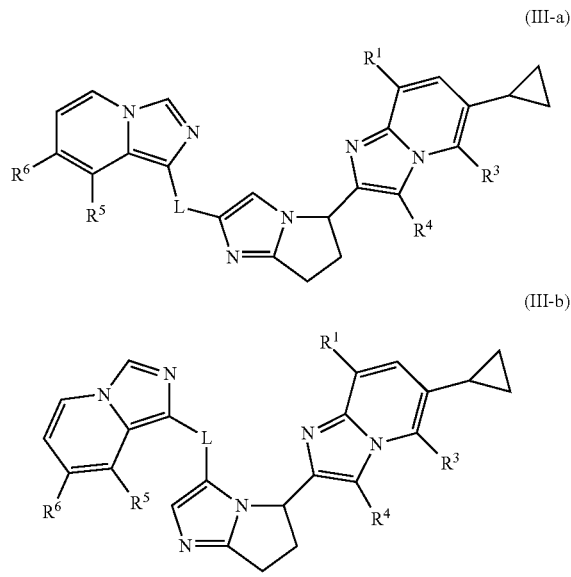

wherein each of L, R$^1$, R$^3$, R$^4$, R$^5$, and R$^6$ is defined and described in classes and subclasses herein, both singly and in combination.

In some embodiments, a provided compound is selected from the group consisting of: 2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1), 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine (I-2), 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (I-3), N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide (I-4), N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide (I-5), 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-sulfonamide (I-6), 7-chloro-N-(1-(1-((6-cyclopropylimidazo[1,2-a]pyridin-2-yl)methyl)-1H-1,2,3-triazol-4-yl)ethyl)-8-fluoroimidazo[1,5-a]pyridine-1-sulfonamide (I-7), N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (I-8), N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-3-carboxamide (I-9), N-((7-cyanoimidazo[1,5-a]pyridin-1-yl)methyl)-1-((6-cyclopropylimidazo[1,2-a]pyridin-2-yl)methyl)-1H-pyrazole-4-carboxamide (I-10), 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (I-11), N-((7-chloro-8-fluoroimidazo[1,5-a]pyridin-1-yl)methyl)-1-(1-((6-cyclopropylimidazo[1,2-a]pyridin-2-yl)methyl)-1H-1,2,3-triazol-4-yl)ethan-1-amine (I-12), 2-(7-chloroimidazo[1,5-a]pyridin-1-yl)-N-(1-(1-((6-cyclopropylimidazo[1,2-a]pyridin-2-yl)methyl)-1H-1,2,3-triazol-4-yl)ethyl)acetamide (I-13), methyl 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (I-14), 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylic acid (I-15), N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (I-16), ethyl 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (I-17a), 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid (I-17b), 1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (I-18), 2-(7-chloroimidazo[1,5-a]pyridin-1-yl)-N-(1-(1-((6-cyclopropylimidazo[1,2-a]pyridin-2-yl)methyl)-1H-pyrazol-4-yl)-2,2,2-trifluoroethyl)acetamide (I-19), N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide (I-20), or a pharmaceutically acceptable salt thereof.

C. Pharmaceutical Compositions

In another aspect, the present invention provides pharmaceutical compositions comprising a compound of Formulae (I)-(III-b) or a compound of Formulae (I)-(III-b) in combination with a pharmaceutically acceptable excipient (e.g., carrier).

The pharmaceutical compositions include optical isomers, diastereomers, or pharmaceutically acceptable salts of the inhibitors disclosed herein. A compound of Formulae (I)-(III-b) included in the pharmaceutical composition may be covalently attached to a carrier moiety, as described above. Alternatively, a compound of Formulae (I)-(III-b) included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

In some embodiments, a test agent as described herein can be incorporated into a pharmaceutical composition for administration by methods known to those skilled in the art and described herein for provided compounds.

D. Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

E. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat HAE, such compositions will contain an amount of active ingredient effective to achieve the desired result (e.g. inhibiting pKal and/or decreasing the amount of bradykinin in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to pKal inhibition); presence of other diseases or other health-related problems; kind of concurrent treatment; and complications from any disease or treatment regimen. Other therapeutic regimens or agents can be used in conjunction with the methods and compounds of the invention.

For any provided compound or test agent, the therapeutically effective amount can be initially determined from cell culture assays. Target concentrations will be those concentrations of active compound(s) that are capable of decreasing pKal enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring pKal inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% (w/v). In some embodiments, the dosage range is 0.1% to 5% (w/v).

Dosage amounts and intervals can be adjusted individually to provide levels of the administered compound effective for the particular clinical indication being treated. This will provide a therapeutic regimen that is commensurate with the severity of the individual's disease state.

F. Methods of Treatment

The present disclosure provides compounds for use in medicine. The present disclosure further provides the use of any compounds described herein for inhibiting the activity of pKal, which would be beneficial to treatment of pKal-mediated diseases and conditions. Exemplary pKal-mediated disorders include edema, which refers to swelling in the whole body of a subject or a part thereof due to inflammation or injury when small blood vessels become leaky and releases fluid into nearby tissues. In some examples, the edema is HAE. In other examples, the edema occurs in eyes, e.g., diabetic macular edema (DME). The present disclosure provides methods of inhibiting the activity of pKal. In certain embodiments, the application provides a method of inhibiting the activity of pKal in vitro via contacting any of the compounds described herein with pKal molecules in a sample, such as a biological sample. In certain embodiments, the application provides a method of inhibiting the activity of pKal in vivo via delivering an effective amount of any of the compounds described herein to a subject in need of the treatment through a suitable route.

In certain embodiments, the methods comprise administering to a subject in need thereof (e.g., a subject such as a human patient with edema) any of the compounds described herein or a pharmaceutically acceptable salt thereof. In certain embodiments, the methods comprise administering a compound of Formulae (I)-(III-b), or a pharmaceutically acceptable salt or composition thereof, to a subject in need thereof. In some embodiments, the method comprises administering a pharmaceutical composition comprising a compound of Formulae (I)-(III-b), or a pharmaceutically acceptable salt to a subject in need thereof.

In certain embodiments, the subject to be treated by any of the methods described herein is a human patient having, suspected of having, or at risk for edema, for example, HAE or diabetic macular edema (DME). A subject having an edema can be identified by routine medical examination, e.g., laboratory tests. A subject suspected of having an edema might show one or more symptoms of the disease/disorder. A subject at risk for edema can be a subject having one or more of the risk factors associated with the disease, for example, deficiency in C1-INH as for HAE.

In certain embodiments, provided herein are methods of alleviating one or more symptoms of HAE in a human patient who is suffering from an HAE attack. Such a patient can be identified by routine medical procedures. An effective amount of one or more of the provided compounds can be given to the human patient via a suitable route, for example, those described herein. The compounds described herein may be used alone, or may be used in combination with other anti-HAE agents, for example, a C1 esterase inhibitor (e.g., Cinryze© or Berinert©), a pKal inhibitor (e.g., ecallantide or lanadelumab) or a bradykinin B2 receptor antagonist (e.g., Firazyr®).

In other embodiments, provided herein are methods or reducing the risk of HAE attack in a human HAE patient who is in quiescent stage. Such a patient can be identified based on various factors, including history of HAE attack. An effective amount of one or more of the compounds can be given to the human patient via a suitable route, for example, those described herein. The compounds described herein may be used alone, or may be used in combination with other anti-HAE agents, for example, a C1 esterase inhibitor (e.g., Cinryze® or Berinert®), a pKal inhibitor (e.g., ecallantide or lanadelumab) or a bradykinin B2 receptor antagonist (e.g., Firazyr®).

In yet other embodiments, provided herein are prophylactic treatment of HAE in human patients having risk to HAE attacks with one or more of the compounds described herein. Patients suitable for such prophylactic treatment may be human subjects having history of HAE attacks (e.g., human subjects experiencing more than 2 attacks per month). Alternatively, patients suitable for the prophylactic treatment may be human subjects having no HAE attack history but bearing one or more risk factors for HAE (e.g., family history, genetic defects in C1-INH gene, etc.). Such prophylactic treatment may involve the compounds described herein as the sole active agent, or involve additional anti-HAE agents, such as those described herein.

In certain embodiments, provided herein are methods for preventing or reducing edema in an eye of a subject (e.g., a human patient). In some examples, the human patient is a diabetic having, suspected of having, or at risk for diabetic macular edema (DME). DME is the proliferative form of diabetic retinopathy characterized by swelling of the retinal layers, neovascularization, vascular leak, and retinal thickening in diabetes mellitus due to leaking of fluid from blood vessels within the macula. To practice this method, an effective amount of one or more of the compounds described herein, or pharmaceutically acceptable salts thereof, may be delivered into the eye of the subject where treatment is needed. For example, the compound may be delivered by intraocular injection, or intravitreal injection. A subject may be treated with the compound as described herein, either as the sole active agent, or in combination with another treatment for DME. Non-limiting examples of treatment for DME include laser photocoagulation, steroids, VEGF pathway targeting agents (e.g., Lucentis® (ranibizumab) or Eylea© (aflibercept)), and/or anti-PDGF agents.

In certain embodiments, the methods disclosed herein comprise administering to the subject an effective amount of a compound of Formulae (I)-(III-b), or a pharmaceutically acceptable salt or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formulae (I)-(III-b), or at different times than the compound of Formulae (I)-(III-b). For example, the compound of Formulae (I)-(III-b) and any additional pharmaceutical agent(s) may be on the same dosing schedule or different dosing schedules. All or some doses of the compound of Formulae (I)-(III-b) may be administered before all or some doses of an additional pharmaceutical agent, after all or some does an additional pharmaceutical agent, within a dosing schedule of an additional pharmaceutical agent, or a combination thereof. The timing of administration of the compound of Formulae (I)-(III-b) and additional pharmaceutical agents may be different for different additional pharmaceutical agents.

In certain embodiments, the additional pharmaceutical agent comprises an agent useful in the treatment of an edema, such as HAE or DME.

V. Exemplary Embodiments

The present disclosure contemplates, among other things, the following numbered embodiments:
1. A compound of Formula (I):

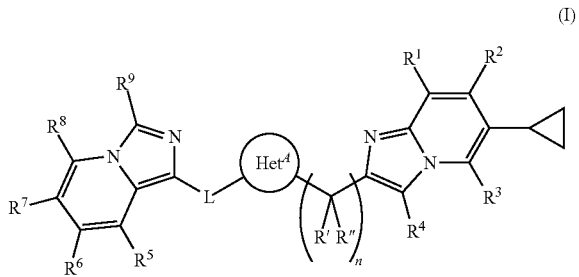

(I)

or a pharmaceutically acceptable salt thereof,
wherein:
Het$^4$ is selected from a 3- to 7-membered saturated or partially unsaturated monocyclic heterocyclyene having 1-2 heteroatoms selected from oxygen, nitrogen, or sulfur, a 5- to 6-membered monocyclic heteroarylene having 1-4 heteroatoms selected from oxygen, nitrogen, or sulfur, a 7- to 10-membered saturated or partially unsaturated bicyclic heterocyclylene having 1-4 heteroatoms selected from oxygen, nitrogen, or sulfur, and a 7- to 10-membered bicyclic heteroarylene having 1-5 heteroatoms selected from oxygen, nitrogen, or sulfur, wherein Het$^4$ is substituted with 0-4 R$^4$ groups;
each R$^4$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from C$_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;
L is an optionally substituted C$_{1-6}$ hydrocarbon chain, wherein 1-3 methylene units are independently replaced with —Cy—, —C(R)$_2$— —O—, —NR—, —C(O)—, —S(O)$_2$—, —C(O)NR—, —NRC(O)—, —S(O)$_2$NR—, and —NRS(O)$_2$—;
—Cy— is 3- to 7-membered saturated or partially unsaturated monocyclic carbocyclene, 3- to 7-membered saturated or partially unsaturated monocyclic heterocyclylene having 1-2 heteroatoms selected from oxygen, nitrogen, or sulfur, or 5- to 6-membered heteroarylene having 1-4 heteroatoms selected from oxygen, nitrogen, or sulfur;
R' and R" are independently selected from hydrogen, halogen, —OR, —NR$_2$, —SR, and optionally substituted C$_{1-6}$ aliphatic; wherein R' may be taken together with a monocyclic Het$^4$ to form an optionally substituted fused 7- to 10-membered saturated or partially unsaturated bicyclic heterocyclylene having 1-4 heteroatoms selected from oxygen, nitrogen, or sulfur;

$R^1$, $R^2$, $R^3$, $R^4$, $R^5$, $R^6$, $R^7$, $R^8$, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur; and each R is independently hydrogen or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur;

n is 0 or 1.

2. The compound according to embodiment 1, wherein when L is —(CR$_2$)$_m$NRC(O)— and m is 0 to 2 (e.g., 0 or 2), one of the following (a), (b), or (c) applies:
 (a) n is 0;
 (b) at least one of $R^5$, $R^6$, $R^7$, $R^8$, and $R^9$ is CN; or
 (c) $R^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

3. The compound according to any one of the preceding embodiments, wherein L is selected from the group consisting of —C(R)$_2$NRC(O)-#, —C(R)$_2$C(O)NRC(R)$_2$-#, —C(R)$_2$NRC(O)C(R)$_2$-#, —C(R)$_2$NRC(R)$_2$-#, —C(R)$_2$C(R)$_2$NRC(R)$_2$-#, —C(O)NRC(R)$_2$-#, —C(R)$_2$C(O)NR-#, —NRC(O)C(R)$_2$-#, —CR$_2$C(O)NRC(R)$_2$-#, —SO$_2$NRC(R)$_2$-#, and —C(R)$_2$NRSO$_2$-#, wherein # represents the point of attachment to Het$^4$.

4. The compound according to any one of the preceding embodiments, wherein L is selected from the group consisting of —C(R)$_2$NRC(O)-#, —C(R)$_2$C(O)NRC(R)$_2$-#, —C(R)$_2$NRC(R)$_2$-#, —C(R)$_2$C(R)$_2$NRC(R)$_2$-#, —C(O)NRC(R)$_2$-#, —C(R)$_2$C(O)NR-#, —CR$_2$C(O)NRC(R)$_2$-#, —SO$_2$NRC(R)$_2$-#, and —C(R)$_2$NRSO$_2$-#, wherein # represents the point of attachment to Het$^4$.

5. The compound according to any one of the preceding embodiments, wherein L is selected from the group consisting of —C(R)$_2$C(O)NRC(R)$_2$-#, —C(R)$_2$NRC(R)$_2$-#, —C(R)$_2$C(R)$_2$NRC(R)$_2$-#, —C(O)NRC(R)$_2$-#, —C(R)$_2$C(O)NRC(R)$_2$-#, —SO$_2$NRC(R)$_2$-#, and —C(R)$_2$NRSO$_2$-#, wherein # represents the point of attachment to Het$^4$.

6. The compound according to any one of the preceding embodiments, wherein L is other than —C(R)$_2$NRC(O)-# or —C(R)$_2$C(O)NR-#.

7. The compound according to any one of the preceding embodiments, wherein L is other than —CH$_2$NRC(O)-# or —CH$_2$C(O)NR-#.

8. The compound according to any one of the preceding embodiments, wherein when L is —C(R)$_2$NRC(O)-# or —C(R)$_2$C(O)NR-#, one of the following (a), (b), or (c) applies:
 (a) n is 0;
 (b) at least one of $R^5$, $R^6$, $R^7$, $R^8$, and $R^9$ is CN; or
 (c) $R^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

9. The compound according to any one of the preceding embodiments, wherein when L is —C(R)$_2$NRC(O)-# or —C(R)$_2$C(O)NR-#, n is 0.

10. The compound according to any one of the preceding embodiments, wherein when L is —C(R)$_2$NRC(O)-# or —C(R)$_2$C(O)NR-#, R' is taken together with a monocyclic Het$^4$ to form an optionally substituted fused 7- to 10-membered saturated or partially unsaturated bicyclic heterocyclylene having 1-4 heteroatoms selected from oxygen, nitrogen, or sulfur.

11. The compound according to any one of the preceding embodiments, wherein when L is —CH$_2$NRC(O)-# or —CH$_2$C(O)NR-#, R' is taken together with a monocyclic Het$^4$ to form an optionally substituted fused 7- to 10-membered saturated or partially unsaturated bicyclic heterocyclylene having 1-4 heteroatoms selected from oxygen, nitrogen, or sulfur.

12. The compound according to any one of the preceding embodiments, wherein when L is —(CR$_2$)$_m$NRC(O)— and m is 0, 1, or 2, then n is 0.

13. The compound according to any one of the preceding embodiments, wherein when L is —(CR$_2$)$_m$NRC(O)— and m is 0 to 2 (e.g., 0 or 2), R' is taken together with a monocyclic Het$^4$ to form an optionally substituted fused 7- to 10-membered saturated or partially unsaturated bicyclic heterocyclylene having 1-4 heteroatoms selected from oxygen, nitrogen, or sulfur.

14. The compound according to any one of the preceding embodiments, wherein L is —C(R)$_2$C(O)NRC(R)$_2$-#, wherein each R is independently hydrogen or C$_{1-3}$ aliphatic optionally substituted with halogen.

15. The compound according to any one of the preceding embodiments, wherein L is —CH$_2$C(O)NHCH(CF$_3$)-#.

16. The compound according to any one of the preceding embodiments, wherein L is —CH$_2$C(O)NHCH(CH$_3$)-#.

17. The compound according to any one of the preceding embodiments, wherein L is —C(R)$_2$NRC(R)$_2$-#, wherein each R is independently hydrogen or C$_{1-3}$ aliphatic optionally substituted with halogen.

18. The compound according to any one of the preceding embodiments, wherein L is —CH$_2$NHCH(CF$_3$)-#.

19. The compound according to any one of the preceding embodiments, wherein L is —CH$_2$NHCH$_2$-#.

20. The compound according to any one of the preceding embodiments, wherein L is —CH$_2$NHCH(CH$_3$)-#.

21. The compound according to any one of the preceding embodiments, wherein L is —CH(CF$_3$)NHCH$_2$-#.

22. The compound according to any one of the preceding embodiments, wherein L is —C(R)$_2$NRSO$_2$-#, wherein each R is independently hydrogen or C$_{1-3}$ aliphatic optionally substituted with halogen.

23. The compound according to any one of the preceding embodiments, wherein L is —CH$_2$NHSO$_2$-#.

24. The compound according to any one of the preceding embodiments, wherein L is —SO$_2$NRC(R)$_2$-#, wherein each R is independently hydrogen or C$_{1-3}$ aliphatic optionally substituted with halogen.

25. The compound according to any one of the preceding embodiments, wherein L is —SO$_2$NHCH$_2$-#.

26. The compound according to any one of the preceding embodiments, wherein L is —SO$_2$NHCH(CH$_3$)-#.

27. The compound according to any one of the preceding embodiments, wherein L is —C(O)NRC(R)$_2$-#, wherein each R is independently hydrogen or C$_{1-3}$ aliphatic optionally substituted with halogen.

28. The compound according to any one of the preceding embodiments, wherein L is —C(O)NHCH$_2$-#.

29. The compound according to any one of the preceding embodiments, wherein L is —C(R)$_2$C(O)NRC(R)$_2$-#, wherein each R is independently hydrogen or C$_{1-3}$ aliphatic optionally substituted with halogen.

30. The compound according to any one of the preceding embodiments, wherein L is —CH$_2$C(O)NHCH$_2$-#.

31. The compound according to any one of the preceding embodiments, wherein the compound has a structure of Formula (I-a), Formula (I-b), Formula (I-c), Formula (I-d),

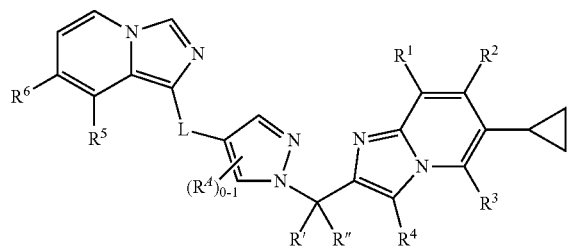
(I-a)

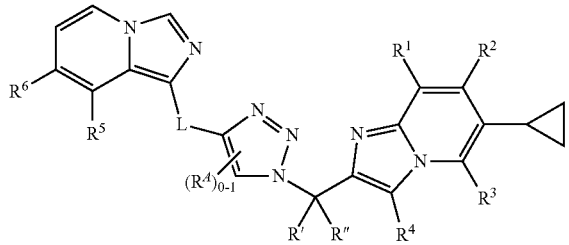
(I-b)

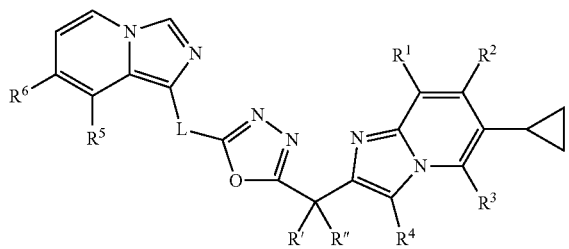
(I-c)

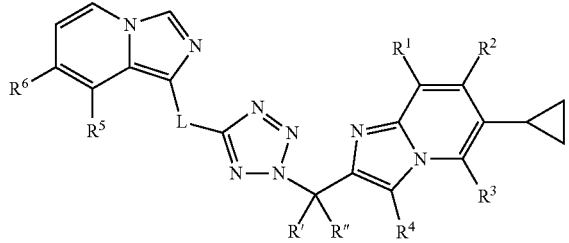
(I-d)

or a pharmaceutically acceptable salt thereof.

32. The compound according to any one of the preceding embodiments, wherein the compound has a structure of Formula (II):

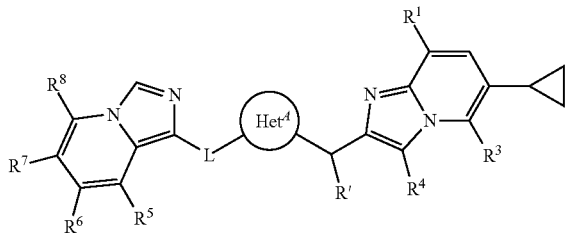
(II)

or a pharmaceutically acceptable salt thereof.

33. The compound according to any one of the preceding embodiments, wherein the compound has a structure of Formula (II-a) or Formula (II-b):

(II-a)

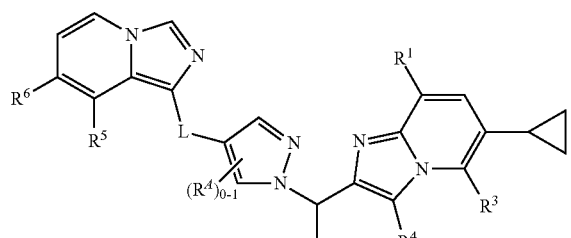

(II-b)

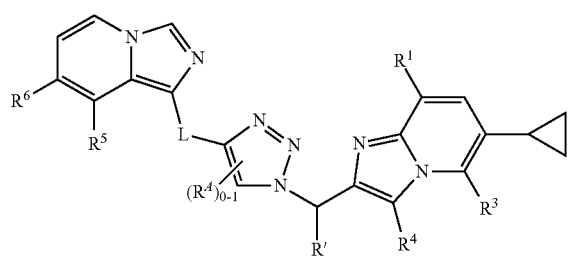

or a pharmaceutically acceptable salt thereof.

34. The compound according to any one of the preceding embodiments, wherein R' is taken together with a monocyclic Het$^4$ to form an optionally substituted fused ring and the compound has a structure of Formula (III):

(III)

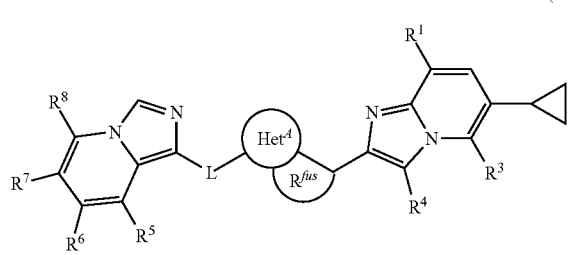

wherein R$^{fus}$ is fused with Het$^4$ to form a fused 7- to 10-membered saturated or partially unsaturated bicyclic heterocyclylene having 1-4 heteroatoms selected from oxygen, nitrogen, or sulfur, or a pharmaceutically acceptable salt thereof.

35. The compound according to any one of the preceding embodiments, wherein the compound has a structure of Formula (III-a) or Formula (III-b):

(III-a)

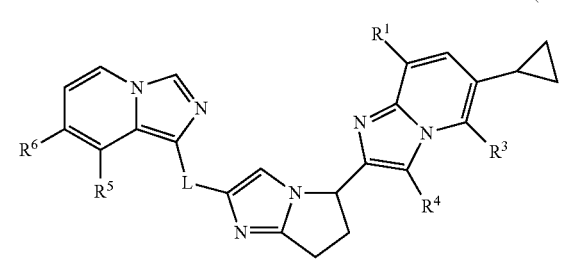

(III-b)

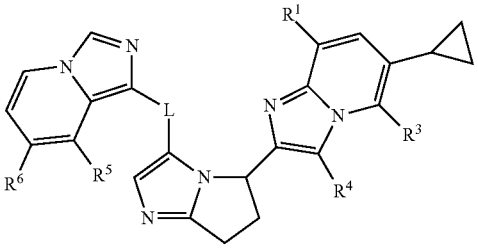

or a pharmaceutically acceptable salt thereof.

36. The compound according to any one of the preceding embodiments, wherein Het$^4$ is a 5-membered monocyclic heteroarylene having 1-4 heteroatoms selected from oxygen, nitrogen, or sulfur, wherein Het$^4$ is substituted with 0-2 R$^4$ groups.

37. The compound according to any one of the preceding embodiments, wherein Het$^4$ is a 5-membered monocyclic heteroarylene having 2-3 heteroatoms selected from nitrogen, wherein Het$^4$ is substituted with 0-2 R$^4$ groups.

38. The compound according to any one of the preceding embodiments, wherein Het$^4$ is pyrazolediyl substituted with 0-2 R$^4$ groups.

39. The compound according to any one of the preceding embodiments, wherein Het$^4$ is triazolediyl substituted with 0-1 R$^4$ groups.

40. The compound according to any one of the preceding embodiments, wherein Het$^4$ is an unsubstituted pyrazolediyl.

41. The compound according to any one of the preceding embodiments, wherein Het$^4$ is an unsubstituted 1,2,3-triazolediyl.

42. The compound according to any one of the preceding embodiments, wherein Het$^4$ is selected from:

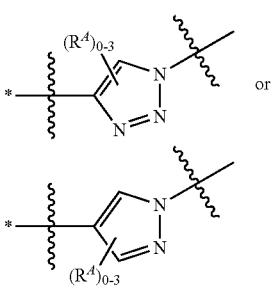

wherein * represents to point of attachment to L.

43. The compound according to any one of the preceding embodiments, wherein a single instance of R$^4$ is C$_{1-6}$ aliphatic substituted with halogen.

44. The compound according to any one of the preceding embodiments, wherein R' and R'' are each hydrogen.

45. The compound according to any one of the preceding embodiments, wherein R'' is hydrogen and R' is taken together with a monocyclic Het$^4$ to form a fused 7- to 10-membered saturated or partially unsaturated bicyclic heterocyclylene having 1-4 heteroatoms selected from oxygen, nitrogen, or sulfur.

46. The compound according to any one of the preceding embodiments, wherein n is 1, R'' is hydrogen and R' is taken together with a monocyclic Het$^4$ to form a fused 7- to 10-membered saturated or partially unsaturated bicyclic heterocyclylene having 1-4 heteroatoms selected from oxygen, nitrogen, or sulfur.
47. The compound according to any one of the preceding embodiments, wherein n is 1, R″ is hydrogen and R′ is taken together with a monocyclic Het$^4$ to form a fused 8-membered saturated or partially unsaturated bicyclic heterocyclylene having 1-4 heteroatoms selected from oxygen, nitrogen, or sulfur.
48. The compound according to any one of the preceding embodiments, wherein when n is 0, Het$^4$ is a 7- to 10-membered saturated or partially unsaturated bicyclic heterocyclylene having 1-4 heteroatoms selected from oxygen, nitrogen, or sulfur.
49. The compound according to any one of the preceding embodiments, wherein n is 0.
50. The compound according to any one of the preceding embodiments, wherein n is 1.
51. The compound according to any one of the preceding embodiments, wherein each of $R^2$, $R^3$, $R^4$, $R^5$, $R^7$, $R^8$, and $R^9$ are hydrogen.
52. The compound according to any one of the preceding embodiments, wherein each of $R^1$, $R^2$, $R^3$, $R^4$, $R^7$, $R^8$, and $R^9$ are hydrogen.
53. The compound according to any one of the preceding embodiments, wherein each of $R^1$, $R^2$, $R^3$, $R^4$, $R^5$, $R^7$, $R^8$, and $R^9$ are hydrogen.
54. The compound according to any one of the preceding embodiments, wherein $R^1$ is an optionally substituted group selected from 5- to 6-membered heteroaryl having 1-4 heteroatoms selected from oxygen, nitrogen, or sulfur, and 3- to 7-membered saturated or partially unsaturated monocyclic heterocyclyl having 1-2 heteroatoms selected from oxygen, nitrogen, or sulfur.
55. The compound according to any one of the preceding embodiments, wherein $R^1$ is an optionally substituted 5-membered heteroaryl having 2-4 heteroatoms selected from oxygen or nitrogen.
56. The compound according to any one of the preceding embodiments, wherein $R^1$ is an optionally substituted piperizinyl or an optionally substituted triazolyl.
57. The compound according to any one of the preceding embodiments, wherein $R^1$ is optionally substituted $C_{1-6}$ aliphatic.
58. The compound according to any one of the preceding embodiments, wherein substituents on an optionally substituted $R^1$ group are independently halogen, —$(CH_2)_{0-4}R^o$, —$(CH_2)_{0-4}OR^o$; and —$(CH_2)_{0-4}C(O)OR^o$, wherein each $R^o$ is independently hydrogen, $C_{1-6}$ aliphatic, or a 5-6 membered saturated, partially unsaturated, or aryl ring having 0-4 heteroatoms independently selected from nitrogen, oxygen, or sulfur.
59. The compound according to any one of the preceding embodiments, wherein $R^5$ and $R^6$ are each independently halogen.
60. The compound according to any one of the preceding embodiments, wherein $R^5$ is F and $R^6$ is Cl.
61. The compound according to any one of the preceding embodiments, wherein $R^6$ is Cl or CN.
62. The compound of any one of the preceding embodiments, wherein the compound is any one of compounds I-1 through I-20, or a pharmaceutically acceptable salt thereof.
63. A pharmaceutical composition comprising a compound of any one of the preceding embodiments.
64. The pharmaceutical composition comprising a compound of any one of the preceding embodiments, further comprising a pharmaceutically acceptable excipient.
65. The pharmaceutical composition of any one of embodiments 63-64, wherein the composition is suitable for oral administration.
66. The pharmaceutical composition of any one of embodiments 63-64, wherein the composition is suitable for administration by injection.
67. A method of treating a plasma kallikrein-mediated disease or disorder using a compound or composition of any one of the preceding embodiments.
68. The method of embodiment 67, wherein the disease or disorder is hereditary angioedema or diabetic macular edema.
69. A method of treating hereditary angioedema or diabetic macular edema comprising administering to a patient in need thereof a compound or composition of any one of the preceding embodiments.

Exemplification

Synthesis of Intermediates

Synthesis of 2-(7-chloroimidazo[1,5-α]pyridin-1-yl)acetic acid

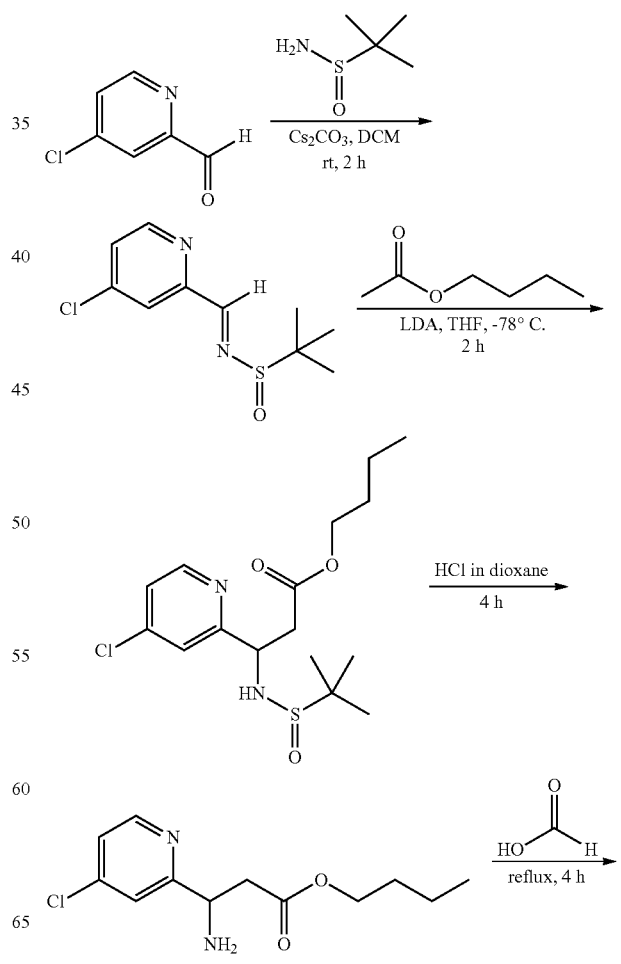

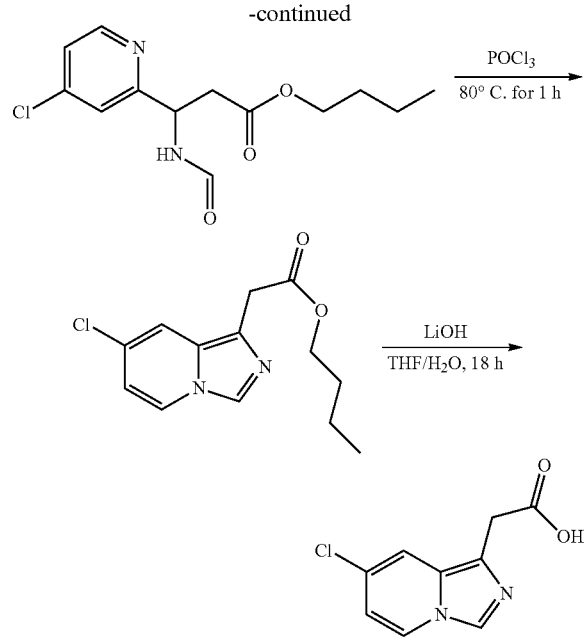

Synthesis of N-((4-chloropyridin-2-yl)methylene)-2-methylpropane-2-sulfinamide. To a stirred suspension of (S)-2-methylpropane-2-sulfinamide (5.00 g, 41.3 mmol) and cesium carbonate (20.2 g, 61.9 mmol) in dichloromethane (100 mL) was added a solution of 4-chloropicolinaldehyde (5.84 g, 41.3 mmol) in dichloromethane (20 mL) dropwise over a period of 10 min at room temperature. The solution was stirred for 2 h. The reaction mixture was diluted with water (100 mL) and extracted with dichloromethane (100 mL×3). The combined organic layers were dried (MgSO$_4$) and concentrated to give the product (N-((4-chloropyridin-2-yl) methylene)-2-methylpropane-2-sulfinamide, 10.1 g, quant.) as a brown oil. LCMS RT=1.738 min [M+H]$^+$ 246.9, 95% purity.

Synthesis of 3-((tert-butylsulfinyl)amino)-3-(4-chloropyridin-2-yl)propanoate. To a stirred solution of lithium diisopropylamide (2M in tetrahydrofuran, 43 mL, 86 mmol) in anhydrous tetrahydrofuran (100 mL), was added dropwise a solution of butyl acetate (9.40 g, 81 mmol) in tetrahydrofuran (20 mL) at −78° C. under nitrogen atmosphere. After stirring for 30 min, a solution of N-((4-chloropyridin-2-yl)methylene)-2-methylpropane-2-sulfinamide (10.0 g, 41 mmol) in tetrahydrofuran (30 mL) was added at this temperature. After stirring for an additional 2 h at −78° C., the reaction mixture was quenched with saturated aqueous ammonium chloride (100 mL) and warmed to room temperature. The organic layer was separated and the aqueous layer was extracted with ethyl acetate (100 mL×3). The combined organic layers were dried (Na$_2$SO$_4$), concentrated and purified by flash chromatography (eluent 50% petroleum ether/ethyl acetate) to give the product (butyl 3-((tert-butylsulfinyl)amino)-3-(4-chloropyridin-2-yl)propanoate, 9.0 g, 61%) as a white solid. LCMS RT=1.338 min [M+H]$^+$ 361, 95% purity.

Synthesis of butyl 3-amino-3-(4-chloropyridin-2-yl)propanoate. To a solution of butyl 3-(4-chloropyridin-2-yl)-3-(1,1-dimethylethylsulfinamido)propanoate (3.5 g, 9.7 mmol) in 1,4-dioxane (30 mL) was added a solution of hydrochloric acid (4 M in 1,4-dioxane, 10 mL, 40 mmol). The mixture was stirred at room temperature for 4 h then concentrated to give the crude oil (4.3 g) which was used into next step without purification. LCMS RT=1.187 min [M+H]$^+$ 257, 80% purity.

Synthesis of butyl 3-(4-chloropyridin-2-yl)-3-formamidopropanoate. A solution of butyl 3-amino-3-(4-chloropyridin-2-yl)propanoate (2.6 g, 10.2 mmol) in formic acid (10 mL) was stirred at reflux for 4 h. The reaction mixture was then concentrated to give the crude product as a dark oil (3.0 g) which was used in the next step without purification. LCMS RT=1.05 min [M+H]$^+$ 285, 83% purity Synthesis of butyl 2-(7-chloroimidazo[1,5-a]pyridin-1-yl) acetate. A solution of butyl 3-(4-chloropyridin-2-yl)-3-formamidopropanoate (500 mg, 1.76 mmol) in phosphorus(V) oxychloride (5.0 mL) was stirred at 80° C. for 1 h. The mixture was evaporated, the residue was dissolved in ethyl acetate (100 mL) and washed with saturated aqueous sodium bicarbonate solution (50 mL). The organic layer was separated and the aqueous layer was extracted again with ethyl acetate (50 mL×3). The combined organic layers were concentrated and purified by flash chromatography (eluent 70% ethyl acetate/petroleum ether) to give the product (butyl 2-(7-chloroimidazo[1,5-a]pyridin-1-yl)acetate, 290 mg, 62%). LCMS RT=1.18 min [M+H]$^+$ 267, 95% purity.

Synthesis of 2-(7-chloroimidazo[1,5-a]pyridin-1-yl)acetic acid. To a stirred solution of butyl 2-(7-chloroimidazo[1,5-α]pyridin-1-yl)acetate (310 mg, 1.16 mmol) in tetrahydrofuran (3 mL) and water (1 mL) was added lithium hydroxide (139 mg, 5.8 mmol) and the mixture was stirred at room temperature for 16 h. The pH was adjusted to 6 by adding aqueous 1M hydrochloric acid and extracted with dichloromethane/methanol (10/1, 50 mL×5). Combined organic layers were dried and concentrated to give the product (2-(7-chloroimidazo[1,5-α]pyridin-1-yl)acetic acid, 200 mg, 82%) which was used in the next step without purification. LCMS RT=0.901 min [M+H]$^+$ 211, 95% purity Synthesis of methyl 2-(7-chloroimidazo[1,5-a]pyridin-1-yl)acetate

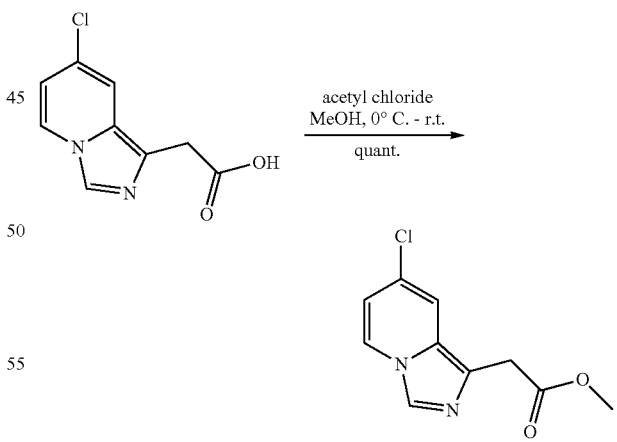

Acetyl chloride (0.42 mL, 5.9 mmol) was added to a stirred solution of 2-(7-chloroimidazo[1,5-α]pyridin-1-yl) acetic acid (250 mg, 1.2 mmol) in methanol (5.0 mL) at 0° C. then warmed to room temperature and stirred for 18 h. The mixture was concentrated in vacuo. The residue was dissolved in a mixture of saturated aqueous sodium bicarbonate solution (25 mL) and water (25 mL) and extracted with methanol/dichloromethane (1:9, 3×50 mL). The combined organic layers were dried (MgSO$_4$), filtered and evaporated in vacuo to yield the product (methyl 2-(7-chloroimidazo[1,5-α]pyridin-1-yl)acetate, 310 mg, quant.) as a cream solid.

$^1$H NMR (400 MHz, DMSO): δ, ppm 9.23 (1H, s), 8.52 (1H, dd, J=1.0, 7.5 Hz), 8.08-8.07 (1H, m), 7.03 (1H, dd, J=2.0, 7.5 Hz), 4.17 (2H, s), 3.67 (3H, s).

Synthesis of 2-(7-chloroimidazo[1,5-α]pyridin-1-yl)acetamide

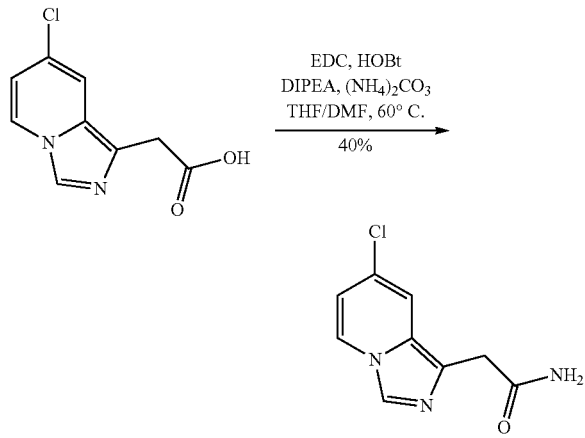

A mixture of 2-(7-chloroimidazo[1,5-α]pyridin-1-yl)acetic acid (500 mg, 2.4 mmol), N-(3-dimethylaminopropyl)-N'-ethylcarbodiimide hydrochloride (550 mg, 2.9 mmol), 1-hydroxybenzotriazole hydrate (380 mg, 2.9 mmol), N,N-diisopropylethylamine (2.5 mL, 14 mmol) and ammonium carbonate (1.1 g, 12 mmol) in tetrahydrofuran (7.0 mL) and N,N-dimethylformamide (4.0 mL) was stirred at 60° C. for 18 h. The mixture was cooled, diluted with water (50 mL) and extracted with ethyl acetate (3×50 mL). The combined organic layers were washed with saturated aqueous sodium carbonate solution (100 mL), dried (MgSO$_4$), filtered and evaporated in vacuo. The residue was triturated with diethyl ether:dichloromethane (9:1) to give the product (2-(7-chloroimidazo[1,5-α]pyridin-1-yl)acetamide, 0.20 g, 40%) as a yellow solid.

$^1$H NMR (400 MHz, DMSO): δ, ppm 8.36-8.33 (2H, m), 7.79-7.77 (1H, m), 7.45-7.38 (1H, m), 6.99-6.92 (1H, m), 6.68 (1H, dd, J=2.0, 7.3 Hz), 3.66 (2H, s).

Synthesis of ethyl 1-((6-cyclopropylimidazo[1,2-a]pyridin-2-yl)methyl)-1H-1,2,3-triazole-4-carboxylate Synthesis of 5-cyclopropylpyridin-2-amine. A mixture of 5-bromopyridin-2-amine (100 g, 585 mmol), cyclopropylboronic acid (60 g, 701 mmol), Pd(AcO)$_2$ (6.5 g, 29 mmol), SPhos (24 g, 58.5 mmol) and K$_3$PO$_4$ (372 g, 1.755 mol) in toluene/H$_2$O (1.2 L/0.12 L) was stirred at 90° C. for 14 h under N$_2$. The reaction was concentrated in vacuo to give the crude, which was purified with silica gel chromatography (PE/EA=1/2) to give the 5-cyclopropylpyridin-2-amine (61 g, yield: 78%) as a yellow solid. ESI-MS [M+H]+: 135.1.

Synthesis of 2-(chloromethyl)-6-cyclopropylimidazo[1,2-a]pyridine. A mixture of 5-cyclopropylpyridin-2-amine (61 g, 455 mmol) and 1,3-dichloropropan-2-one (172 g, 1365 mmol) in EtOH (1 L) was stirred at 95° C. for 13 h. The reaction was concentrated to remove the EtOH. The pH of the residue was adjusted to 9 by addition of aqueous NaHCO$_3$ and extracted with EtOAc (1 L×3). The combined organic layers were washed with brine, dried over Na$_2$SO$_4$ and concentrated in vacuo to give the crude, which was purified with silica gel chromatography (EA) to give the 2-(chloromethyl)-6-cyclopropylimidazo[1,2-a]pyridine (40 g, yield: 42%) as a yellow solid. ESI-MS [M+H]+: 207.1.

Synthesis of 2-(azidomethyl)-6-cyclopropylimidazo[1,2-a]pyridine. To a solution of 2-(chloromethyl)-6-cyclopropylimidazo[1,2-a]pyridine (40 g, 193 mmol) in DMF (600 mL) was added NaN$_3$ (18.8 g, 290 mmol). The resulting reaction was stirred at RT for 2 h. The reaction was diluted with H$_2$O (500 mL) and extracted with EtOAc (500 mL×3). The combined organic layers were washed with brine, dried over Na$_2$SO$_4$ and concentrated in vacuo to give the crude, which was purified with silica gel chromatography (PE/EA=2/1) to give the 2-(azidomethyl)-6-cyclopropylimidazo[1,2-a]pyridine (35 g, yield: 85%) as a yellow solid. ESI-MS [M+H]+: 214.1.

Synthesis of ethyl 1-((6-cyclopropylimidazo[1,2-a]pyridin-2-yl)methyl)-1H-1,2,3-triazole-4-carboxylate. A mixture of 2-(azidomethyl)-6-cyclopropylimidazo[1,2-a]pyridine (35 g, 163.5 mmol), ethyl propiolate (17.6 g, 180 mmol), CuSO$_4$ (2.6 g, 16.35 mmol) and sodium ascorbate (3.3 g, 16.35 mmol) in H$_2$O/t-BuOH (150 mL/150 mL) was stirred at RT for 3 h. Yellow solid was precipitated after 3 h and the mixture was filtered. The cake was dried to give the ethyl 1-((6-cyclopropylimidazo[1,2-a]pyridin-2-yl)methyl)-1H-1,2,3-triazole-4-carboxylate (29 g, yield: 57%) as a yellow solid, which was used in the next step without further purification. ESI-MS [M+H]+: 312.1.

Synthesis of 7-chloro-8-fluoroimidazo[1,5-a]pyridine-1-carbaldehyde

Synthesis of 4-chloro-3-fluoropicolinaldehyde. To a solution of 2, 2, 6, 6-tetramethylpiperidine (35.4 g, 250.88 mmol) in 200 mL THF was added n-Butyllithium (2.4 M in hexane, 100 mL, 240 mmol) dropwise at 0° C. The reaction mixture was cooled to −78° C. after stirring at 0° C. for 1h and a solution of 4-chloro-3-fluoropyridine (30.0 g, 228.08 mmol) in THF (100 mL) was added dropwise. The resulting reaction mixture was stirred at −78° C. for 2 h, a solution of DMF (17.5 g, 239.48 mmol) in THF (50 mL) was added dropwise, and the resulting reaction mixture was stirred at −78° C. for another 1 h. The reaction was quenched with H$_2$O (50 mL), and extracted with ethyl acetate (200 mL×3). The combined organic layers were washed with brine, dried over with anhydrous magnesium sulphate, filtered, and concentrated. The residue was purified by silica gel column chromatography (petroleum ether/ethyl acetate=3/1) to afford 4-chloro-3-fluoropicolinaldehyde (26.0 g, yield: 71%). ESI-MS [M+H]+: 160.1.

Synthesis of N-((4-chloro-3-fluoropyridin-2-yl)methyl)-2-methylpropane-2-sulfinamide. To a solution of 4-chloro-3-fluoropicolinaldehyde (26.0 g, mixture, 163.0 mmol) in DCM (100 mL) was added cesium carbonate (96.0 g, 293.3 mmol) and 2-methylpropane-2-sulfinamide (19.8 g, 163.0 mmol) at RT. The reaction mixture was stirred for 3 h at RT. After the reaction was complete, the reaction mixture was filtrated and washed with DCM three times. To the combined mixture was added MeOH (40 mL), and then the resulting mixture was cooled to 0° C. by ice-water bath. Sodium borohydride (15.5 g, 409.0 mmol) was added slowly in portions. The reaction mixture was warmed up to RT and stirred at this temperature for 2 h. The reaction was quenched with H$_2$O carefully. The resulting mixture was extracted with DCM (100 mL×3), the combined organic solvent was dried by sodium sulfate, filtered, and concentrated to get crude N-((4-chloro-3-fluoropyridin-2-yl)methyl)-2-methylpropane-2-sulfinamide (43.3 g, crude) as yellow solid. ESI-MS [M+H]$^+$: 265.1.

Synthesis of (4-chloro-3-fluoropyridin-2-yl)methanamine hydrochloride. To a solution of N-((4-chloro-3-fluoropyridin-2-yl)methyl)-2-methylpropane-2-sulfinamide (about 162.4 mmol) in ethyl acetate (100 mL) was added a solution of hydrochloride acid in ethyl acetate (3 M, 200 mL). The resulting reaction mixture was stirred at RT for 3 h. After the reaction was completed, the reaction mixture was filtered to give the crude product, which was washed with ethyl acetate and dried in vacuum to afford (4-chloro-3-fluoropyridin-2-yl)methanamine hydrochloride (25.0 g, 78%, mixture) as a pink solid. $^1$H NMR (400 MHz, DMSO) δ 8.75 (br, 3H), 8.47 (d, J=5.2 Hz, 1H), 7.80 (t, J=5.6 Hz, 1H), 4.28-4.26 (m, 2H).

Synthesis of N-((4-chloro-3-fluoropyridin-2-yl)methyl)formamide. To a solution of (4-chloro-3-fluoropyridin-2-yl)methanamine hydrochloride (25.0 g, mixture, 127.0 mmol) in THF (200 mL) was added triethylamine (38.5 g, 380.6 mmol) and ethyl formate (100 mL) at RT. The resulting reaction mixture was stirred at 70° C. overnight. After the reaction was complete, the reaction mixture was filtered, the solid was washed with DCM three times. The combined organic solvent was washed with brine, dried by sodium sulfate, filtrated, and concentrated to afford N-((4-chloro-3-fluoropyridin-2-yl)methyl)formamide (crude), which was used in the next step directly without purification. ESI-MS [M+H]$^+$: 189.1.

Synthesis of 7-chloro-8-fluoroimidazo[1,5-a]pyridine. To a solution of N-((4-chloro-3-fluoropyridin-2-yl)methyl)formamide (crude, about 126.89 mmol) in dry acetonitrile (200 mL) was added phosphoryl trichloride (18 mL, 1.5 eq), and the resulting reaction mixture was stirred at reflux for 3 h. After the reaction was completed, the reaction mixture was cooled down to RT, and then poured into H$_2$O (200 mL) carefully. The pH was adjusted to 8 with saturated sodium bicarbonate, and then the resulting mixture was extracted with ethyl acetate (200 mL×3). The combined organic phase was washed with brine, dried over sodium sulphate, filtrated, and concentrated in vacuo. The residue was purified by silica gel chromatography (ethyl acetate) to afford 7-chloroimidazo[1,5-a]pyridine (12.0 g, yield: 56%) as a white solid. ESI-MS [M+H]$^+$: 171.1.

Synthesis of 7-chloro-8-fluoroimidazo[1,5-a]pyridine-1-carbaldehyde. A solution of 7-chloro-8-fluoroimidazo[1,5-a]pyridine (9.0 g, 52.6 mmol) in dry DMF (12 mL) was cooled with an ice-water bath to 0-5° C. Phosphorus oxychloride (7.4 g, 78.9 mmol, 1.5 eq) was added dropwise, and then the reaction mixture was stirred at 100° C. for 2 h. After the reaction was completed, the reaction mixture was cooled down to RT and poured into saturated sodium bicarbonate aqueous (200 mL) carefully. The resulting mixture was stirred at RT for 2 h and extracted with ethyl acetate (3×200 mL). The combined organic phase was washed with brine, dried over sodium sulphate, filtered, and concentrated in vacuo. The residue was purified by recrystallization (petroleum ether/ethyl acetate=1/1) to afford 7-chloroimidazo[1,5-a]pyridine-1-carbaldehyde (5.2 g, yield: 47%) as a brown solid. ESI-MS [M+H]$^+$: 181.1.

Synthesis of 1-((6-cyclopropylimidazo[1,2-a]pyridin-2-yl)methyl)-1H-pyrazole-4-carboxylic acid Synthesis of 5-cyclopropylpyridin-2-amine. A solution of 5-bromopyridin-2-amine (5 g, 29.1 mmol), cyclopropylboronic acid (3.75 g, 43.6 mmol), Pd(OAc)$_2$ (651 mg, 2.91 mmol), SPhos (1.19 g, 2.91 mmol) and K$_3$PO$_4$ (18.5 g, 87.3 mmol) in toluene/H$_2$O (100 mL/10 mL) was stirred at 95° C. for 12 h under nitrogen. Then the reaction mixture was quenched with H$_2$O (50 mL) and extracted with DCM (200 mL). The combined organic layers were dried over Na$_2$SO$_4$ and concentrated in vacuo to give the crude residue which was purified by silica gel chromatography (PE/EtOAc=1/1) to give the 5-cyclopropylpyridin-2-amine as yellow solid (3.8 g, 97.4% yield). ESI-MS [M+H]$^+$: 135.2.

Synthesis of 2-(chloromethyl)-6-cyclopropylimidazo[1,2-a]pyridine. To a solution 5-cyclopropyl-4-methylpyridin-2-amine (500 mg, 3.70 mmol) in DMF (10 mL) was added 1,3-dichloropropan-2-one (1409 mg, 11.1 mmol) at RT. The resulting reaction was stirred at 85° C. for 2 h. The solution was quenched with H$_2$O (60 mL), adjusted to pH 8 by adding saturated NaHCO$_3$ solution, and extracted with EtOAc (50 mL×3). The combined organic layers were washed with brine, dried over Na$_2$SO$_4$, and concentrated in vacuo to give the crude, which was purified with prep-TLC (PE/EtOAc=1/1) to give the 2-(chloromethyl)-6-cyclopropyl-7-methylimidazo[1,2-a]pyridine (300 mg, yield: 39%) as a light yellow oil. ESI-MS [M+H]$^+$: 207.2.

Synthesis of ethyl 1-((6-cyclopropylimidazo[1,2-a]pyridin-2-yl)methyl)-1H-pyrazole-4-carboxylate. To a solution 2-(chloromethyl)-6-cyclopropylimidazo[1,2-a]pyridine (2 g, 9.70 mmol) in DMF (20 mL) was added ethyl 1H-pyrazole-4-carboxylate (906 mg, 6.46 mmol) and Cs$_2$CO$_3$ (6.32 g, 19.38 mmol) at RT. The resulting reaction was stirred at RT for 12 h. H$_2$O (150 mL) was added to the reaction and then the mixture was extracted with EtOAc (100 mL×3). The combined organic layers were washed with brine, dried over Na$_2$SO$_4$, concentrated in vacuo to give the crude, which was purified with silica gel chromatography (DCM/MeOH=20/1) to give the ethyl 1-((6-cyclopropylimidazo[1,2-a]pyridin-2-yl)methyl)-1H-pyrazole-4-carboxylate (1.5 g, yield: 75%) as a white solid. ESI-MS [M+H]$^+$: 311.2.

Synthesis of 1-((6-cyclopropylimidazo[1,2-a]pyridin-2-yl)methyl)-1H-pyrazole-4-carboxylic acid. To a solution of ethyl 1-((6-cyclopropylimidazo[1,2-a]pyridin-2-yl)methyl)-1H-pyrazole-4-carboxylate (1.2 g, 3.87 mmol) in THF (20 mL) and H$_2$O (10 mL) was added LiGH (464 mg, 19.35 mmol). The mixture was stirred at RT for 16 h. Most of the THF was removed and the pH was adjusted to 4-5 by adding HCl (1 M). The resulting precipitate was collected and dried to give the 1-((6-cyclopropylimidazo [1,2-a]pyridin-2-yl)methyl)-1H-pyrazole-4-carboxylic acid as a white solid (1.0 g, yield: 91%). ESI-MS [M+H]$^+$: 283.2.

Synthesis of 1-(aminomethyl)imidazo[1,5-a]pyridine-7-carbonitrile

Synthesis of tert-butyl ((7-bromoimidazo[1,5-a]pyridin-1-yl)methyl)carbamate. To a solution of (7-bromoimidazo[1,5-a]pyridin-1-yl)methanamine hydrochloride salt (2 g, 7.66 mmol) in DCM (30 mL) was added triethylamine (4.3 mL, 30.6 mmol) and di-tert-butyl dicarbonate (3.5 mL, 15.3 mmol). The mixture was stirred at RT for 2 h. TLC showed that the reaction was completed. The mixture was concentrated, dissolved in ethyl acetate, washed with saturated ammonium chloride. The organic layer was concentrated, purified by column chromatography (DCM/MeOH=10/1) to give tert-butyl ((7-bromoimidazo[1,5-a]pyridin-1-yl)methyl)carbamate (2 g, yield: 80%) as a yellow oil. ESI-MS [M+H]$^+$: 326.1.

Synthesis of tert-butyl ((7-cyanoimidazo[1,5-a]pyridin-1-yl)methyl)carbamate. To a solution of tert-butyl ((7-bromoimidazo[1,5-a]pyridin-1-yl)methyl)carbamate (200 mg, 0.615 mmol) in DMF (3 mL) was added 1,1'-bis(diphenylphosphino)ferrocene (64 mg, 0.12 mmol), tris(dibenzylideneacetone)dipalladium ($Pd_2(dba)_3$, 55 mg, 0.06 mmol) and zinc cyanide (144 mg, 1.23 mmol). The mixture was stirred at 150° C. in microwave reactor for 1 h and concentrated. The residue was purified by column chromatography (DCM/MeOH=10/1) to give tert-butyl ((7-cyanoimidazo[1,5-a]pyridin-1-yl)methyl)carbamate (117 mg, yield: 70%) as a yellow oil. ESI-MS $[M+H]^+$: 273.1.

Synthesis of 1-(aminomethyl)imidazo[1,5-a]pyridine-7-carbonitrile. A mixture of tert-butyl ((7-cyanoimidazo[1,5-a]pyridin-1-yl)methyl)carbamate (270 mg, 0.99 mmol) and hydrochloride in ethyl acetate (3 M, 20 mL) was stirred at RT for 2 h and then filtered to give the crude product which was washed with ethyl acetate and dried in vacuum to afford 1-(aminomethyl)imidazo[1,5-a]pyridine-7-carbonitrile (201.3 mg, quant.) as a yellow solid. ESI-MS $[M-NH_2]^+$: 156.0. Purity: 96.3%.

Synthesis of Ethyl 1-((6-cyclopropylimidazo[1,2-a]pyridin-2-yl)methyl)-1H-1,2,3-triazole-4-carboxylate Synthesis of 5-cyclopropylpyridin-2-amine. A mixture of 5-bromopyridin-2-amine (100 g, 585 mmol), cyclopropylboronic acid (60 g, 701 mmol), $Pd(AcO)_2$ (6.5 g, 29 mmol), SPhos (24 g, 58.5 mmol) and $K_3PO_4$ (372 g, 1.755 mol) in toluene/$H_2O$ (1.2 L/0.12 L) was stirred at 90° C. for 14 h under $N_2$. The reaction was concentrated in vacuo to give the crude, which was purified with silica gel chromatography (PE/EA=1/2) to give the 5-cyclopropylpyridin-2-amine (61 g, yield: 78%) as a yellow solid. ESI-MS $[M+H]^+$: 135.1.

Synthesis of 2-(chloromethyl)-6-cyclopropylimidazo[1,2-a]pyridine. A mixture of 5-cyclopropylpyridin-2-amine (61 g, 455 mmol) and 1,3-dichloropropan-2-one (172 g, 1365 mmol) in EtOH (1 L) was stirred at 95° C. for 13 h. The reaction was concentrated to remove the EtOH. The pH of the residue was adjusted to 9 by addition of aqueous $NaHCO_3$ and extracted with EtOAc (1 L×3). The combined organic layers were washed with brine, dried over $Na_2SO_4$ and concentrated in vacuo to give the crude, which was purified with silica gel chromatography (EA) to give the 2-(chloromethyl)-6-cyclopropylimidazo[1,2-a]pyridine (40 g, yield: 42%) as a yellow solid. ESI-MS $[M+H]^+$: 207.1.

Synthesis of 2-(azidomethyl)-6-cyclopropylimidazo[1,2-a]pyridine. To a solution of 2-(chloromethyl)-6-cyclopropylimidazo[1,2-a]pyridine (40 g, 193 mmol) in DMF (600 mL) was added $NaN_3$ (18.8 g, 290 mmol). The resulting reaction was stirred at RT for 2 h. The reaction was diluted with $H_2O$ (500 mL) and extracted with EtOAc (500 mL×3). The combined organic layers were washed with brine, dried over $Na_2SO_4$ and concentrated in vacuo to give the crude, which was purified with silica gel chromatography (PE/EA=2/1) to give the 2-(azidomethyl)-6-cyclopropylimidazo[1,2-a]pyridine (35 g, yield: 85%) as a yellow solid. ESI-MS $[M+H]^+$: 214.1.

Synthesis of ethyl 1-((6-cyclopropylimidazo[1,2-a]pyridin-2-yl)methyl)-1H-1,2,3-triazole-4-carboxylate. A mixture of 2-(azidomethyl)-6-cyclopropylimidazo[1,2-a]pyridine (35 g, 163.5 mmol), ethyl propiolate (17.6 g, 180 mmol), $CuSO_4$ (2.6 g, 16.35 mmol) and sodium ascorbate (3.3 g, 16.35 mmol) in $H_2O$/t-BuOH (150 mL/150 mL) was stirred at RT for 3 h. Yellow solid was precipitated after 3 h and the mixture was filtered. The cake was dried to give the ethyl 1-((6-cyclopropylimidazo[1,2-a]pyridin-2-yl)methyl)-1H-1,2,3-triazole-4-carboxylate (29 g, yield: 57%) as a yellow solid, which was used in the next step without further purification. ESI-MS $[M+H]^+$: 312.1.

Synthesis of (7-chloro-8-fluoroimidazo[1,5-a]pyridin-1-yl)methanamine hydrochloride Synthesis of 4-chloro-3-fluoropicolinaldehyde. To a solution of 2, 2, 6, 6-tetramethylpiperidine (35.4 g, 250.88 mmol) in 200 mL THF was added n-Butyllithium (2.4 M in hexane, 100 mL, 240 mmol) dropwise at 0° C. The reaction mixture was cooled to −78° C. after stirring at 0° C. for 1h and a solution of 4-chloro-3-fluoropyridine (30.0 g, 228.08 mmol) in THF (100 mL) was added dropwise. The resulting reaction mixture was stirred at −78° C. for 2 h, a solution of DMF (17.5 g, 239.48 mmol) in THF (50 mL) was added dropwise, and the resulting reaction mixture was stirred at −78° C. for another 1 h. The reaction was quenched with $H_2O$ (50 mL), and extracted with ethyl acetate (200 mL×3). The combined organic layers were washed with brine, dried over with anhydrous magnesium sulphate, filtered, and concentrated. The residue was purified by silica gel column chromatography (petroleum ether/ethyl acetate=3/1) to afford 4-chloro-3-fluoropicolinaldehyde (26.0 g, yield: 71%). ESI-MS $[M+H]^+$: 160.1.

Synthesis of N-((4-chloro-3-fluoropyridin-2-yl)methyl)-2-methylpropane-2-sulfinamide. To a solution of 4-chloro-3-fluoropicolinaldehyde (26.0 g, mixtutre, 163.0 mmol) in DCM (100 mL) was added cesium carbonate (96.0 g, 293.3 mmol) and 2-methylpropane-2-sulfinamide (19.8 g, 163.0 mmol) at RT. The reaction mixture was stirred for 3 h at RT. After the reaction was complete, the reaction mixture was filtrated and washed with DCM three times. To the combined mixture was added MeOH (40 mL), and then the resulting mixture was cooled to 0° C. by ice-water bath. Sodium borohydride (15.5 g, 409.0 mmol) was added slowly in portions. The reaction mixture was warmed up to RT and stirred at this temperature for 2 h. The reaction was quenched with $H_2O$ carefully. The resulting mixture was extracted with DCM (100 mL×3), the combined organic solvent was dried by sodium sulfate, filtered, and concentrated to get crude N-((4-chloro-3-fluoropyridin-2-yl)methyl)-2-methylpropane-2-sulfinamide (43.3 g, crude) as yellow solid. ESI-MS $[M+H]^+$: 265.1.

Synthesis of (4-chloro-3-fluoropyridin-2-yl)methanamine hydrochloride. To a solution of N-((4-chloro-3-fluoropyridin-2-yl)methyl)-2-methylpropane-2-sulfinamide (about 162.4 mmol) in ethyl acetate (100 mL) was added a solution of hydrochloride acid in ethyl acetate (3 M, 200 mL). The resulting reaction mixture was stirred at RT for 3 h. After the reaction was completed, the reaction mixture was filtered to give the crude product, which was washed with ethyl acetate and dried in vacuum to afford (4-chloro-3-fluoropyridin-2-yl)methanamine hydrochloride (25.0 g, 78%, mixture) as a pink solid. $^1$H NMR (400 MHz, DMSO) δ 8.75 (br, 3H), 8.47 (d, J=5.2 Hz, 1H), 7.80 (t, J=5.6 Hz, 1H), 4.28-4.26 (m, 2H).

Synthesis of N-((4-chloro-3-fluoropyridin-2-yl)methyl)formamide. To a solution of (4-chloro-3-fluoropyridin-2-yl)methanamine hydrochloride (25.0 g, mixture, 127.0 mmol) in THF (200 mL) was added triethylamine (38.5 g, 380.6 mmol) and ethyl formate (100 mL) at RT. The resulting reaction mixture was stirred at 70° C. overnight. After the reaction was complete, the reaction mixture was filtered, the solid was washed with DCM three times. The combined organic solvent was washed with brine, dried by sodium sulfate, filtrated, and concentrated to afford N-((4-chloro-3- fluoropyridin-2-yl)methyl)formamide (crude), which was used in the next step directly without purification. ESI-MS [M+H]$^+$: 189.1.

Synthesis of 7-chloro-8-fluoroimidazo[1,5-a]pyridine. To a solution of N-((4-chloro-3-fluoropyridin-2-yl)methyl)formamide (crude, about 126.89 mmol) in dry acetonitrile (200 mL) was added phosphoryl trichloride (18 mL, 1.5 eq), and the resulting reaction mixture was stirred at reflux for 3 h. After the reaction was completed, the reaction mixture was cooled down to RT, and then poured into H$_2$O (200 mL) carefully. The pH was adjusted to 8 with saturated sodium bicarbonate, and then the resulting mixture was extracted with ethyl acetate (200 mL×3). The combined organic phase was washed with brine, dried over sodium sulphate, filtrated, and concentrated in vacuo. The residue was purified by silica gel chromatography (ethyl acetate) to afford 7-chloroimidazo[1,5-a]pyridine (12.0 g, yield: 56%) as a white solid. ESI-MS [M+H]$^+$: 171.1.

Synthesis of 7-chloro-8-fluoroimidazo[1,5-a]pyridine-1-carbaldehyde. A solution of 7-chloro-8-fluoroimidazo[1,5-a]pyridine (9.0 g, 52.6 mmol) in dry DMF (12 mL) was cooled with an ice-water bath to 0-5° C. Phosphorus oxychloride (7.4 g, 78.9 mmol, 1.5 eq) was added dropwise, and then the reaction mixture was stirred at 100° C. for 2 h. After the reaction was completed, the reaction mixture was cooled down to RT and poured into saturated sodium bicarbonate aqueous (200 mL) carefully. The resulting mixture was stirred at RT for 2 h and extracted with ethyl acetate (3×200 mL). The combined organic phase was washed with brine, dried over sodium sulphate, filtered, and concentrated in vacuo. The residue was purified by recrystallization (petroleum ether/ethyl acetate=1/1) to afford 7-chloroimidazo[1,5-a]pyridine-1-carbaldehyde (5.2 g, yield: 47%) as a brown solid. ESI-MS [M+H]$^+$: 181.1.

Synthesis of (Z)-N-((7-chloro-8-fluoroimidazo[1,5-a]pyridin-1-yl)methylene)-2-methylpropane-2-sulfinamide. To a solution of 7-chloro-8-fluoroimidazo[1,5-a]pyridine-1-carbaldehyde (5.2 g, 26.19 mmol) and 2-methylpropane-2-sulfinamide (3.2 g, 26.71 mmol) in THF (200 mL) was added tetraethoxytitanium (15.0 g, 65.50 mol). The reaction mixture was stirred at reflux overnight. After the reaction was completed, the reaction mixture was concentrated and the residue was purified by column chromatography (ethyl acetate) to give (E)-N-((7-chloro-8-fluoroimidazo[1,5-a]pyridin-1-yl)methylene)-2-methylpropane-2-sulfinamide (7.77 g, 98%) as a white solid. ESI-MS [M+H]$^+$: 302.1.

Synthesis of N-((7-chloro-8-fluoroimidazo[1,5-a]pyridin-1-yl)methyl)-2-methylpropane-2-sulfinamide. To a solution of (E)-N-((7-chloro-8-fluoroimidazo[1,5-a]pyridin-1-yl)methylene)-2-methylpropane-2-sulfinamide (7.77 g, 25.75 mmol) in MeOH (200 mL) was added sodium borohydride (2.44 g, 64.37 mmol) slowly. The resulting reaction mixture was stirred at RT for 3 h. After the reaction was completed, the reaction was quenched with H$_2$O (50 mL). The resulting mixture was extracted with ethyl acetate (200 mL×3), the combined organic phase was washed with brine, dried over anhydrous sodium sulphate, filtered, and concentrated in vacuum to afford N-((7-chloro-8-fluoroimidazo[1,5-a]pyridin-1-yl)methyl)-2-methylpropane-2-sulfinamide (7.77 g, 99%) as a white solid. ESI-MS [M+H]$^+$: 304.1.

Synthesis of (7-chloro-8-fluoroimidazo[1,5-a]pyridin-1-yl)methanamine hydrochloride. A mixture of N-((7-chloro-8-fluoroimidazo[1,5-a]pyridin-1-yl)methyl)-2-methylpropane-2-sulfinamide (7.77 g, 25.5 mmol) and hydrochloride acid in ethyl acetate (3 M, 100 mL) was stirred at RT for 2 h, and then the reaction mixture was filtered to give the crude product, which was washed with ethyl acetate and dried in vacuum to afford (7-chloro-8-fluoroimidazo[1,5-a]pyridin-1-yl)methanamine hydrochloride salt (6.03 g, quant.) as a white solid. ESI-MS [M-NH$_2$]$^+$: 182.9. $^1$H NMR (400 MHz, DMSO): δ 8.64 (d, J=2.0 Hz, 1H), 8.44 (br, 3H), 8.33 (d, J=7.2 Hz, 1H), 6.92 (t, J=6.8 Hz, 1H), 4.26-4.22 (m, 2H).

Synthesis of ethyl 1-((6-cyclopropylimidazo[1,2-a]pyridin-2-yl)methyl)-1H-pyrazole-4-carboxylate Synthesis of 5-cyclopropylpyridin-2-amine. A solution of 5-bromopyridin-2-amine (5 g, 29.1 mmol), cyclopropylboronic acid (3.75 g, 43.6 mmol), Pd(OAc)$_2$ (651 mg, 2.91 mmol), SPhos (1.19 g, 2.91 mmol) and K$_3$PO$_4$ (18.5 g, 87.3 mmol) in toluene/H$_2$O (100 mL/10 mL) was stirred at 95° C. for 12 h under nitrogen. Then the reaction mixture was quenched with H$_2$O (50 mL) and extracted with DCM (200 mL). The combined organic layers were dried over Na$_2$SO$_4$ and concentrated in vacuo to give the crude residue which was purified by silica gel chromatography (PE/EtOAc=1/1) to give the 5-cyclopropylpyridin-2-amine as yellow solid (3.8 g, 97.4% yield). ESI-MS [M+H]$^+$: 135.2.

Synthesis of 2-(chloromethyl)-6-cyclopropylimidazo[1,2-a]pyridine. To a solution 5-cyclopropyl-4-methylpyridin-2-amine (500 mg, 3.70 mmol) in DMF (10 mL) was added 1,3-dichloropropan-2-one (1409 mg, 11.1 mmol) at RT. The resulting reaction was stirred at 85° C. for 2 h. The solution was quenched with H$_2$O (60 mL), adjusted to pH 8 by adding saturated NaHCO$_3$ solution, and extracted with EtOAc (50 mL×3). The combined organic layers were washed with brine, dried over Na$_2$SO$_4$, and concentrated in vacuo to give the crude, which was purified with prep-TLC (PE/EtOAc=1/1) to give the 2-(chloromethyl)-6-cyclopropyl-7-methylimidazo[1,2-a]pyridine (300 mg, yield: 39%) as a light yellow oil. ESI-MS [M+H]$^+$: 207.2.

Synthesis of ethyl 1-((6-cyclopropylimidazo[1,2-a]pyridin-2-yl)methyl)-1H-pyrazole-4-carboxylate. To a solution 2-(chloromethyl)-6-cyclopropylimidazo[1,2-a]pyridine (2 g, 9.70 mmol) in DMF (20 mL) was added ethyl 1H-pyrazole-4-carboxylate (906 mg, 6.46 mmol) and Cs$_2$CO$_3$ (6.32 g, 19.38 mmol) at RT. The resulting reaction was stirred at RT for 12 h. H$_2$O (150 mL) was added to the reaction and then the mixture was extracted with EtOAc (100 mL×3). The combined organic layers were washed with brine, dried over Na$_2$SO$_4$, concentrated in vacuo to give the crude, which was purified with silica gel chromatography (DCM/MeOH=20/1) to give the ethyl 1-((6-cyclopropylimidazo[1,2-a]pyridin-2-yl)methyl)-1H-pyrazole-4-carboxylate (1.5 g, yield: 75%) as a white solid. ESI-MS [M+H]$^+$: 311.2.

Synthesis of Tert-Butyl 1-((8-bromo-6-cyclopropylimidazo[1,2-a]pyridin-2-yl)methyl)-1H-1,2,3-triazole-4-carboxylate Synthesis of 3-bromo-5-cyclopropylpyridin-2-amine. To a solution of 5-cyclopropylpyridin-2-amine (8.08 g, 60 mmol) in MeCN (200 mL) was added NBS (11.72 g, 66 mmol) in portions at 0° C. during 30 min. The mixture was stirred at 0° C. for additional 30 min and then concentrated to give the crude, which was purified by silica gel chromatography (PE/EA=5/1 to 4/1) to afford 3-bromo-5-cyclopropylpyridin-2-amine as a white solid (8.23 g, yield: 64%). ESI-MS [M+H]$^+$: 212.8, Synthesis of 8-bromo-2-(chloromethyl)-6-cyclopropylimidazo[1,2-a]pyridine. A solution of 3-bromo-5-cyclopropylpyridin-2-amine (8.23 g, 38.6 mmol) and 1,3-dichloropropan-2-one (7.46 g, 57.9 mmol) in EtOAc (80 mL) was stirred at 70° C. for 48° C. The reaction mixture was diluted with EtOAc (300 mL) and washed with saturate aqueous NaHCO₃ (100 mL). The organic layer was washed brine, dried over Na₂SO₄, concentrated in vacuo to give the crude, which was purified with silica gel (EtOAc/PE=1/2) to give (8 g, yield: 72.3%) as a yellow solid. ESI-MS [M+H]⁺: 284.8

Synthesis of 2-(azidomethyl)-8-bromo-6-cyclopropylimidazo[1,2-a]pyridine. To a solution of 8-bromo-2-(chloromethyl)-6-cyclopropylimidazo[1,2-a]pyridine (1 g, 3.5 mmol) in DMF (15 mL) was added NaN₃ (230 mg, 3.5 mmol). The resulting mixture was stirred at 50° C. for 24 h under nitrogen. H₂O (50 mL) was added to the reaction, extracted with EtOAc (50 mL×3). The combined organic layers were washed brine, dried over Na₂SO₄, concentrated in vacuo to give 2-(azidomethyl)-8-bromo-6-cyclopropylimidazo[1,2-a]pyridine (1.1 g, crude), which was used into next step without further purification. ESI-MS [M+H]⁺: 292.0.

Synthesis of tert-butyl 1-((8-bromo-6-cyclopropylimidazo[1,2-a]pyridin-2-yl)methyl)-1H-1,2,3-triazole-4-carboxylate. To a solution 2-(azidomethyl)-8-bromo-6-cyclopropylimidazo[1,2-a]pyridine (1.1 g, crude from previous step) and tert-butyl propiolate (860 mg, 6.8 mmol) in t-BuOH/H₂O (15 mL/15 mL) was added CuSO₄ (170 mg, 0.68 mmol), sodium ascorbate (180 mg, 1.02 mmol). The reaction mixture was stirred at RT for 12 h. The mixture was concentrated in vacuo to give the crude product, which was purified by silica gel chromatography (PE/EtOAc=1/2) to give tert-butyl 1-((8-bromo-6-cyclopropylimidazo[1,2-a]pyridin-2-yl)methyl)-1H-1,2,3-triazole-4-carboxylate (500 mg, 34% over 2 steps) as brown oil. ESI-MS [M+H]⁺: 417.7.

Example 1

2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1)

Scheme 1

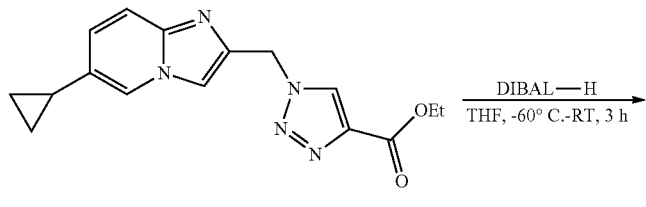

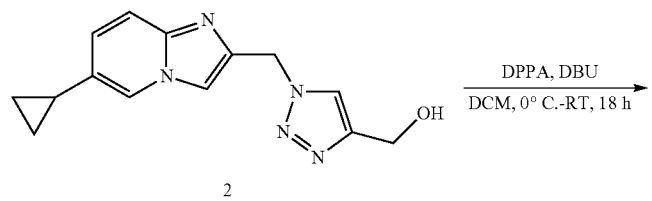

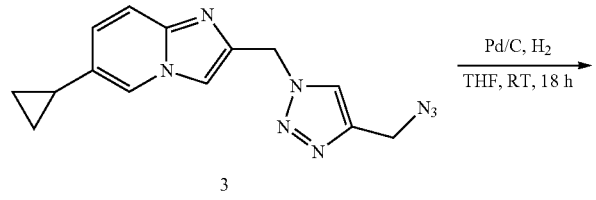

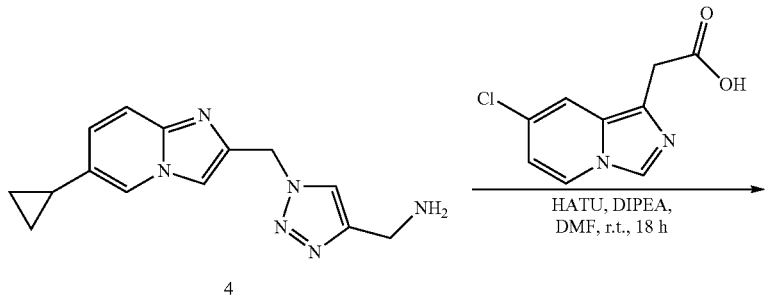

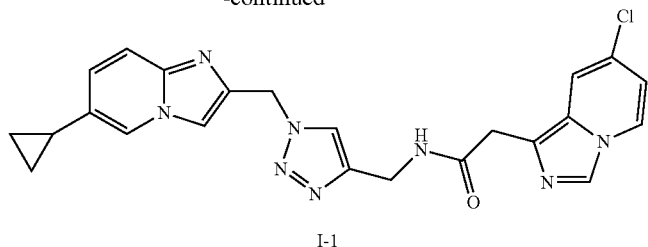

I-1

Synthesis of (1-((6-cyclopropylimidazo[1,2-a]pyridin-2-yl)methyl)-1H-1,2,3-triazol-4-yl)methanol

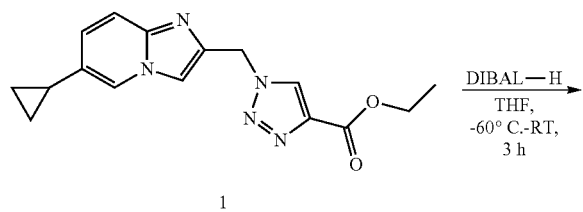

To a solution of ethyl 1-((6-cyclopropylimidazo[1,2-a]pyridin-2-yl)methyl)-1H-1,2,3-triazole-4-carboxylate (10.0 g, 33.7 mmol) in THF (100 mL) was added DIBAL-H (67.3 mL, 67.3 mmol) at −60° C. The mixture was stirred at room temperature for 3 h and then quenched with saturated aq. NaHCO$_3$ solution (300 mL) and extracted with EtOAc (150 mL×3). The combined organic layers were washed with brine (200 mL), dried over Na$_2$SO$_4$ and concentrated in vacuo. The residue was purified by flash column chromatography (PE/EtOAc from 0 to 80%) to give (1-((6-cyclopropylimidazo[1,2-a]pyridin-2-yl)methyl)-1H-1,2,3-triazol-4-yl)methanol (7.5 g, yield: 82%) as an off-white solid. ESI-MS [M+H]$^+$: 270.1

Synthesis of 2-((4-(azidomethyl)-1H-1,2,3-triazol-1-yl)methyl)-6-cyclopropylimidazo[1,2-a]pyridine

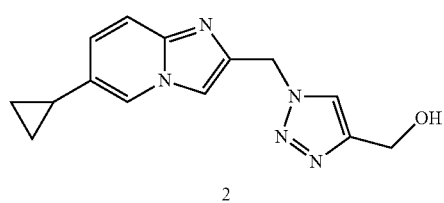

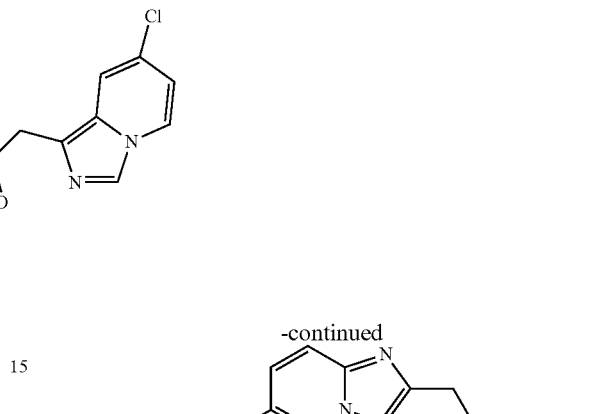

To a solution of (1-((6-cyclopropylimidazo[1,2-a]pyridin-2-yl)methyl)-1H-1,2,3-triazol-4-yl)methanol (5 g, 18.6 mmol) and DPPA (10.2 g, 37.2 mmol) in DCM (80 mL) was added DBU (11.3 g, 74.4 mmol) dropwise at 0° C. After stirring at room temperature for 18 h, the reaction was quenched with saturated aqueous NH$_4$Cl (100 mL) and extracted with DCM (100 mL×3). The combined organic layers were washed with brine (70 mL), dried over Na$_2$SO$_4$ and concentrated in vacuo to give the crude, which was purified with silica gel chromatography (PE/EtOAc from 0 to 50%) to give 2-((4-(azidomethyl)-1H-1,2,3-triazol-1-yl)methyl)-6-cyclopropylimidazo[1,2-a]pyridine (2 g, yield: 36.6%) as a white solid. [M+H]$^+$: 295.2

Synthesis of (1-((6-cyclopropylimidazo[1,2-a]pyridin-2-yl)methyl)-1H-1,2,3-triazol-4-yl)methanamine

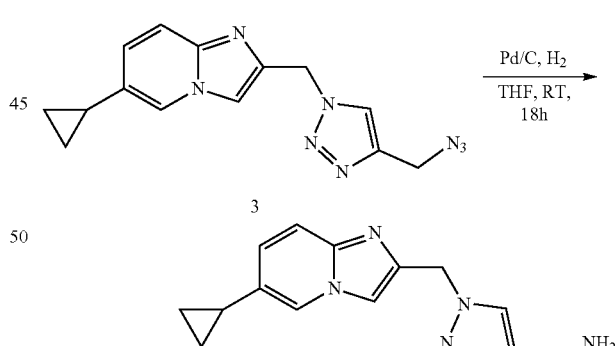

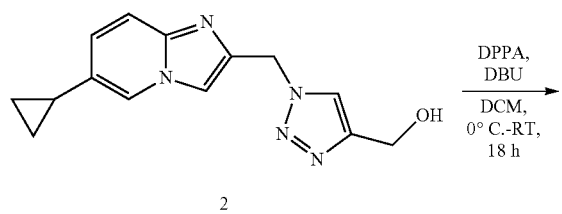

A mixture of 2-((4-(azidomethyl)-1H-1,2,3-triazol-1-yl)methyl)-6-cyclopropylimidazo[1,2-a]pyridine (2 g, 6.8 mmol) and Pd/C (200 mg) in THF (80 mL) was stirred at room temperature under H$_2$ atmosphere for 18h. The reaction mixture was filtered and washed with MeOH (100 mL). The filtrate was concentrated in vacuo to give (1-((6-cyclopropylimidazo[1,2-a]pyridin-2-yl)methyl)-1H-1,2,3-triazol-4-yl)methanamine (1 g, yield: 54.9%) as a yellow solid. [M+H]$^+$: 269.2

51

Synthesis of 2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1)

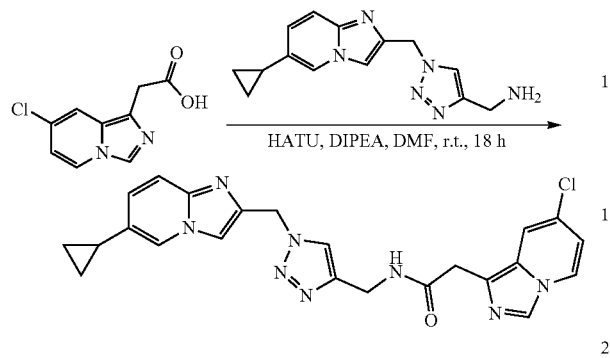

A mixture of 2-(7-chloro-1,8a-dihydroimidazo[1,5-a]pyridin-1-yl)acetic acid (40 mg, 0.19 mmol), HATU (110 mg, 0.29 mmol), DIPEA (74 mg, 0.57 mmol) and (1-((6-cyclopropylimidazo[1,2-a]pyridin-2-yl)methyl)-1H-1,2,3-triazol-4-yl)methanamine (51 mg, 0.19 mmol) in DMF (3 mL) was stirred at rt for 18 h. Water (30 mL) was added and the mixture was extracted with EtOAc (30 mL×3). The combined organic layers were washed with brine (40 mL×2), dried over Na$_2$SO$_4$, and concentrated in vacuo to give the crude, which was purified by Prep-TLC (DCM/MeOH=20/1) to provide 2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (50 mg, yield: 57%) as a white solid. ESI-MS: [M+H]$^+$ 461.2.

1H NMR (400 MHz, DMSO) δ 8.45-8.42 (m, 1H), 8.36 (s, 1H), 8.29-8.27 (m, 2H), 7.89 (s, 1H), 7.83 (s, 1H), 7.72 (s, 1H), 7.41 (d, J=9.3 Hz, 1H), 7.02 (d, J=9.4 Hz, 1H), 6.63-6.61 (m, 1H), 5.63 (s, 2H), 4.27 (d, J=5.6 Hz, 2H), 3.66 (s, 2H), 1.97-1.90 (m, 1H), 0.95-0.90 (m, 2H), 0.70-0.66 (m, 2H).

Example 2

1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine (I-2)

Scheme 2

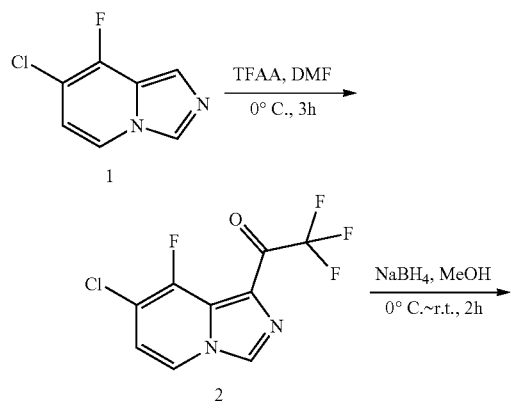

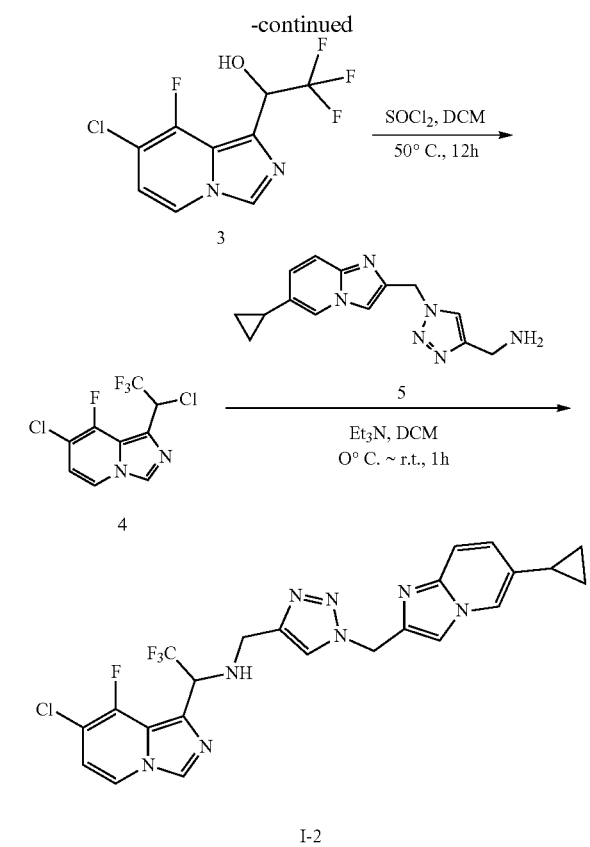

Synthesis of 1-(7-chloro-8-fluoroimidazo[1,5-a]pyridin-1-yl)-2,2,2-trifluoroethan-1-ol

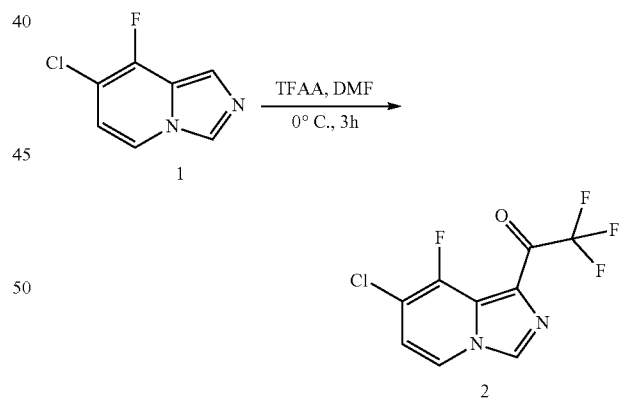

To a solution of 7-chloro-8-fluoroimidazo[1,5-a]pyridine (510 mg, 3 mmol) in DMF (15 mL) was added TFAA (1.58 g, 7.5 mmol) dropwise at 0° C. The reaction mixture was stirred at 0° C. for 3 h, then H$_2$O (50 mL) was added and the mixture was extracted with EtOAc (50 mL×3). The combined organic layers were washed with brine (50 mL), dried over Na$_2$SO$_4$, and concentrated in vacuo to give the crude, which was purified with silica gel column (PE/EtOAc=1/1) to provide 1-(7-chloro-8-fluoroimidazo[1,5-a]pyridin-1-yl)-2,2,2-trifluoroethan-1-one (400 mg, yield: 50%) as a yellow solid. ESI-MS [M+H]$^+$: 267.0.

Synthesis of 1-(7-chloro-8-fluoroimidazo[1,5-a]pyridin-1-yl)-2,2,2-trifluoroethan-1-ol

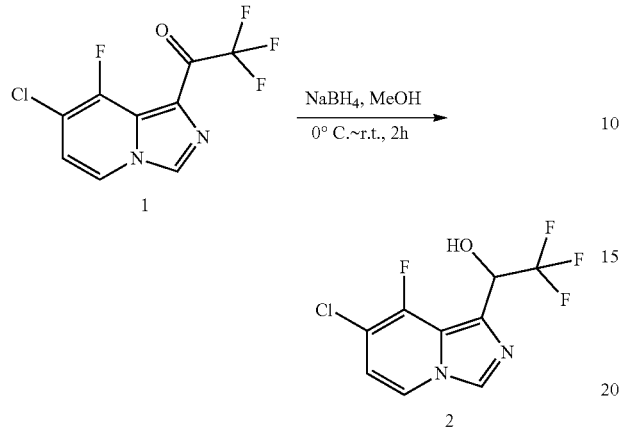

Synthesis of 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine

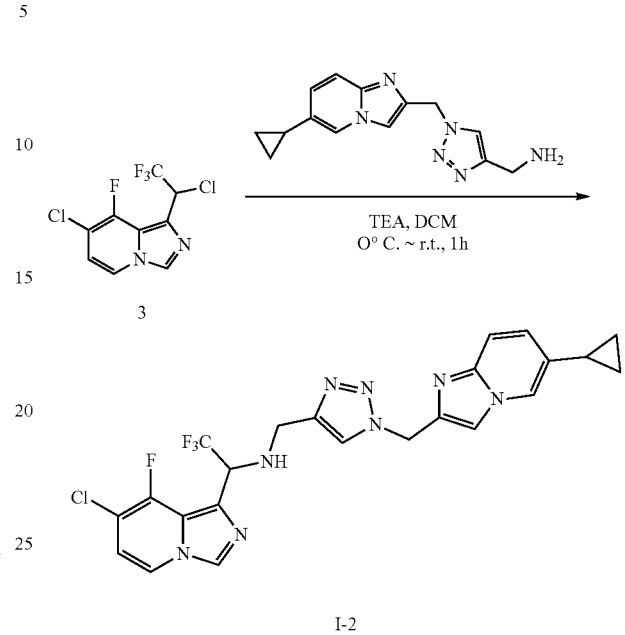

To a solution of 1-(7-chloro-8-fluoroimidazo[1,5-a]pyridin-1-yl)-2,2,2-trifluoroethan-1-one (50 mg, 0.19 mmol) in MeOH (10 mL) at 0° C. was added NaBH₄ (29 mg, 0.77 mmol). The reaction mixture was stirred at room temperature for 2 h, then H₂O (20 mL) was added. The aqueous phase was extracted with EtOAc (30 mL×3). The combined organic layers were washed with brine (30 mL×2), dried over Na₂SO₄, and concentrated in vacuo to give the crude, which was purified by Prep-TLC (DCM/MeOH=10/1) to give 1-(7-chloro-8-fluoroimidazo[1,5-a]pyridin-1-yl)-2,2,2-trifluoroethan-1-ol as a white solid (46 mg, 90.2%). ESI-MS [M+H]⁺: 269.0.

Synthesis of 7-chloro-1-(1-chloro-2,2,2-trifluoroethyl)-8-fluoroimidazo[1,5-a]pyridine

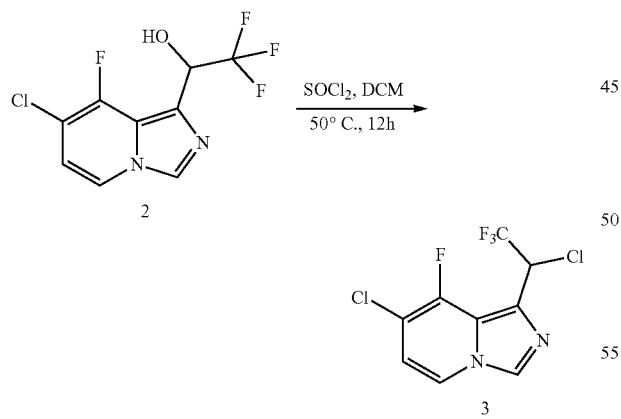

To a solution 1-(7-chloro-8-fluoroimidazo[1,5-a]pyridin-1-yl)-2,2,2-trifluoroethan-1-ol (46 mg, 0.17 mmol) in DCM (10 mL) was added SOCl₂ (0.5 mL). The resulting mixture was heated to 50° C. and stirred for 12 h. The reaction mixture was concentrated in vacuo to give 7-chloro-1-(1-chloro-2,2,2-trifluoroethyl)-8-fluoroimidazo[1,5-a]pyridine (49 mg crude), which was used in the next step without further purification. (49 mg crude). ESI-MS [M+H]⁺: 288.1

To a solution of (1-((6-cyclopropylimidazo[1,2-a]pyridin-2-yl)methyl)-1H-1,2,3-triazol-4-yl)methanamine (46 mg, 0.17 mmol) and triethylamine (174 mg, 1.72 mmol) in DCM (5 mL) was added 7-chloro-1-(1-chloro-2,2,2-trifluoroethyl)-8-fluoroimidazo[1,5-a]pyridine (46 mg, 0.16 mmol) at 0° C. The reaction mixture was stirred at room temperature for 1 h. The resulting mixture was poured into H₂O (20 mL) and extracted with DCM (25 mL×3). The combined organic layers were washed with brine (30 mL×2), dried over Na₂SO₄, and concentrated in vacuo to give the crude, which was purified by prep-HPLC to give 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine as a white solid (6 mg, 7%). ESI-MS [M+H]⁺: 519.1.

1H NMR (400 MHz, DMSO) δ 8.39 (d, J=7.5 Hz, 1H), 8.35 (s, 1H), 7.86 (s, 1H), 7.78 (s, 1H), 7.60 (s, 1H), 7.40 (d, J=9.3 Hz, 1H), 7.01 (d, J=9.4 Hz, 1H), 6.89 (t, J=7.0 Hz, 1H), 5.55 (s, 2H), 5.42-5.34 (m, 1H), 3.82-3.71 (m, 2H), 1.95-1.90 (m, 1H), 0.93-0.90 (m, 2H), 0.70-0.66 (m, 2H).

Example 3

7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (I-3)

Scheme 3

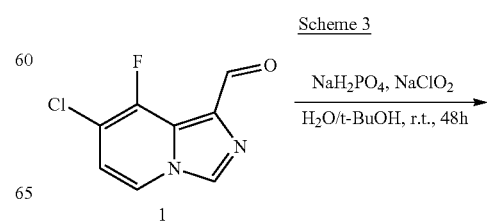

-continued

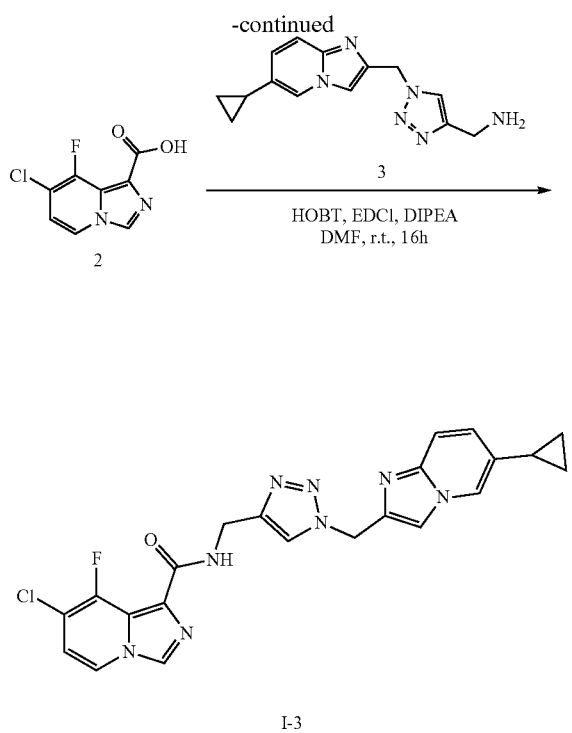

I-3

Synthesis of 7-chloro-8-fluoroimidazo[1,5-a]pyridine-1-carboxylicacid

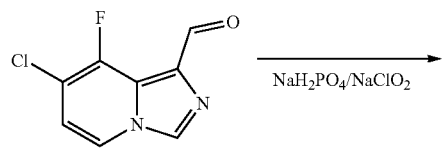

To a solution of 7-chloro-8-fluoroimidazo[1,5-a]pyridine-1-carbaldehyde (0.3 g, 1.5 mmol) in H₂O (5 mL) and t-BuOH (10 mL) was added NaH₂PO₄ (0.4 g, 3.0 mmol) and NaClO₂ (0.3 g, 3.0 mmol). The mixture was stirred at room temperature for 48 h. Water (30 mL) was added and the mixture was extracted with EtOAc (20 mL×3). The combined organic layers were washed with brine, dried over Na₂SO₄, concentrated and purified by silica gel chromatography (DCM/MeOH=10/1) to give 7-chloro-8-fluoroimidazo[1,5-a]pyridine-1-carboxylic acid (0.15 g, yield: 46.6%) as a white solid. ESI-MS [M+H]⁺: 215.0.

Synthesis of 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide

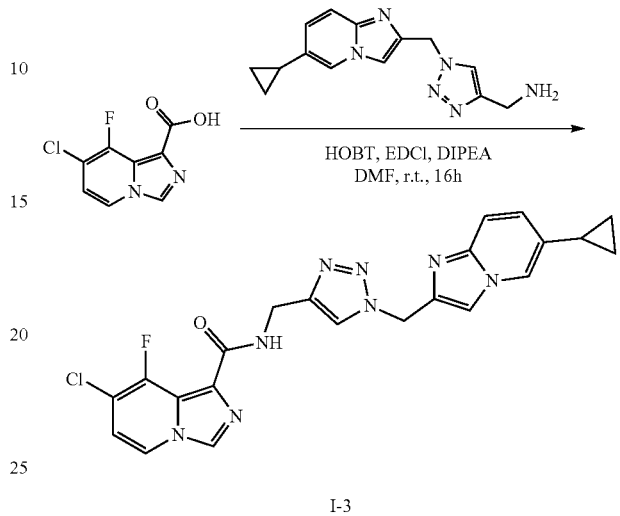

I-3

To a solution of 7-chloro-8-fluoroimidazo[1,5-a]pyridine-1-carboxylic acid (60 mg, 0.28 mmol) in DMF (5 mL) was added (1-((6-cyclopropylimidazo[1,2-a]pyridin-2-yl)methyl)-1H-1,2,3-triazol-4-yl)methanamine (75 mg, 0.28 mmol), HOBt (56.7 mg, 0.42 mmol), EDCI (80.6 mg, 0.42 mmol) and DIPEA (108.4 mg, 0.84 mmol). The mixture was stirred at room temperature for 16 h. The reaction mixture was concentrated in vacuo to give the crude, which was purified by Prep-HPLC to give 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (30 mg, yield: 23.1%) as a white solid. ESI-MS [M+H]⁺: 465.1.

1H NMR (400 MHz, DMSO) δ 8.63 (t, J=6.0 Hz, 1H), 8.58 (d, J=1.5 Hz, 1H), 8.40-8.31 (m, 2H), 8.19 (s, 1H), 7.92 (s, 1H), 7.81 (s, 1H), 7.40 (d, J=9.3 Hz, 1H), 6.94-7.06 (m, 2H), 5.63 (s, 2H), 4.50 (d, J=6.0 Hz, 2H), 1.84-1.98 (m, 1H), 0.97-0.86 (m, 2H), 0.73-0.62 (m, 2H).

Example 4

N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide (I-4)

Scheme 4

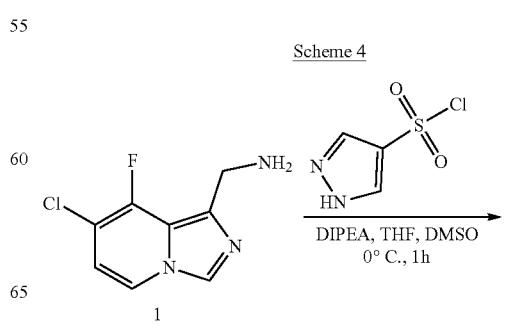

-continued

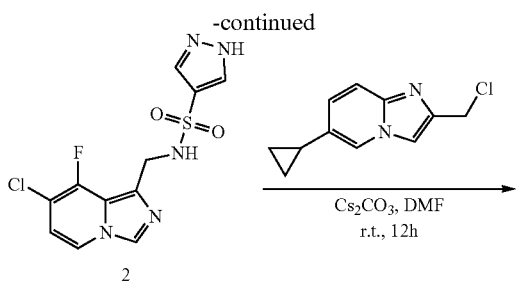

Synthesis of N-((7-chloro-8-fluoroimidazo[1,5-a]pyridin-1-yl)methyl)-1H-pyrazole-4-sulfonamide

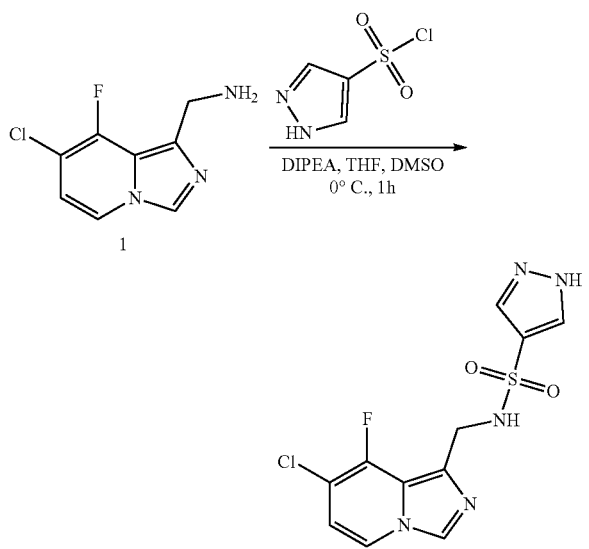

To a solution of (7-chloro-8-fluoroimidazo[1,5-a]pyridin-1-yl)methanamine hydrochloride (1.06 g, 5.3 mmol) and DIPEA (1.33 mL, 7.5 mmol) in THF (15 mL) was added a solution of 1H-pyrazole-4-sulfonyl chloride (250 mg, 1.5 mmol) in DMSO (5 mL) at 0° C. The reaction mixture was stirred at 0° C. for 1h. Water (30 mL) was added and the mixture was extracted with EtOAc (50 mL×3). The combined organic layers were washed with brine, dried over Na₂SO₄, and concentrated in vacuo to give the crude, which was purified by silica gel chromatography (eluent: DCM/MeOH=10/1) to give N-((7-chloro-8-fluoroimidazo[1,5-a]pyridin-1-yl)methyl)-1H-pyrazole-4-sulfonamide as a yellow solid. (70 mg, yield: 14.2%), ESI-MS [M+H]⁺: 330.2

Synthesis of 1-((6-cyclopropylimidazo[1,2-a]pyridin-2-yl)methyl)-N-(2-fluoro-3-methoxy-6-(1H-tetrazol-1-yl)benzyl)-1H-pyrazole-4-sulfonamide

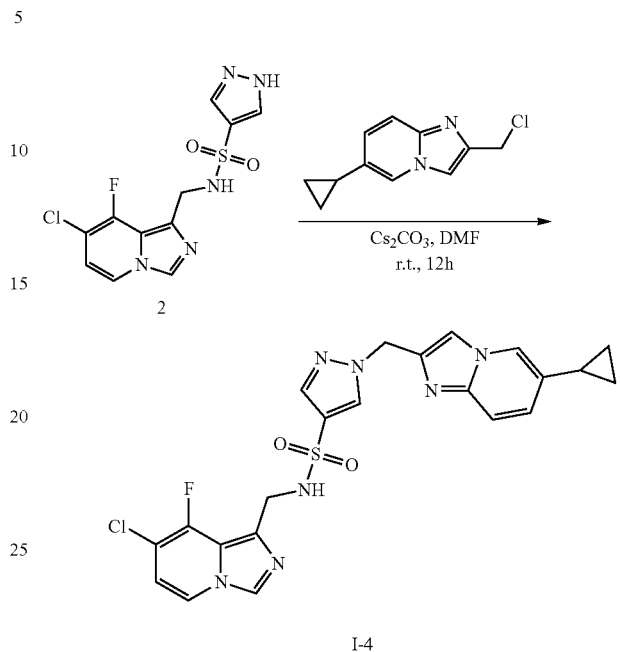

A mixture of N-((7-chloro-8-fluoroimidazo[1,5-a]pyridin-1-yl)methyl)-1H-pyrazole-4-sulfonamide (70 mg, 0.21 mmol), 2-(chloromethyl)-6-cyclopropylimidazo[1,2-a]pyridine (43 mg, 0.21 mmol) and Cs₂CO₃ (205 mg, 0.63 mmol) in DMF (10 mL) was stirred at room temperature for 12 h. Water (25 mL) was added and the mixture was extracted with EtOAc (40 mL×3). The combined organic layers were washed with brine, dried over Na₂SO₄, and concentrated in vacuo to give the crude, which was purified by Prep-HPLC to give N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide as a white solid (7 mg, 6.7%). ESI-MS [M+H]⁺: 500.1, Purity: 99.75%(214 nm), 99.89% (254 nm).

1H NMR (400 MHz, DMSO) δ 8.41 (d, J=2.3 Hz, 1H), 8.35 (s, 1H), 8.19-8.17 (m, 2H), 7.78-7.77 (m, 2H), 7.66 (s, 1H), 7.42 (d, J=9.3 Hz, 1H), 7.01 (dd, J=9.4, 1.7 Hz, 1H), 6.75 (t, J=8.0 Hz, 1H), 5.42 (s, 2H), 4.23 (d, J=5.5 Hz, 2H), 1.97-1.87 (m, 1H), 0.95-0.90 (m, 2H), 0.70-0.66 (m, 2H).

Example 5

N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide (I-5)

Scheme 5

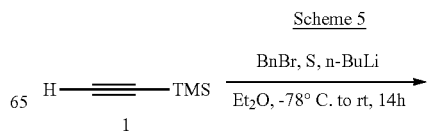

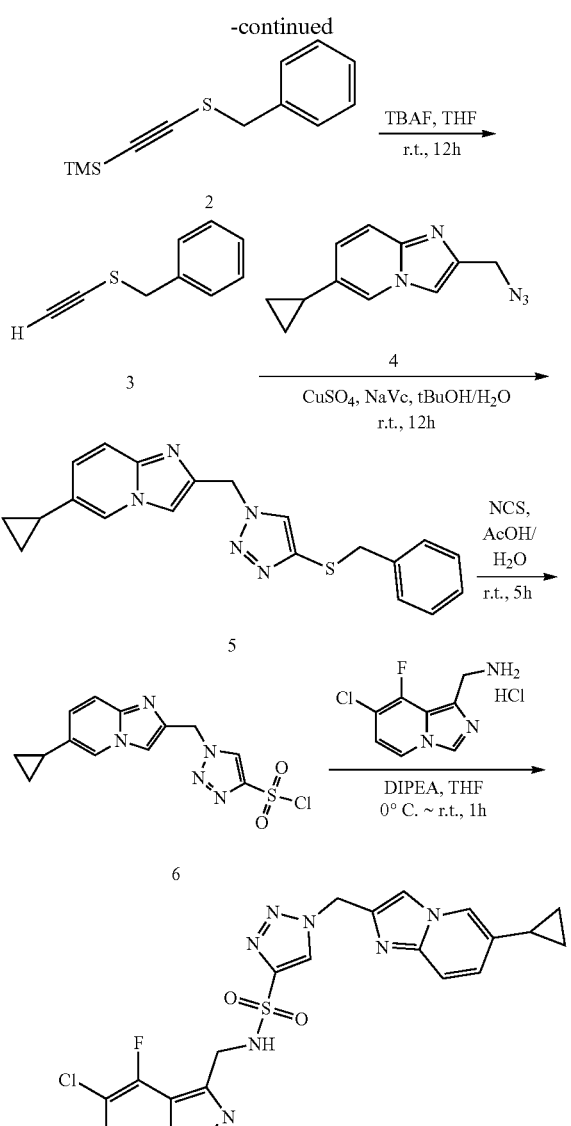

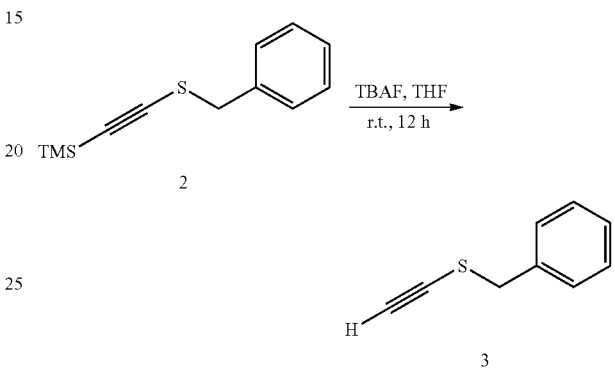

mmol) was added and the reaction mixture was stirred at −78° C. for another 15 min. The reaction was allowed to warm to room temperature and stirred for 1 h until the S was consumed, then cooled to 0° C. BnBr (17.1 g, 100 mmol) was added and the resulting mixture was stirred at room temperature for 14h. The reaction was concentrated in vacuo to give the crude, which was purified by silica gel chromatography (eluent: PE) to give ((benzylthio)ethynyl)trimethylsilane as a yellow oil (20 g, 91%). 1H NMR (400 MHz, CDCl$_3$) δ 7.25-7.13 (m, 5H), 3.80 (s, 2H), 0.00 (s, 9H).

Synthesis Benzyl(Ethynyl)Sulfane

To a solution of ((benzylthio)ethynyl)trimethylsilane (20 g, 90.9 mmol) in THF (50 mL) was added TBAF (75 mL, 1 M solution in THF, 75 mmol). The resulting solution was stirred at room temperature for 12 h. The reaction was quenched with saturated aqueous NH$_4$Cl (100 mL) and extracted with Et$_2$O (100 mL×2). The combined organic layers were washed with brine, dried over Na$_2$SO$_4$, and concentrated in vacuo to give benzyl(ethynyl)sulfane, which was used in the next step without further purification. (12 g, crude yield: 91%)

1H NMR (400 MHz, CDCl$_3$) δ 7.35-7.26 (m, 5H), 3.96 (s, 2H), 2.82 (s, 1H).

Synthesis Benzyl(Ethynyl)Sulfane

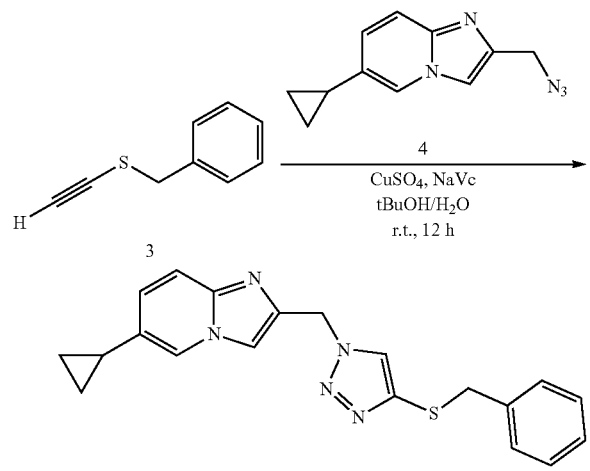

Synthesis ((Benzylthio)Ethynyl)Trimethylsilane

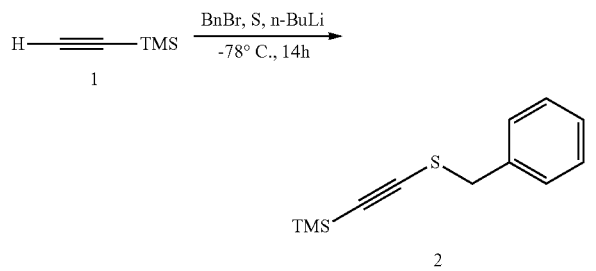

To a solution of ethynyltrimethylsilane (9.8 g, 100 mmol) in dry Et$_2$O (150 mL) was added n-BuLi (42 mL, 2.4 M solution in hexane, 100.8 mmol) slowly at −78° C. The reaction was stirred at −78° C. for 15 min. Then S (3.2 g, 100

To a solution of benzyl(ethynyl)sulfane (4 g, 27 mmol) and 2-(azidomethyl)-6-cyclopropylimidazo[1,2-a]pyridine (6.9 g, 32.4 mmol) in tBuOH/H$_2$O (40 mL/40 mL) was added CuSO$_4$ (2.1 g, 13.2 mmol) and sodium ascorbate (2.61 g, 13.2 mmol). The reaction was stirred at room temperature for 12 h. H$_2$O (150 mL) was added and the mixture was extracted with DCM (150 mL×3). The combined organic layers were washed with brine, dried over Na$_2$SO$_4$, and concentrated in vacuo to give the crude, which was purified with silica gel chromatography (DCM/MeOH=15/1) to give 2-((4-(benzylthio)-1H-1,2,3-triazol-1-yl)methyl)-6-cyclopropylimidazo[1,2-a]pyridine as a black solid. (3.5 g, 36%). ESI-MS [M+H]$^+$: 362.2

Synthesis 1-((6-cyclopropylimidazo[1,2-a]pyridin-2-yl)methyl)-1H-1,2,3-triazole-4-sulfonyl chloride

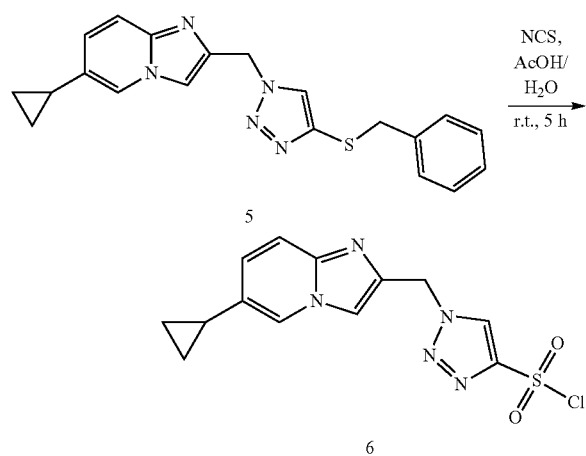

To a solution of 2-((4-(benzylthio)-1H-1,2,3-triazol-1-yl)methyl)-6-cyclopropylimidazo[1,2-a]pyridine (500 mg. 1.39 mmol) in AcOH/H$_2$O (15 mL/5 mL) was added NCS (197 mg, 1.39 mmol). The reaction was stirred at room temperature for 2 h. Additional NCS (197 mg, 1.39 mmol) was added to the reaction. The resulting reaction mixture was stirred for another 3 h. The mixture was concentrated in vacuo to give the crude, which was used in the next step without further purification (650 mg crude). ESI-MS [M+H]$^+$: 338.0

Synthesis N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide

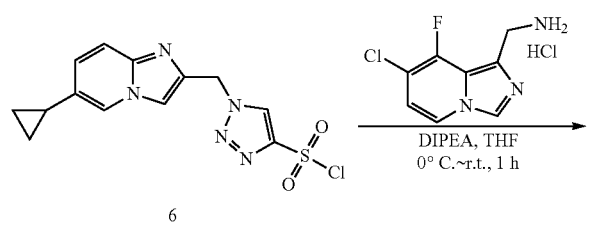

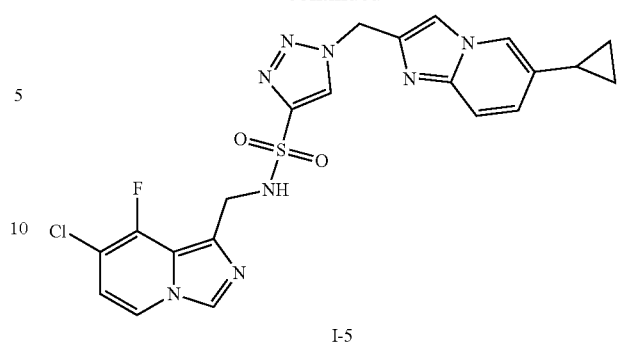

To a mixture of (7-chloro-8-fluoroimidazo[1,5-a]pyridin-1-yl)methanamine hydrochloride (100 mg, 0.42 mmol) and DIPEA (774 mg, 6 mmol) in dry THF (15 mL) was added 1-((6-cyclopropylimidazo[1,2-a]pyridin-2-yl)methyl)-1H-1,2,3-triazole-4-sulfonyl chloride (650 mg crude from previous step) in 5 mL THF at 0° C. The reaction was stirred at room temperature for 1 h. Water (50 mL) was added and the mixture was extracted with EtOAc (50 mL×3). The combined organic layers were washed with brine, dried over Na$_2$SO$_4$, and concentrated in vacuo to give the crude, which was purified by Prep-HPLC to give N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide as a white solid. (18 mg, yield: 2.6% over 2 steps) ESI-MS [M+H]$^+$: 501.1, Purity: 99.78%(214 nm), 100% (254 nm)

1H NMR (400 MHz, DMSO) δ 8.70 (s, 1H), 8.58 (s, 1H), 8.37 (s, 1H), 7.88 (s, 1H), 7.39 (d, J=9.3 Hz, 1H), 7.20-7.10 (m, 2H), 7.03-7.00 (m, 2H), 6.85 (d, J=3.6 Hz, 1H), 5.85-5.56 (m, 2H), 2.50 (s, 1H), 1.97-1.92 (m, 2H), 1.23-1.16 (m, 2H), 0.95-0.87 (m, 2H), 0.70-0.66 (m, 2H).

Example 6

7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-sulfonamide (I-6)

Scheme 6

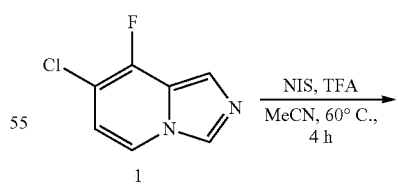

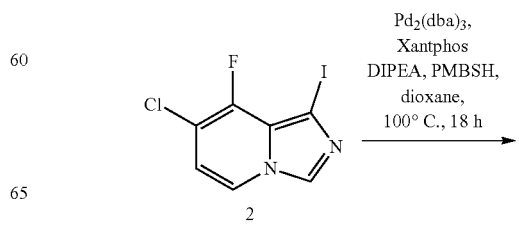

-continued

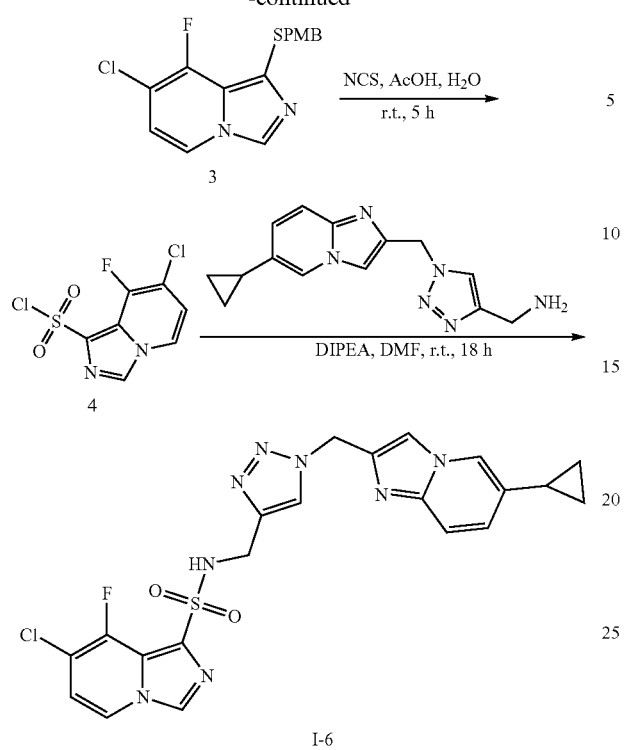

Synthesis of 7-chloro-8-fluoro-1-iodoimidazo[1,5-a]pyridine

A mixture of 7-chloro-8-fluoroimidazo[1,5-a]pyridine (1.7 g, 10 mmol), NIS (2.5 g, 11 mmol) and TFA (342 mg, 3.0 mmol) in MeCN (15 mL) was stirred at 60° C. for 4 h. The reaction was cooled to 0° C., quenched with saturated aqueous NaHCO$_3$(50 mL), and extracted with DCM (50 mL×3). The combined organic layers were washed with brine (30 mL), dried over Na$_2$SO$_4$ and concentrated in vacuo. The residue was purified by flash column chromatography (MeOH/DCM=1/20) to give 7-chloro-8-fluoro-1-iodoimidazo[1,5-a]pyridine (1.5 g, yield: 50%) as yellow oil. ESI-MS [M+H]$^+$: 297.0.

Synthesis of 7-chloro-8-fluoro-1-((4-methoxybenzyl)thio)imidazo[1,5-a]pyridine

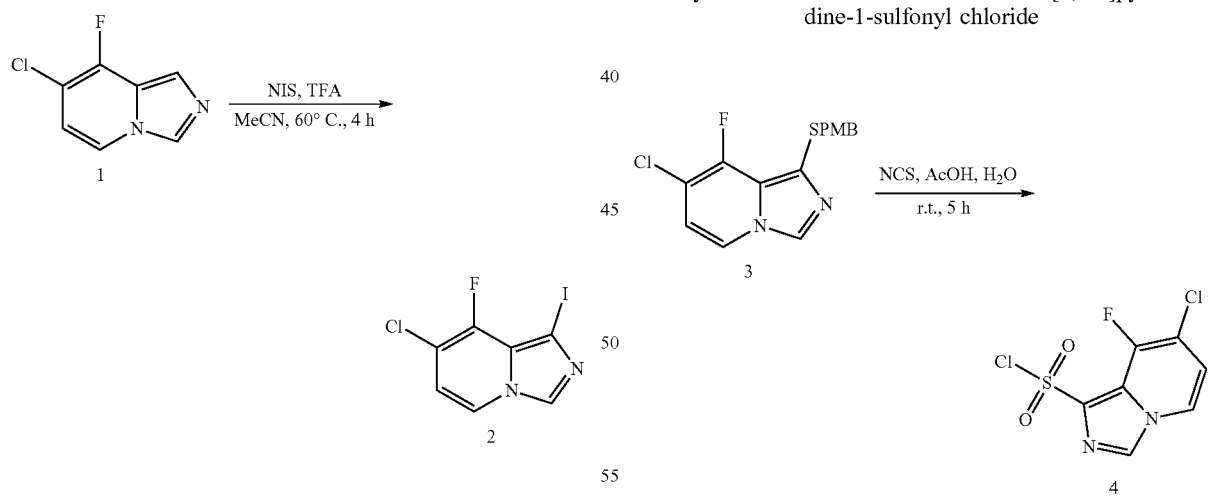

A mixture of 7-chloro-8-fluoro-1-iodoimidazo[1,5-a]pyridine (1.18 g, 4.0 mmol), (4-methoxyphenyl)methanethiol (0.74 g, 4.8 mmol), Xantphos (116 mg, 0.2 mmol), Pd$_2$(dba)$_3$(183 mg, 0.2 mmol) and DIPEA (1.03 g, 8.0 mmol) in dioxane (15 mL) was stirred at 100° C. for 18 h. The reaction was cooled to room temperature, diluted with water (50 mL), and extracted with EtOAc (50 mL×3). The combined organic layers were washed with brine (50 mL), dried over Na$_2$SO$_4$ and concentrated in vacuo to give the crude, which was purified with silica gel chromatography (eluent: MeOH/DCM=1/20) to give 7-chloro-8-fluoro-1-((4-methoxybenzyl)thio)imidazo[1,5-a]pyridine (1.2 g, yield: 93%) as yellow oil. ESI-MS [M+H]$^+$: 323.0.

Synthesis of 7-chloro-8-fluoroimidazo[1,5-a]pyridine-1-sulfonyl chloride

To the mixture of 7-chloro-8-fluoro-1-((4-methoxybenzyl)thio)imidazo[1,5-a]pyridine (644 mg, 2.0 mmol) in AcOH/H$_2$O (4.5 mL/1.5 mL) was added NCS (266 mg, 2.0 mmol). After stirring at room temperature for 2 h, a second portion of NCS (266 mg, 2.0 mmol) was added. The reaction mixture was stirred at room temperature for another 2 h. Then the reaction was quenched with saturated aqueous NaHCO$_3$(50 mL) and extracted with DCM (50 mL×3). The combined organic layers were washed with brine (40 mL), dried over Na$_2$SO$_4$ and concentrated give crude 7-chloro-8- fluoroimidazo[1,5-a]pyridine-1-sulfonyl chloride (700 mg, crude) as a brown oil which was used in next step directly without further purification. ESI-MS [M+H]+: 269.0.

Synthesis of 7-chloro-N-((1-(((6-cyclopropylimidazo[1,2-a]pyridin-2-yl)methyl)-1H-1,2,3-triazol-4-yl)methyl)-8-fluoroimidazo[1,5-a]pyridine-1-sulfonamide

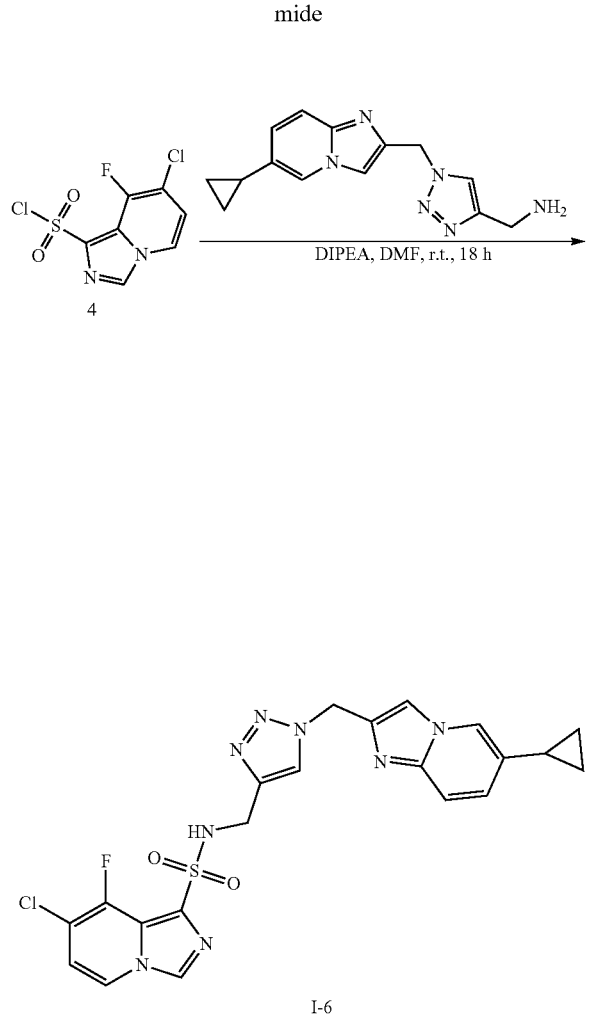

A mixture of 7-chloro-8-fluoroimidazo[1,5-a]pyridine-1-sulfonyl chloride (150 mg, 0.56 mmol), (1-(((6-cyclopropylimidazo[1,2-a]pyridin-2-yl)methyl)-1H-1,2,3-triazol-4-yl)methanamine (150 mg, 0.56 mmol) and DIPEA (217 mg, 1.68 mmol) in DMF (100 mL) was stirred at room temperature for 18 h. The reaction was quenched with saturated aqueous NaHCO$_3$(30 mL) and extracted with EtOAc (30 mL×3). The combined organic layers were washed with brine (30 mL), dried over Na$_2$SO$_4$ and concentrated to give the crude, which was purified by Prep-HPLC to give 7-chloro-N-((1-(((6-cyclopropylimidazo[1,2-a]pyridin-2-yl)methyl)-1H-1,2,3-triazol-4-yl)methyl)-8-fluoroimidazo[1,5-a]pyridine-1-sulfonamide (11 mg, 4% yield) as a light-yellow solid. ESI-MS [M+H]+: 501.1.

1H NMR (400 MHz, DMSO) δ 8.60 (s, 1H), 8.43-8.34 (m, 2H), 8.22 (s, 1H), 7.82 (d, J=7.9 Hz, 2H), 7.43 (d, J=9.2 Hz, 1H), 7.07-7.01 (m, 2H), 5.57 (s, 2H), 4.18 (s, 2H), 1.99-1.92 (m, 1H), 0.95-0.89 (m, 2H), 0.72-0.68 (m, 2H).

Example 7

7-chloro-N-(1-(1-(((6-cyclopropylimidazo[1,2-a]pyridin-2-yl)methyl)-1H-1,2,3-triazol-4-yl)ethyl)-8-fluoroimidazo[1,5-a]pyridine-1-sulfonamide (I-7)

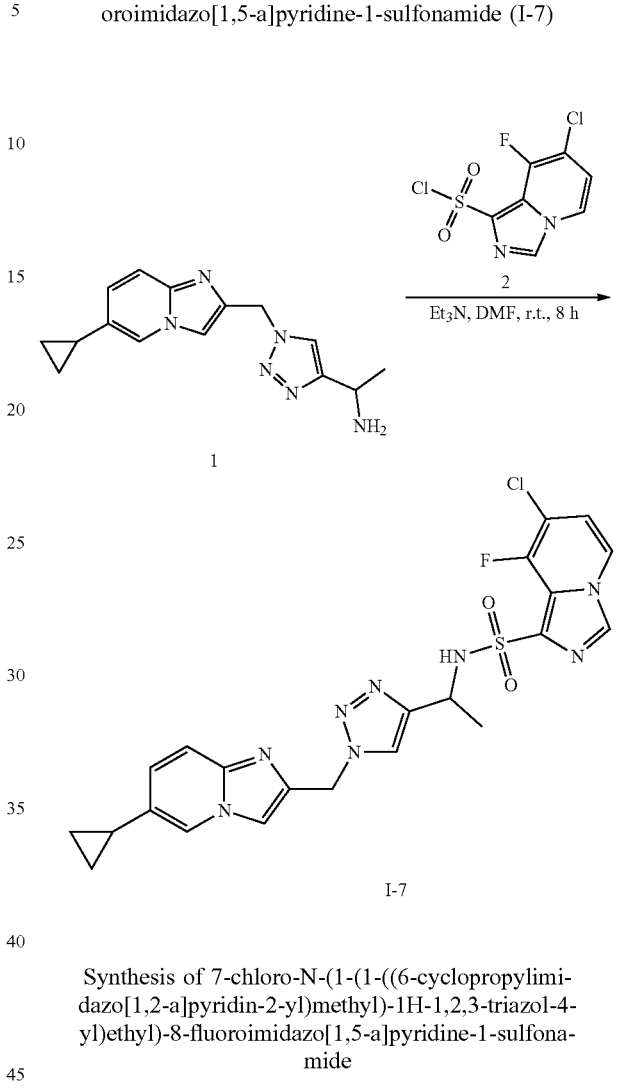

Synthesis of 7-chloro-N-(1-(1-(((6-cyclopropylimidazo[1,2-a]pyridin-2-yl)methyl)-1H-1,2,3-triazol-4-yl)ethyl)-8-fluoroimidazo[1,5-a]pyridine-1-sulfonamide To a solution of 1-(1-(((6-cyclopropylimidazo[1,2-a]pyridin-2-yl)methyl)-1H-1,2,3-triazol-4-yl)ethan-1-amine (70 mg, 0.248 mmol) and triethylamine (75 mg, 0.743 mmol) in DMF (3 mL) was added a solution of 7-chloro-8-fluoroimidazo[1,5-a]pyridine-1-sulfonyl chloride (100 mg, 0.373 mmol) in 3 mL DMF at 0° C. The reaction mixture was stirred at RT for 8 hours. Water (30 mL) was added and the mixture was extracted with EtOAc (50 mL×3). The combined organic layers were washed by brine (30 mL), dried over Na$_2$SO$_4$, and concentrated to give the crude which was purified by Prep-HPLC to afford 7-chloro-N-(1-(1-(((6-cyclopropylimidazo[1,2-a]pyridin-2-yl)methyl)-1H-1,2,3-triazol-4-yl)ethyl)-8-fluoroimidazo[1,5-a]pyridine-1-sulfonamide [1,5-a]pyridine-1-sulfonamide (5.4 mg, yield: 4.3%) as a white solid. ESI-MS: [M+H]+, 515.1, Purity: 97.25% (214 nm); 98.25%(254 nm).

1H NMR (400 MHz, DMSO) δ 8.52 (d, J=2.1 Hz, 1H), 8.37-8.35 (m, 2H), 8.19 (d, J=8.5 Hz, 1H), 7.81 (s, 1H), 7.67 (s, 1H), 7.45 (d, J=9.4 Hz, 1H), 7.07-7.01 (m, 2H), 5.62-5.46 (m, 2H), 4.59-4.53 (m, 1H), 1.97-1.91 (m, 1H), 1.33 (d, J=7.0 Hz, 3H), 0.94-0.91 (m, 2H), 0.71-0.67 (m, 2H).

67

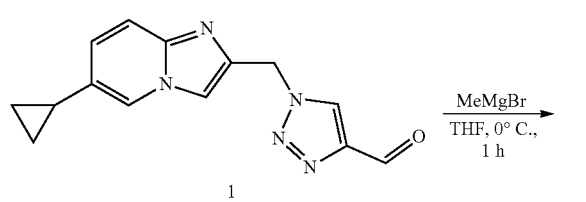

1

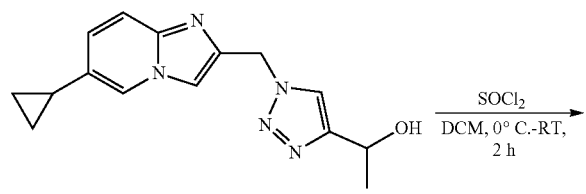

2

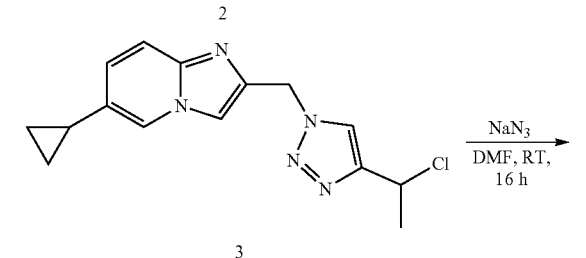

3

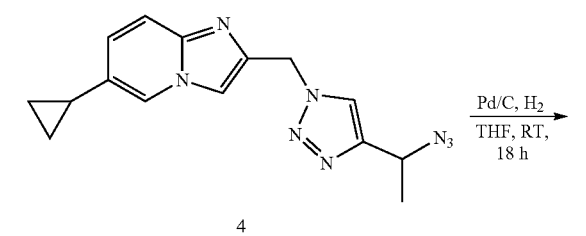

4

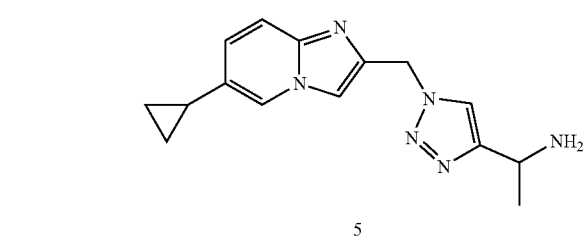

5

Synthesis of 1-(1-((6-cyclopropylimidazo[1,2-a]pyridin-2-yl)methyl)-1H-1,2,3-triazol-4-yl)ethan-1-ol

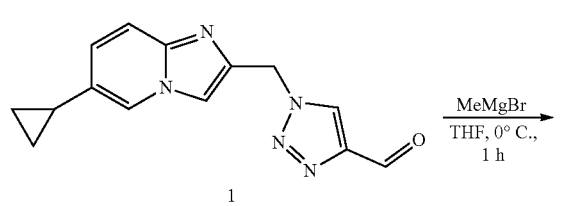

1

68

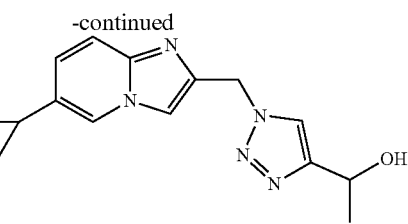

2

-continued

To a mixture of 1-((6-cyclopropylimidazo[1,2-a]pyridin-2-yl)methyl)-1H-1,2,3-triazole-4-carbaldehyde (2.0 g, 7.5 mmol) in THF (30 mL) was added MeMgBr (30.0 mL, 30.0 mmol) at 0° C. The mixture was stirred at 0° C. for 1 h. Then the reaction mixture was quenched with saturated aq. NH$_4$C$_1$ solution (50 mL) and extracted with EtOAc (30 mL×5). The combined organic layers were washed with brine (30 mL), dried over Na$_2$SO$_4$ and concentrated in vacuo. The residue was purified by flash column chromatography (MeOH/DCM from 0 to 5%) to afford 1-(1-((6-cyclopropylimidazo[1,2-a]pyridin-2-yl)methyl)-1H-1,2,3-triazol-4-yl)ethan-1-ol (1.5 g, yield: 71%) as a yellow oil. ESI-MS [M+H]$^+$: 284.1

Synthesis of 2-((4-(1-chloroethyl)-1H-1,2,3-triazol-1-yl)methyl)-6-cyclopropylimidazo[1,2-a]pyridine

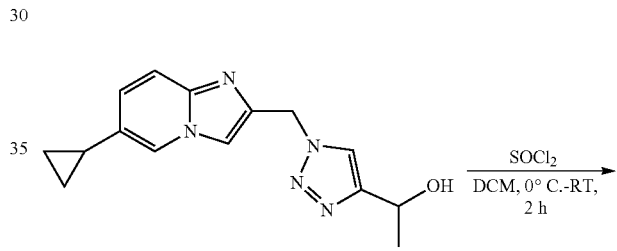

2

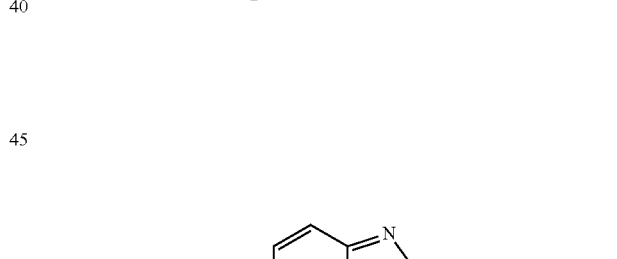

3

To a mixture of 1-(1-((6-cyclopropylimidazo[1,2-a]pyridin-2-yl)methyl)-1H-1,2,3-triazol-4-yl)ethan-1-ol (500 mg, 1.77 mmol) in DCM (10 mL) was added SOCl$_2$(1.0 mL) at 0° C. and the mixture was stirred at RT for 2 h. The reaction mixture was concentrated afford crude 2-((4-(1-chloroethyl)-1H-1,2,3-triazol-1-yl)methyl)-6-cyclopropylimidazo [1,2-a]pyridine (600 mg, crude) as a yellow oil, which was used in the next step directly without further purification. ESI-MS [M+H]$^+$: 302.1

Synthesis of 2-((4-(1-azidoethyl)-1H-1,2,3-triazol-1-yl)methyl)-6-cyclopropylimidazo[1,2-a]pyridine

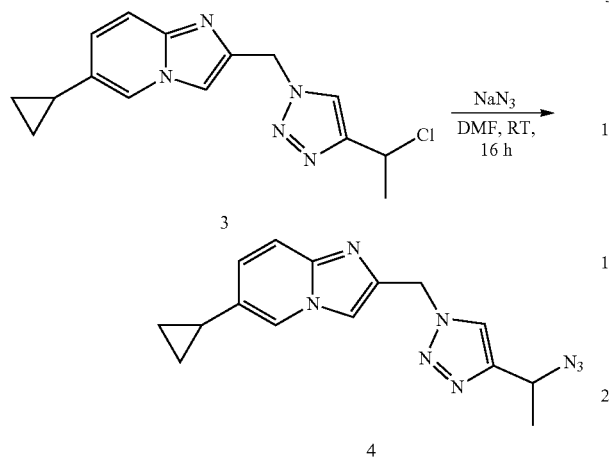

A mixture of 2-((4-(1-chloroethyl)-1H-1,2,3-triazol-1-yl)methyl)-6-cyclopropylimidazo[1,2-a]pyridine (600 mg, crude) and NaN₃ (344 mg, 5.30 mmol) in DMF (10 mL) was stirred at RT for 16 h. The reaction mixture was diluted with water (100 mL) and extracted with EtOAc (50 mL×3). The combined organic layer was washed with brine (30 mL), dried over Na₂SO₄ and concentrated in vacuo. The residue was purified by flash column chromatography (MeOH/DCM from 0 to 3%) to afford 2-((4-(1-azidoethyl)-1H-1,2,3-triazol-1-yl)methyl)-6-cyclopropylimidazo[1,2-a]pyridine (250 mg, yield: 46% over 2 steps) as a yellow oil. ESI-MS [M+H]⁺: 309.2.

Synthesis of 1-(1-(((6-cyclopropylimidazo[1,2-a]pyridin-2-yl)methyl)-1H-1,2,3-triazol-4-yl)ethan-1-amine

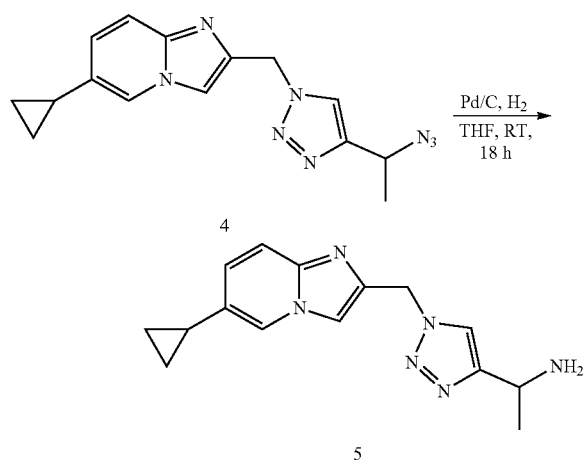

A mixture of 2-((4-(1-azidoethyl)-1H-1,2,3-triazol-1-yl)methyl)-6-cyclopropylimidazo[1,2-a]pyridine (250 mg, 0.81 mmol) and Pd/C (50 mg) in THF (10 mL) was stirred under hydrogen atmosphere at RT for 18 h. Upon completion, the reaction mixture was filtered and the filtrate was concentrated to afford crude 1-(1-((6-cyclopropylimidazo[1,2-a]pyridin-2-yl)methyl)-1H-1,2,3-triazol-4-yl)ethan-1-amine (150 mg, yield: 66%) as a yellow oil which was used in the next step directly without further purification. ESI-MS [M+H]⁺: 283.2

Example 8

N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (I-8)

Scheme 8

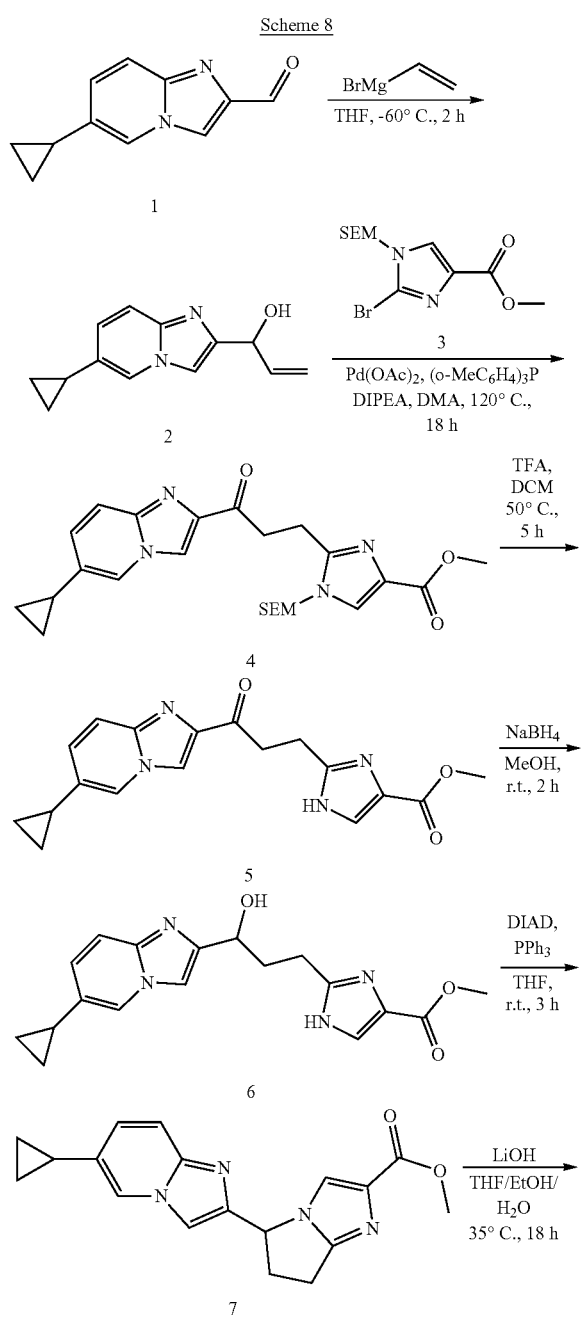

-continued

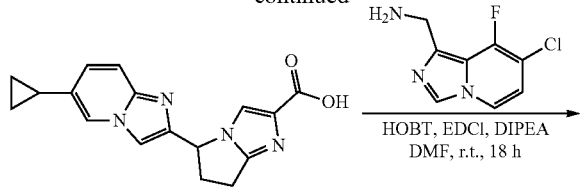

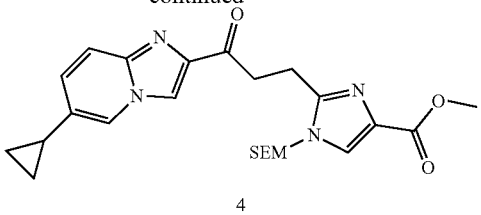

Synthesis of 1-(6-cyclopropylimidazo[1,2-a]pyridin-2-yl)prop-2-en-1-ol

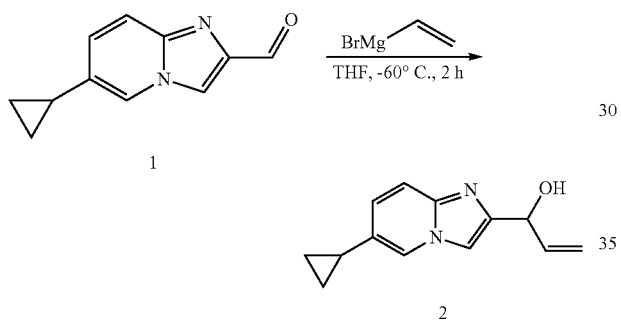

To the mixture of 6-cyclopropylimidazo[1,2-a]pyridine-2-carbaldehyde (1.86 g, 10.0 mmol) in THF (30 mL) was added vinylmagnesium bromide (15 mL, 15.0 mmol), maintaining a temperature below −60° C. The reaction mixture was stirred at −60° C. for 2 h, then quenched with saturated aqueous NH$_4$C$_1$ (100 mL) and extracted with EtOAc (50 mL×3). The combined organic layers were washed with brine (50 mL), dried over Na$_2$SO$_4$ and concentrated to give the crude, which was purified by flash column chromatography (eluent: DCM/MeOH=10/1) to give 1-(6-cyclopropylimidazo[1,2-a]pyridin-2-yl)prop-2-en-1-ol (1.6 g, yield: 75%) as a pale yellow solid. ESI-MS [M+H]$^+$: 215.2.

Synthesis of Methyl 2-(3-(6-cyclopropylimidazo[1,2-a]pyridin-2-yl)-3-oxopropyl)-1-((2-(trimethylsilyl)ethoxy)methyl)-1H-imidazole-4-carboxylate

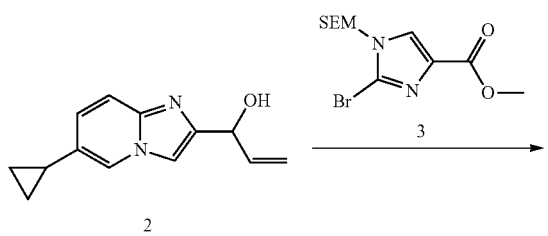

A mixture of 1-(6-cyclopropylimidazo[1,2-a]pyridin-2-yl)prop-2-en-1-ol (1.2 g, 5.6 mmol), methyl 2-bromo-1-((2-(trimethylsilyl)ethoxy)methyl)-1H-imidazole-4-carboxylate (2.25 g, 6.7 mmol), Pd(OAc)$_2$ (125 mg, 0.56 mmol), (o-MeC$_6$H$_4$)$_3$P (170 mg, 0.56 mmol) and DIPEA (2.2 g, 16.8 mmol) in DMA (20 mL) was degassed with N$_2$ and stirred at 120° C. for 18 h. The reaction mixture was cooled to room temperature and water (100 mL) was added. The mixture was extracted with EtOAc (50 mL×3). The combined organic layers were washed with brine (50 mL) and concentrated in vacuo to give the crude, which was purified by flash column chromatography (eluent: DCM/MeOH=15/1) to afford methyl 2-(3-(6-cyclopropylimidazo[1,2-a]pyridin-2-yl)-3-oxopropyl)-1-((2-(trimethylsilyl)ethoxy)methyl)-1H-imidazole-4-carboxylate as an off-white solid(900 mg, yield: 34%). ESI-MS [M+H]$^+$: 468.2.

Synthesis of methyl 2-(3-(6-cyclopropylimidazo[1,2-a]pyridin-2-yl)-3-oxopropyl)-1H-imidazole-4-carboxylate

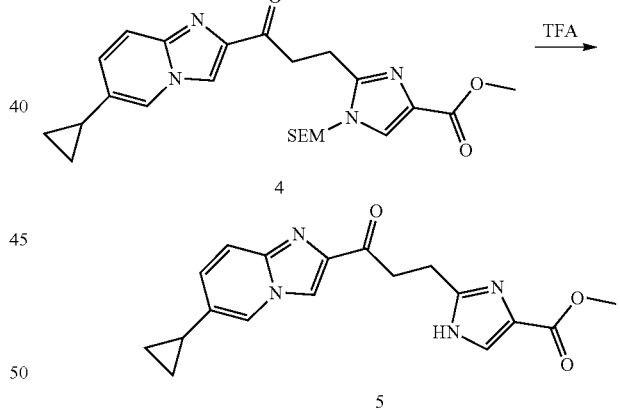

A mixture of methyl 2-(3-(6-cyclopropylimidazo[1,2-a]pyridin-2-yl)-3-oxopropyl)-1-((2-(trimethylsilyl)ethoxy)methyl)-1H-imidazole-4-carboxylate (500 mg, 1.07 mmol) in TFA/DCM (3.5 mL/10 mL) was stirred at 50° C. for 5 h. The reaction mixture was cooled to room temperature and concentrated to give a residue, which was diluted with saturated aqueous NaHCO$_3$(50 mL) and extracted with EtOAc (50 mL×3). The combined organic layers were washed with brine (50 mL), dried over Na$_2$SO$_4$, and concentrated in vacuo to give the crude, which was purified by flash column chromatography (eluent: DCM/MeOH=15/1) to afford methyl 2-(3-(6-cyclopropylimidazo[1,2-a]pyridin-2-yl)-3-oxopropyl)-1H-imidazole-4-carboxylate as a yellow solid(300 mg, yield: 83%). ESI-MS [M+H]$^+$: 338.1.

Synthesis of methyl 2-(3-(6-cyclopropylimidazo[1,2-a]pyridin-2-yl)-3-hydroxypropyl)-1H-imidazole-4-carboxylate

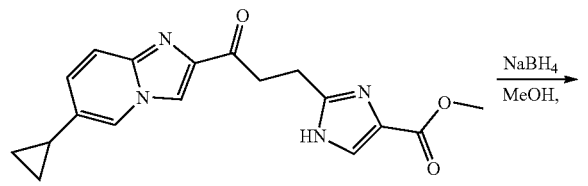

5

6

To a solution of methyl 2-(3-(6-cyclopropylimidazo[1,2-a]pyridin-2-yl)-3-oxopropyl)-1H-imidazole-4-carboxylate (0.3 g, 0.89 mmol) in MeOH (15 mL) at 0° C. was added NaBH₄ (67 mg, 1.78 mmol) slowly. The reaction mixture was stirred at room temperature for 2 h. Water (50 mL) was added and the mixture was and extracted with DCM/MeOH (10/1, 30 mL×3). The combined organic layers were washed with brine (20 mL) and concentrated in vacuo to give the crude, which was purified by flash column chromatography (eluent: DCM/MeOH=8/1) to afford methyl 2-(3-(6-cyclopropylimidazo[1,2-a]pyridin-2-yl)-3-hydroxypropyl)-1H-imidazole-4-carboxylate as a white solid (220 mg, yield: 73%). ESI-MS [M+H]⁺: 341.1.

Synthesis of methyl 5-(6-cyclopropylimidazo[1,2-a]pyridin-2-yl)-6,7-dihydro-5H-pyrrolo[1,2-a]imidazole-2-carboxylate

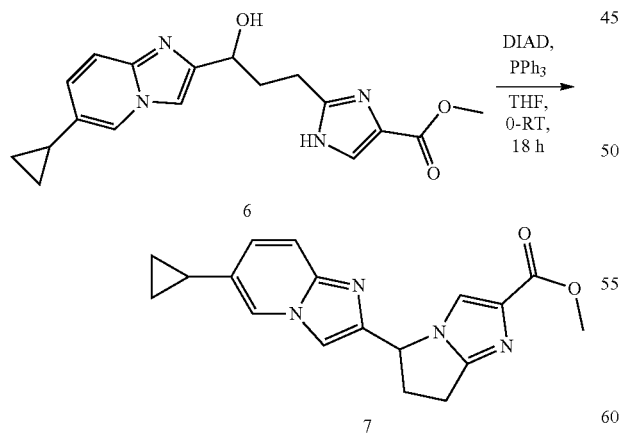

6

7

To a mixture of methyl 2-(3-(6-cyclopropylimidazo[1,2-a]pyridin-2-yl)-3-hydroxypropyl)-1H-imidazole-4-carboxylate (100 mg, 0.29 mmol) and PPh₃ (152 mg, 0.58 mmol) in THF (5 mL) at 0° C. was added DIAD (118 mg, 0.58 mmol). The mixture was warmed to room temperature and stirred for 3 h. The reaction was diluted with water (30 mL) and extracted with DCM/MeOH (10/1, 30 mL×3). The combined organic layers were washed with brine (30 mL) and concentrated to give the crude, which was purified by flash column chromatography (eluent: DCM/MeOH=10/1) to afford methyl 5-(6-cyclopropylimidazo[1,2-a]pyridin-2-yl)-6,7-dihydro-5H-pyrrolo[1,2-a]imidazole-2-carboxylate as a colorless oil (25 mg, yield: 26%). ESI-MS [M+H]⁺: 323.1.

Synthesis of 5-(6-cyclopropylimidazo[1,2-a]pyridin-2-yl)-6,7-dihydro-5H-pyrrolo[1,2-a]imidazole-2-carboxylicacid

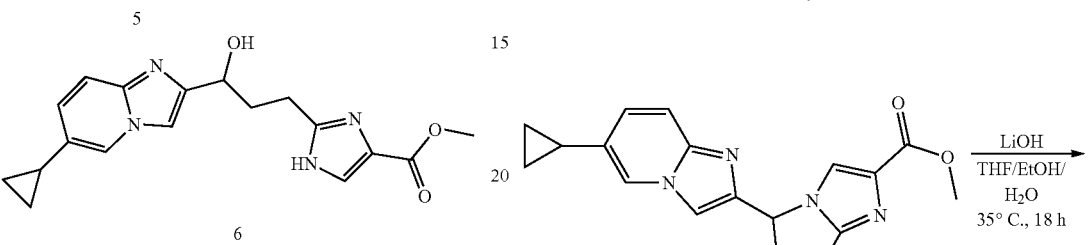

7

3

A mixture of methyl 5-(6-cyclopropylimidazo[1,2-a]pyridin-2-yl)-6,7-dihydro-5H-pyrrolo[1,2-a]imidazole-2-carboxylate (25 mg, 0.078 mmol) and LiOH.H₂O (16 mg, 0.390 mmol) in EtOH/THF/H₂O (1.5 mL/1.5 mL/0.5 mL) was stirred at 35° C. for 18 h. The reaction mixture was adjusted to pH 5 by addition of HCl (1N) and concentrated to afford 5-(6-cyclopropylimidazo[1,2-a]pyridin-2-yl)-6,7-dihydro-5H-pyrrolo[1,2-a]imidazole-2-carboxylic acid (40 mg, crude) as a white solid which was used into next step without further purification. ESI-MS [M+H]⁺: 309.2.

Synthesis of N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide

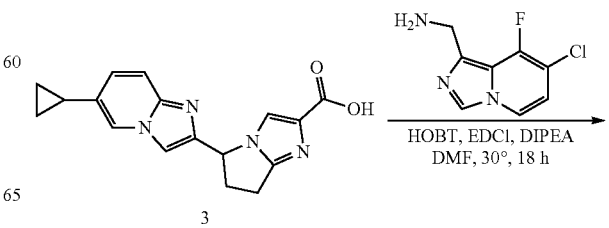

3

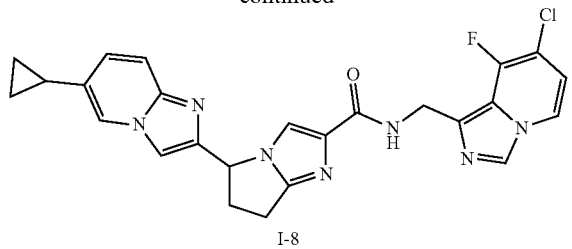

I-8

A mixture of 5-(6-cyclopropylimidazo[1,2-a]pyridin-2-yl)-6,7-dihydro-5H-pyrrolo[1,2-a]imidazole-2-carboxylic acid (40 mg, 0.13 mmol crude), (7-chloro-8-fluoroimidazo[1,5-a]pyridin-1-yl)methanamine hydrochloride (30 mg, 0.13 mmol), HOBT (17.5 mg, 0.13 mmol), EDCI (25 mg, 0.13 mmol) and DIPEA (50 mg, 0.39 mmol) in DMF (1 mL) was stirred at room temperature for 18 h. The reaction mixture was diluted with water (30 mL) and extracted with EtOAc (10 mL×3). The combined organic layers were washed with brine (20 mL), dried over Na$_2$SO$_4$, and concentrated in vacuo to give the crude, which was purified by prep-HPLC to afford N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide as white solid(10 mg, yield: 15.7%). ESI-MS [M+H]$^+$: 490.2.

1H NMR (400 MHz, DMSO) δ 8.45 (d, J=2.4 Hz, 1H), 8.32 (s, 1H), 8.21 (d, J=7.4 Hz, 1H), 7.96 (t, J=5.4 Hz, 1H), 7.73 (s, 1H), 7.45 (s, 1H), 7.41 (d, J=9.3 Hz, 1H), 7.02-6.99 (m, 1H), 6.76-6.74 (m, 1H), 5.58-5.54 (m, 1H), 4.66 (d, J=5.4 Hz, 2H), 2.93-2.82 (m, 3H), 2.78-2.70 (m, 1H), 1.94-1.89 (m, 1H), 0.92-0.89 (m, 2H), 0.70-0.65 (m, 2H).

Synthesis of methyl 2-bromo-1-((2-(trimethylsilyl)ethoxy)methyl)-1H-imidazole-4-carboxylate (Compound 3)

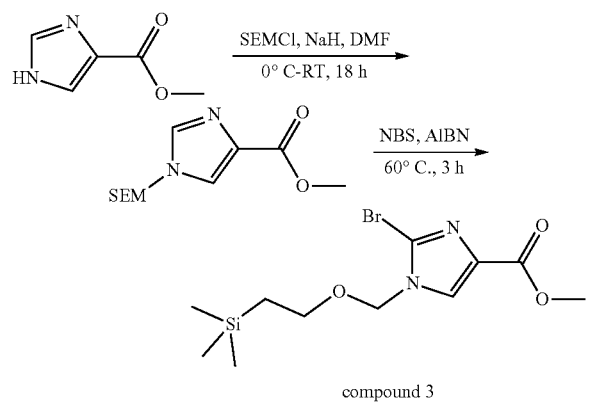

compound 3

Synthesis of methyl 1-((2-(trimethylsilyl)ethoxy)methyl)-1H-imidazole-4-carboxylate To a stirred solution of methyl 1H-imidazole-4-carboxylate (4 g, 31.75 mmol) in dry DMF (75 mL) was added NaH (1.46 g, 60% suspension in paraffin oil, 36.5 mmol) at 0° C. The reaction mixture was stirred at 0° C. for 30 min, then treated dropwise with (2-(chloromethoxy)ethyl)trimethylsilane (6.32 g, 38.1 mmol). The reaction was allowed to warm to room temperature and stirred for 18 h. The reaction was quenched with ice water (80 mL) and extracted with EtOAc (80 mL×3). The combined organic layers were washed with brine (100 mL), dried over Na$_2$SO$_4$, and concentrated in vacuo to give the crude, which was purified by silica gel chromatography (eluent: MeOH/DCM=1/20) to provide methyl 1-((2-(trimethylsilyl)ethoxy)methyl)-1H-imidazole-4-carboxylate (6.8 g, yield: 84%) as a white solid. ESI-MS [M+H]$^+$: 257.2.

Synthesis of methyl 2-bromo-1-((2-(trimethylsilyl)ethoxy)methyl)-1H-imidazole-4-carboxylate

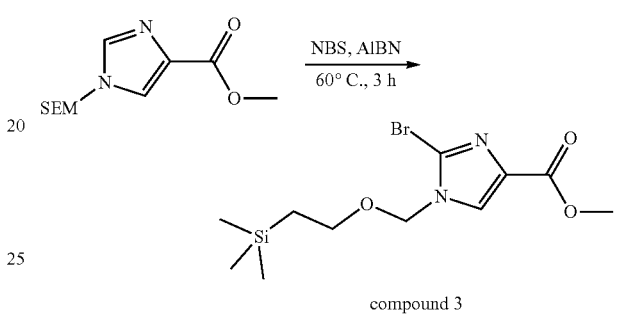

compound 3

To a stirred solution of methyl 1-((2-(trimethylsilyl)ethoxy)methyl)-1H-imidazole-4-carboxylate (5.0 g, 19.5 mmol) in carbon tetrachloride (50 mL) was added NBS (3.47 g, 19.5 mmol) and AIBN (160 mg, 5 mol %) at room temperature. The reaction mixture was heated at 60° C. for 3 h, then cooled to room temperature and filtered through a small pad of celite. The filtrate was concentrated in vacuo to give a light yellow colored residue, which was dissolved in EtOAc (100 mL) and washed with 10% aqueous NaHCO$_3$ (100 mL) solution. The organic layer was washed with brine (70 mL), dried over Na$_2$SO$_4$ and concentrated to give crude compound. The crude material was purified by silica gel chromatography (eluent: PE/EtOAc=2/1) to provide methyl 2-bromo-1-((2-(trimethylsilyl)ethoxy)methyl)-1H-imidazole-4-carboxylate (4 g, yield: 61.5%). ESI-MS [M+H]$^+$: 355.2.

Example 9

N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-3-carboxamide (I-9)

Scheme 9

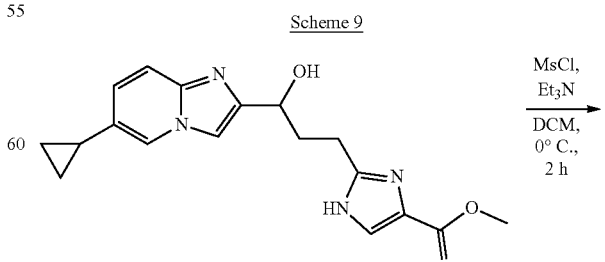

1

77

-continued

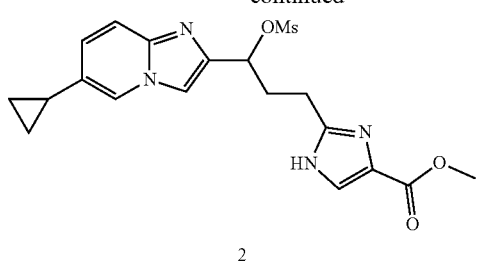
2

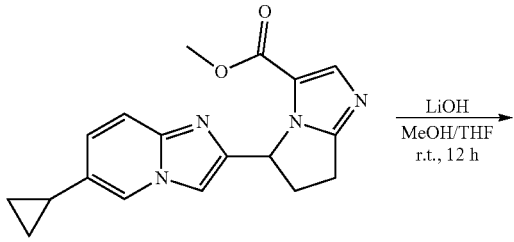
3

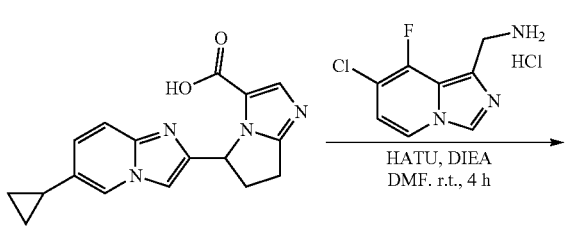
I-9

Synthesis of methyl 2-(3-(6-cyclopropylimidazo[1,2-a]pyridin-2yl)-3-((methylsulfonyl)oxy)propyl)-1H-imidazole-4-carboxylate

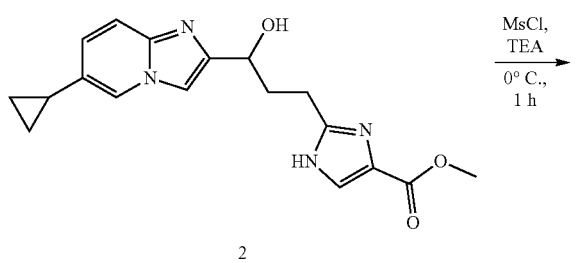
2

78

-continued

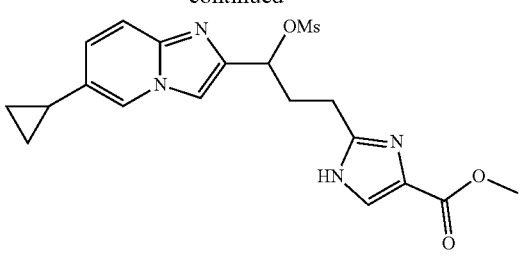
3

To a solution of methyl 2-(3-(6-cyclopropylimidazo[1,2-a]pyridin-2-yl)-3-hydroxypropyl)-1H-imidazole-4-carboxylate (200 mg, 0.59 mmol) in DCM (4 mL) at 0° C. was added triethylamine (119.3 mg, 1.18 mmol) and MsCl (101.2 g, 0.88 mmol). After stirring at 0° C. for 2 h, the reaction was concentrated in vacuo to give methyl 2-(3-(6-cyclopropylimidazo[1,2-a]pyridin-2-yl)-3-((methylsulfonyl)oxy)propyl)-1H-imidazole-4-carboxylate (240 mg, yield: 98%) as a black solid which was used in the subsequent step without further purification. ESI-MS [M+H]+: 419.1.

Synthesis of Methyl 5-(6-cyclopropylimidazo[1,2-a]pyridin-2-yl)-6,7-dihydro-5H-pyrrolo[1,2-a]imidazole-3-carboxylate

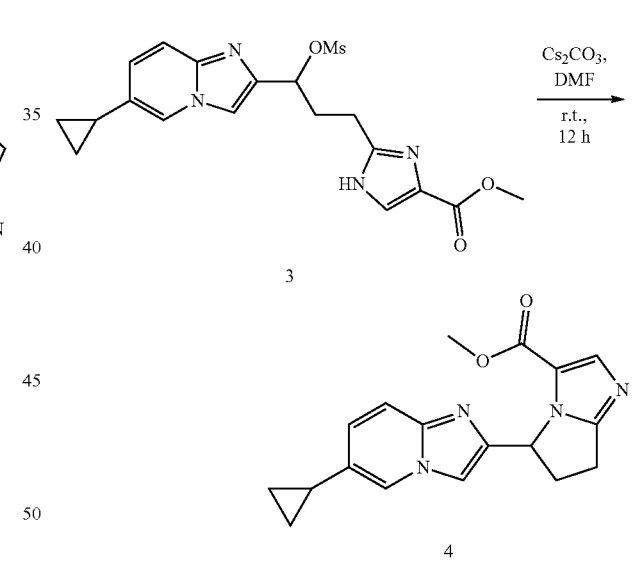

A mixture of methyl 2-(3-(6-cyclopropylimidazo[1,2-a]pyridin-2-yl)-3-((methylsulfonyl)oxy)propyl)-1H-imidazole-4-carboxylate (240 mg, 0.57 mmol) and Cs$_2$CO$_3$ (557 mg, 1.71 mmol) in DMF (15 mL) was stirred at room temperature for 12 h. Water (30 mL) was added and the mixture was extracted with EtOAc (50 mL×3). The combined organic layers were washed with brine, dried over Na$_2$SO$_4$, and concentrated in vacuo to give the crude, which was purified by silica gel chromatography (EtOAc/PE=1/1) to give methyl 5-(6-cyclopropylimidazo[1,2-a]pyridin-2-yl)-6,7-dihydro-5H-pyrrolo[1,2-a]imidazole-3-carboxylate (102 mg, yield: 55.7%) as a yellow solid. ESI-MS [M+H]+: 323.1.

Synthesis of 5-(6-cyclopropylimidazo[1,2-a]pyridin-2-yl)-6,7-dihydro-5H-pyrrolo[1,2-a]imidazole-3-carboxylic Acid

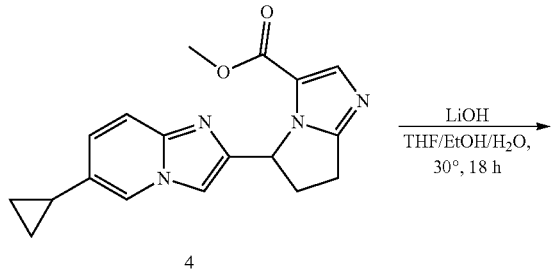

To a solution of methyl 5-(6-cyclopropylimidazo[1,2-a]pyridin-2-yl)-6,7-dihydro-5H-pyrrolo[1,2-a]imidazole-3-carboxylate (102 mg, 0.32 mmol) in MeOH (1 mL) and THF (1 mL) was added LiOH (31.6 mg, 1.32 mmol) and H$_2$O (0.5 mL). The reaction mixture was stirred at room temperature for 12 h. The mixture was adjusted pH 5 with 1N HCl and then extracted with EtOAc (30 mL×3). The combined organic layers were concentrated to give 5-(6-cyclopropylimidazo[1,2-a]pyridin-2-yl)-6,7-dihydro-5H-pyrrolo[1,2-a]imidazole-3-carboxylic acid (65 mg, yield: 67%) as a white solid which was used in the subsequent reaction without further purification. ESI-MS [M+H]$^+$: 309.1.

Synthesis of N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide

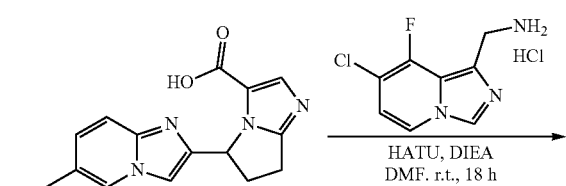

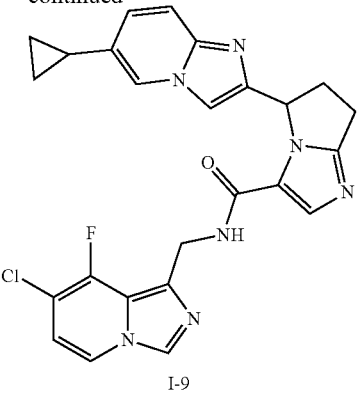

To a solution of 5-(6-cyclopropylimidazo[1,2-a]pyridin-2-yl)-6,7-dihydro-5H-pyrrolo[1,2-a]imidazole-3-carboxylic acid (65 mg, 0.21 mmol) in DMF (2 mL) was added (7-chloro-8-fluoroimidazo[1,5-a]pyridin-1-yl)methanamine hydrochloride (64.7 mg, 0.27 mmol), HATU (102.6 mg, 0.27 mmol), and DIPEA (387 mg, 3.0 mmol). The reaction mixture was stirred at room temperature for 4 h. Water (20 mL) was added and the mixture was extracted with EtOAc (20 mL×3). The combined organic layers were washed with brine (20 mL), dried over Na$_2$SO$_4$, filtered and concentrated to give the crude, which was purified by Prep-HPLC to give N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (32 mg, yield: 50%) as a white solid. ESI-MS [M+H]$^+$: 490.2. Purity: 98.98% (214 nm), 99.54% (254 nm).

1H NMR (400 MHz, DMSO) δ 8.48 (t, J=5.3 Hz, 1H), 8.43 (d, J=2.4 Hz, 1H), 8.26 (s, 1H), 8.19 (d, J=7.4 Hz, 1H), 7.58 (s, 1H), 7.41 (s, 1H), 7.34 (d, J=9.3 Hz, 1H), 6.98-6.95 (m, 1H), 6.78-6.71 (m, 1H), 5.86 (d, J=7.6 Hz, 1H), 4.68-4.65 (m, 1H), 4.51-4.46 (m, 1H), 3.02-2.88 (m, 2H), 2.81-2.71 (m, 1H), 2.69-2.59 (m, 1H), 1.95-1.88 (m, 1H), 0.95-0.86 (m, 2H), 0.71-0.62 (m, 2H).

Example 10

N-((7-cyanoimidazo[1,5-a]pyridin-1-yl)methyl)-1-((6-cyclopropylimidazo[1,2-a]pyridin-2-yl)methyl)-1H-pyrazole-4-carboxamide(I-10)

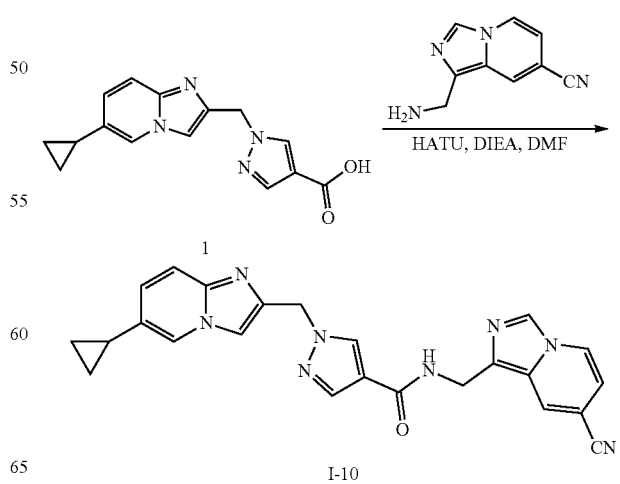

To a solution of 1-((6-cyclopropylimidazo[1,2-a]pyridin-2-yl)methyl)-1H-pyrazole-4-carboxylic acid (60 mg, 0.21 mmol), 1-(aminomethyl)imidazo[1,5-a]pyridine-7-carbonitrile (55 mg, 0.32 mmol) and HATU (120 mg, 0.31 mmol) in DMF (2 mL) was added DIPEA (81 mg, 0.63 mmol). The resulting reaction was stirred at room temperature for 12 h. H$_2$O (25 mL) was added and the mixture was extracted with EtOAc (15 mL×3). The combined organic layers were washed with brine (15 mL), dried over Na$_2$SO$_4$, and concentrated in vacuo to give the crude product which was purified by Prep-TLC (DMC/MeOH=10/1) to give N-((7-cyanoimidazo[1,5-a]pyridin-1-yl)methyl)-1-((6-cyclopropylimidazo[1,2-a]pyridin-2-yl)methyl)-1H-pyrazole-4-carboxamide as a white solid (22 mg, yield: 24%). ESI-MS [M+H]$^+$: 437.2.

1H NMR (400 MHz, DMSO) δ 8.65 (t, J=5.7 Hz, 1H), 8.50 (s, 1H), 8.44 (s, 1H), 8.40-8.37 (m, 1H), 8.32 (s, 1H), 8.21 (s, 1H), 7.86 (s, 1H), 7.72 (s, 1H), 7.39 (d, J=9.3 Hz, 1H), 7.01-6.97 (m, 1H), 6.85-6.81 (m, 1H), 5.39 (s, 2H), 4.63 (d, J=5.7 Hz, 2H), 1.94-1.88 (m, 1H), 0.93-0.88 (m, 2H), 0.68-0.64 (m, 2H).

Example 11

1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (I-11)

Scheme 11

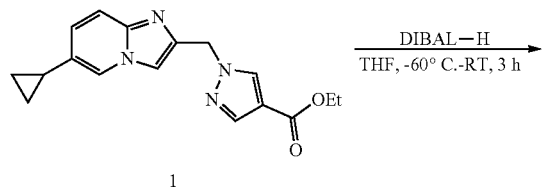

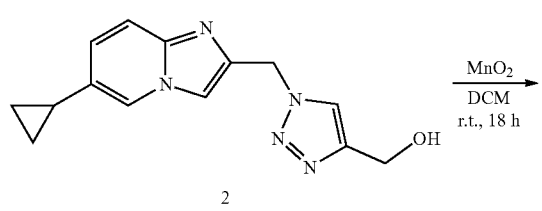

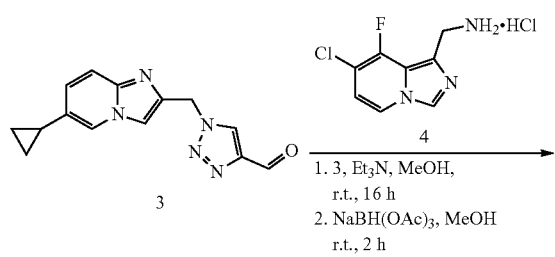

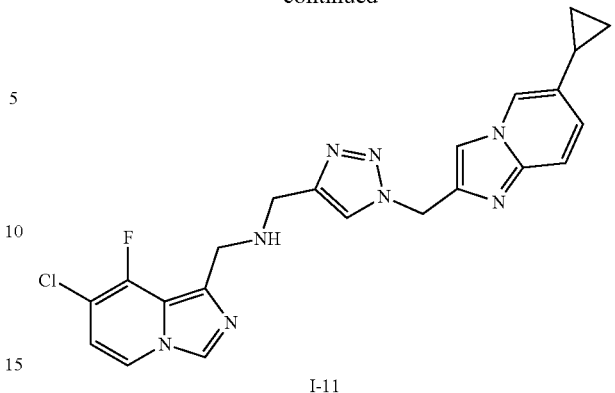

I-11

Synthesis of (1-((6-cyclopropylimidazo[1,2-a]pyridin-2-yl)methyl)-1H-1,2,3-triazol-4-yl)methanol

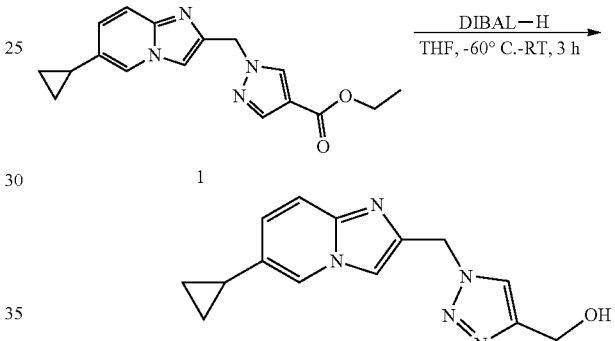

To a solution of ethyl 1-((6-cyclopropylimidazo[1,2-a]pyridin-2-yl)methyl)-1H-1,2,3-triazole-4-carboxylate (10.0 g, 33.7 mmol) in THF (100 mL) was added DIBAL-H (67.3 mL, 67.3 mmol) at −60° C. The mixture was stirred at room temperature for 3 h and then quenched with saturated aq. NaHCO$_3$ solution (300 mL) and extracted with EtOAc (150 mL×3). The combined organic layers were washed with brine (200 mL), dried over Na$_2$SO$_4$ and concentrated in vacuo. The residue was purified by flash column chromatography (PE/EtOAc from 0 to 20%) to give (1-((6-cyclopropylimidazo[1,2-a]pyridin-2-yl)methyl)-1H-1,2,3-triazol-4-yl)methanol (7.5 g, yield: 82%) as an off-white solid. ESI-MS [M+H]$^+$: 270.1

Synthesis of 1-((6-cyclopropylimidazo[1,2-a]pyridin-2-yl)methyl)-1H-1,2,3-triazole-4-carbaldehyde

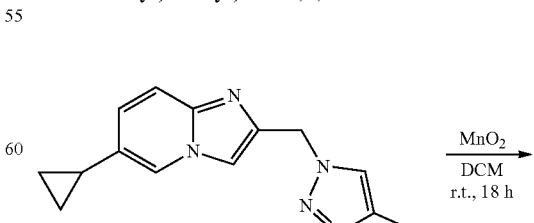

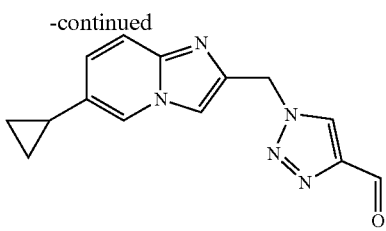

A mixture of (1-((6-cyclopropylimidazo[1,2-a]pyridin-2-yl)methyl)-1H-1,2,3-triazol-4-yl)methanol (300 mg, 1.12 mmol) and MnO₂ (963 mg, 11.2 mmol) in DCM (10 mL) was stirred at room temperature for 18 h. The reaction mixture was then filtered and concentrated in vacuo to give 1-((6-cyclopropylimidazo[1,2-a]pyridin-2-yl)methyl)-1H-1,2,3-triazole-4-carbaldehyde (220 mg, yield: 74%) as a yellow solid which was used in the next step without purification. ESI-MS [M+H]⁺: 268.1

Synthesis of 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine

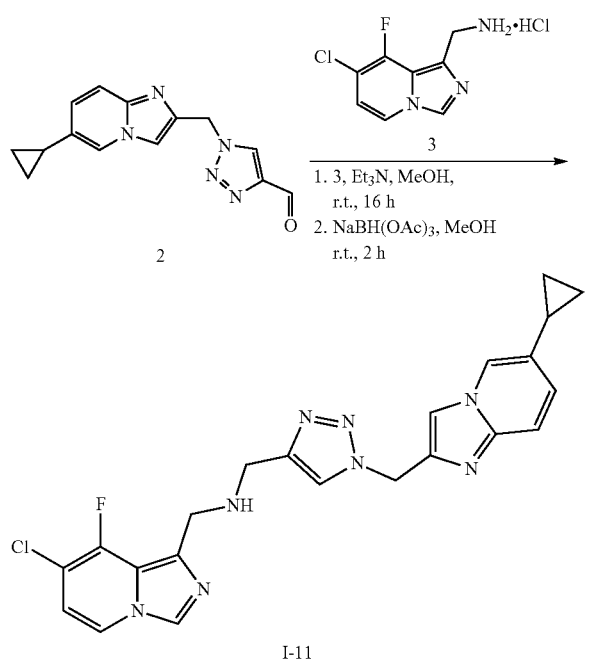

A mixture of 1-((6-cyclopropylimidazo[1,2-a]pyridin-2-yl)methyl)-1H-1,2,3-triazole-4-carbaldehyde (100 mg, 0.37 mmol), (7-chloro-8-fluoroimidazo[1,5-a]pyridin-1-yl)methanamine hydrochloride (88 mg, 0.37 mmol) and triethylamine (37 mg, 0.37 mmol) in MeOH (5 mL) was stirred at room temperature for 16 h. NaBH(OAc)₃ (157 mg, 0.74 mmol) was added and the mixture was stirred at room temperature for another 2 h. The reaction was quenched with water (50 mL) and extracted with ethyl acetate (30 mL×3). The combined organic layers were washed with brine (30 mL), dried over Na₂SO₄ and concentrated in vacuo. The residue was purified by Prep-TLC (MeOH/DCM=1/15) to give 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (5.5 mg, yield: 3.3%) as a white solid. ESI-MS [M+H]⁺: 451.1.

1H NMR (400 MHz, DMSO) δ 8.44 (d, J=2.1 Hz, 1H), 8.34 (s, 1H), 8.19 (d, J=7.4 Hz, 1H), 7.92 (s, 1H), 7.79 (s, 1H), 7.41 (d, J=9.3 Hz, 1H), 7.00 (d, J=9.4 Hz, 1H), 6.73 (t, J=6.9 Hz, 1H), 5.62 (s, 2H), 3.92 (s, 2H), 3.74 (s, 2H), 1.97-1.88 (m, 1H), 0.97-0.87 (m, 2H), 0.72-0.62 (m, 2H).

Example 12

N-((7-chloro-8-fluoroimidazo[1,5-a]pyridin-1-yl)methyl)-1-(1-((6-cyclopropylimidazo[1,2-a]pyridin-2-yl)methyl)-1H-1,2,3-triazol-4-yl)ethan-1-amine (I-12)

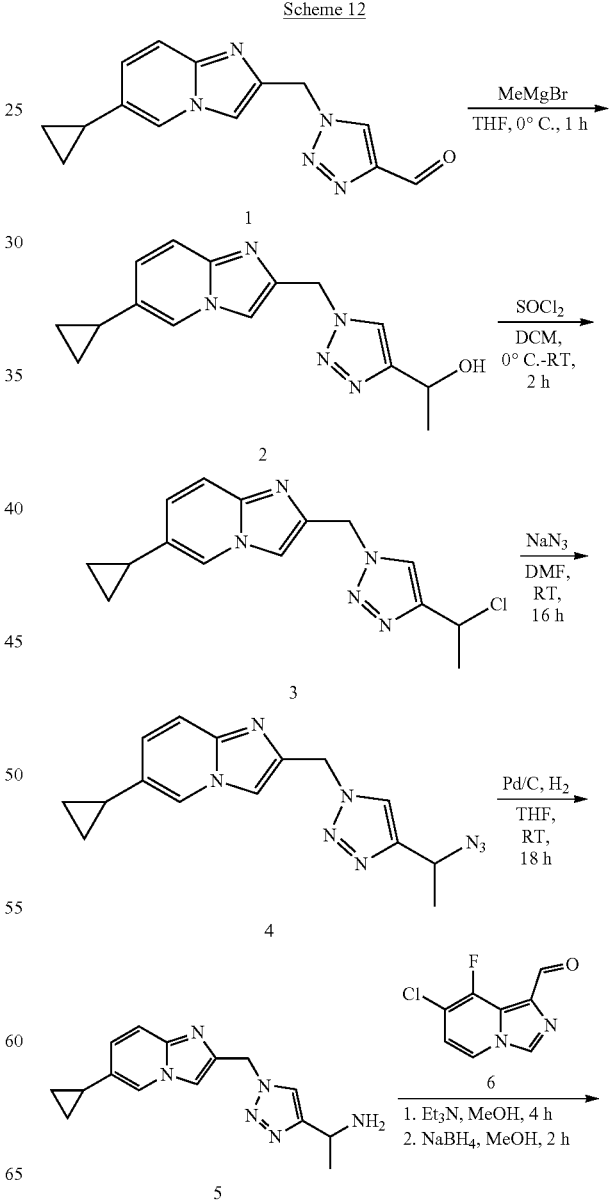

-continued

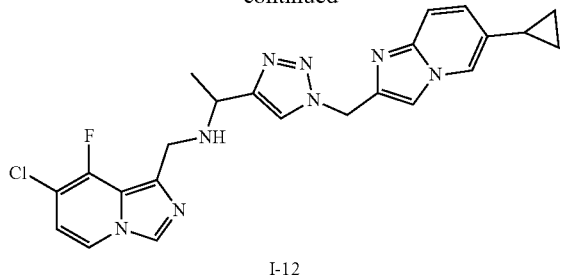

I-12

Synthesis of 1-(1-(((6-cyclopropylimidazo[1,2-a]pyridin-2-yl)methyl)-1H-1,2,3-triazol-4-yl)ethan-1-ol

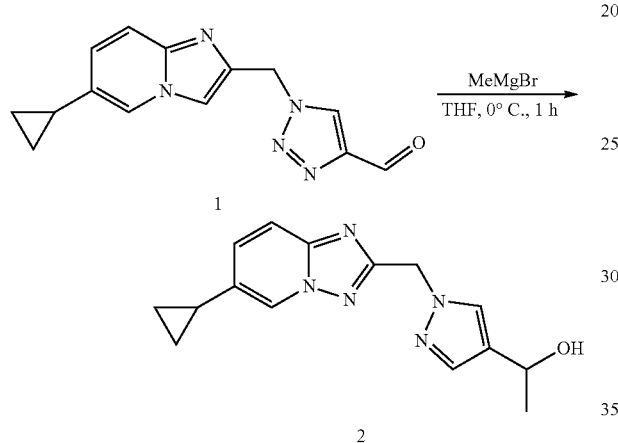

To a mixture of 1-((6-cyclopropylimidazo[1,2-a]pyridin-2-yl)methyl)-1H-1,2,3-triazole-4-carbaldehyde (2.0 g, 7.5 mmol) in THF (30 mL) was added MeMgBr (30.0 mL, 30.0 mmol) at 0° C. The mixture was stirred at 0° C. for 1 h. Then the reaction mixture was quenched with saturated aq. NH$_4$C$_1$ solution (50 mL) and extracted with EtOAc (30 mL×5). The combined organic layers were washed with brine (30 mL), dried over Na$_2$SO$_4$ and concentrated in vacuo. The residue was purified by flash column chromatography (MeOH/DCM from 0 to 5%) to afford 1-(1-(((6-cyclopropylimidazo[1,2-a]pyridin-2-yl)methyl)-1H-1,2,3-triazol-4-yl)ethan-1-ol (1.5 g, yield: 71%) as a yellow oil. ESI-MS [M+H]$^+$: 284.1

Synthesis of 2-((4-(1-chloroethyl)-1H-1,2,3-triazol-1-yl)methyl)-6-cyclopropylimidazo[1,2-a]pyridine

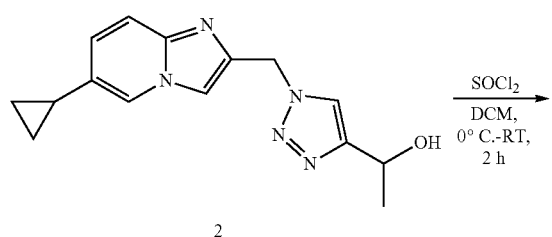

-continued

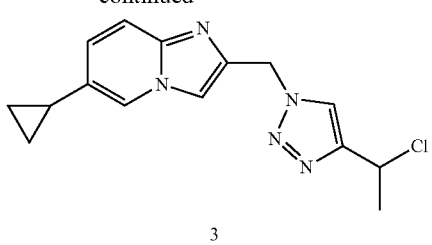

To a mixture of 1-(1-(((6-cyclopropylimidazo[1,2-a]pyridin-2-yl)methyl)-1H-1,2,3-triazol-4-yl)ethan-1-ol (500 mg, 1.77 mmol) in DCM (10 mL) was added SOCl$_2$(1.0 mL) at 0° C. and the mixture was stirred at RT for 2 h. The reaction mixture was concentrated afford crude 2-((4-(1-chloroethyl)-1H-1,2,3-triazol-1-yl)methyl)-6-cyclopropylimidazo[1,2-a]pyridine (600 mg, crude) as a yellow oil, which was used in the next step directly without further purification. ESI-MS [M+H]$^+$: 302.1 Synthesis of 2-((4-(1-azidoethyl)-1H-1,2,3-triazol-1-yl)methyl)-6-cyclopropylimidazo[1,2-a]pyridine

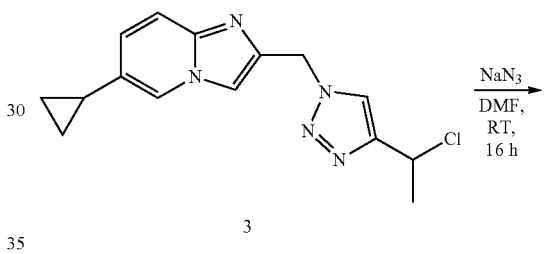

A mixture of 2-((4-(1-chloroethyl)-1H-1,2,3-triazol-1-yl)methyl)-6-cyclopropylimidazo[1,2-a]pyridine (600 mg, crude) and NaN$_3$ (344 mg, 5.30 mmol) in DMF (10 mL) was stirred at RT for 16 h. The reaction mixture was diluted with water (100 mL) and extracted with EtOAc (50 mL×3). The combined organic layer was washed with brine (30 mL), dried over Na$_2$SO$_4$ and concentrated in vacuo. The residue was purified by flash column chromatography (MeOH/DCM from 0 to 3%) to afford 2-((4-(1-azidoethyl)-1H-1,2,3-triazol-1-yl)methyl)-6-cyclopropylimidazo[1,2-a]pyridine (250 mg, yield: 46% over 2 steps) as a yellow oil. ESI-MS [M+H]$^+$: 309.2

Synthesis of 1-(1-(((6-cyclopropylimidazo[1,2-a]pyridin-2-yl)methyl)-1H-1,2,3-triazol-4-yl)ethan-1-amine

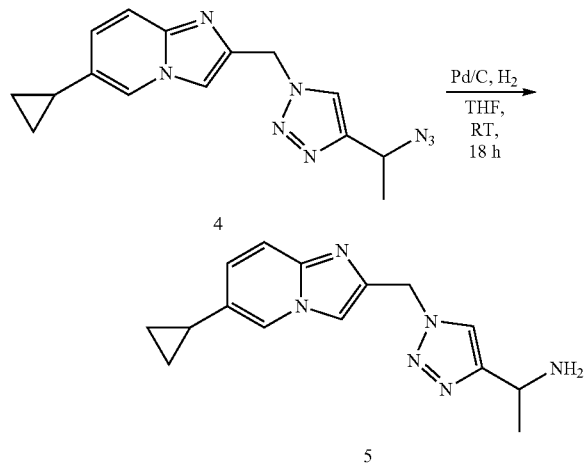

A mixture of 2-((4-(1-azidoethyl)-1H-1,2,3-triazol-1-yl)methyl)-6-cyclopropylimidazo[1,2-a]pyridine (250 mg, 0.81 mmol) and Pd/C (50 mg) in THF (10 mL) was stirred under hydrogen atmosphere at RT for 18 h. Upon completion, the reaction mixture was filtered and the filtrate was concentrated to afford crude 1-(1-(((6-cyclopropylimidazo[1,2-a]pyridin-2-yl)methyl)-1H-1,2,3-triazol-4-yl)ethan-1-amine (150 mg, yield: 66%) as a yellow oil which was used in the next step directly without further purification. ESI-MS [M+H]$^+$: 283.2

Synthesis of N-((7-chloro-8-fluoroimidazo[1,5-a]pyridin-1-yl)methyl)-1-(1-(((6-cyclopropylimidazo[1,2-a]pyridin-2-yl)methyl)-1H-1,2,3-triazol-4-yl)ethan-1-amine

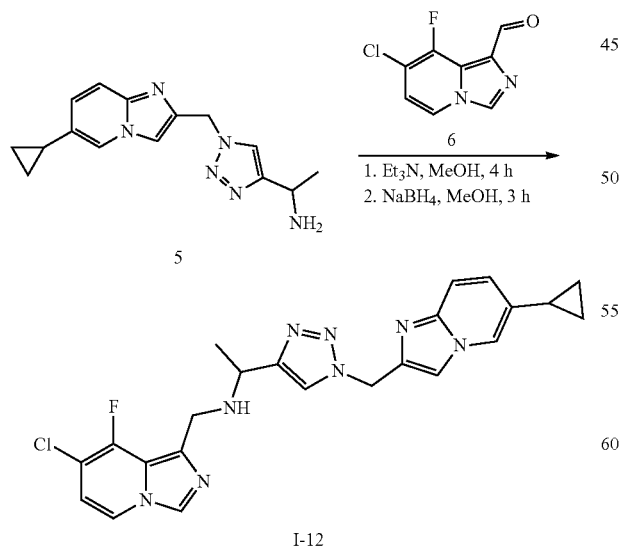

To a solution of 1-(1-(((6-cyclopropylimidazo[1,2-a]pyridin-2-yl)methyl)-1H-1,2,3-triazol-4-yl)ethan-1-amine (80 mg, 0.284 mmol) in MeOH (4 mL) was added 7-chloro-8-fluoroimidazo[1,5-a]pyridine-1-carbaldehyde (51 mg, 0.256 mmol) and triethylamine (57.5 mg, 0.568 mmol). The mixture was stirred at RT for 4 h. NaBH$_4$ (11 mg, 0.291 mmol) was added and the reaction mixture was stirred at RT for another 3 h. Water (40 mL) was added and the mixture was extracted with EA (30 ml×3). The combined organic layers were washed with brine (20 mL), dried over Na$_2$SO$_4$ and concentrated. The crude product was purified by Prep-TLC (DCM:MeOH=10:1) to give N-((7-chloro-8-fluoroimidazo[1,5-a]pyridin-1-yl)methyl)-1-(1-(((6-cyclopropylimidazo[1,2-a]pyridin-2-yl)methyl)-1H-1,2,3-triazol-4-yl)ethan-1-amine (18 mg, yield: 13.6%) as a yellow solid. ESI-MS [M+H]$^+$: 465.2

1H NMR (400 MHz, DMSO) δ 8.42 (d, J=2.4 Hz, 1H), 8.35 (s, 1H), 8.17 (d, J=7.4 Hz, 1H), 7.90 (s, 1H), 7.79 (s, 1H), 7.42 (d, J=9.3 Hz, 1H), 7.04-6.98 (m, 1H), 6.74-6.69 (m, 1H), 5.62 (s, 2H), 3.96-3.89 (m, 1H), 3.86 (s, 2H), 1.97-1.88 (m, 1H), 1.31 (d, J=6.6 Hz, 3H), 0.95-0.89 (m, 2H), 0.70-0.64 (m, 2H).

Example 13

2-(7-chloroimidazo[1,5-a]pyridin-1-yl)-N-(1-(1-(((6-cyclopropylimidazo[1,2-a]pyridin-2-yl)methyl)-1H-1,2,3-triazol-4-yl)ethyl)acetamide (I-13)

Synthesis of 2-(7-chloroimidazo[1,5-a]pyridin-1-yl)-N-(1-(1-(((6-cyclopropylimidazo[1,2-a]pyridin-2-yl)methyl)-1H-1,2,3-triazol-4-yl)ethyl)acetamide

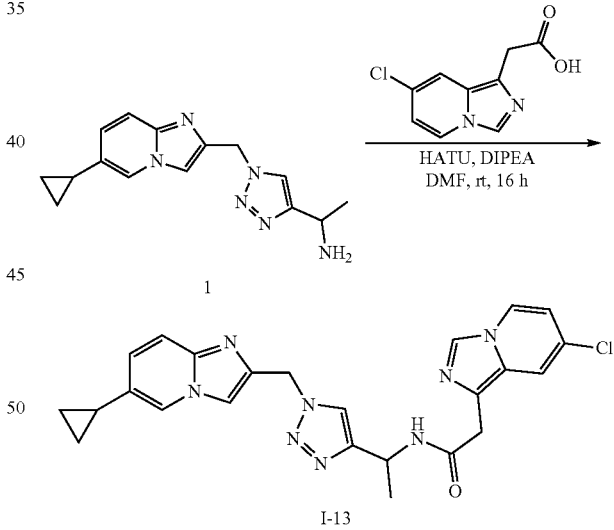

The mixture of 1-(1-(((6-cyclopropylimidazo[1,2-a]pyridin-2-yl)methyl)-1H-1,2,3-triazol-4-yl)ethan-1-amine (37.1 mg, 0.131 mmol), 2-(7-chloroimidazo[1,5-a]pyridin-1-yl)acetic acid (60 mg, 0.285 mmol), HATU (100.07 mg, 0.263 mmol), DIPEA (114.2 mg, 0.885 mmol) in DMF (4 mL) was stirred at rt for 16 h. Water (50 mL) was added and the mixture was extracted with EtOAc (50 mL×3). The combined organic layers were washed with brine (30 mL) and concentrated. The residue was purified by Prep-HPLC to give 2-(7-chloroimidazo[1,5-a]pyridin-1-yl)-N-(1-(1-(((6-cyclopropylimidazo[1,2-a]pyridin-2-yl)methyl)-1H-1,2,3- triazol-4-yl)ethyl)acetamide (40 mg, yield: 47.7%) as a white solid. ESI-MS [M+H]⁺: 475.2.

1H NMR (400 MHz, DMSO) δ 8.45 (d, J=8.2 Hz, 1H), 8.36 (s, 1H), 8.31-8.24 (m, 2H), 7.90 (s, 1H), 7.83 (s, 1H), 7.75-7.70 (m, 1H), 7.42 (d, J=9.3 Hz, 1H), 7.05-6.98 (m, 1H), 6.65-6.58 (m, 1H), 5.62 (s, 2H), 5.06-4.97 (m, 1H), 3.65 (s, 2H), 1.98-1.89 (m, 1H), 1.39 (d, J=7.0 Hz, 3H), 0.95-0.89 (m, 2H), 0.71-0.65 (m, 2H).

Example 14

Methyl 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (I-14)

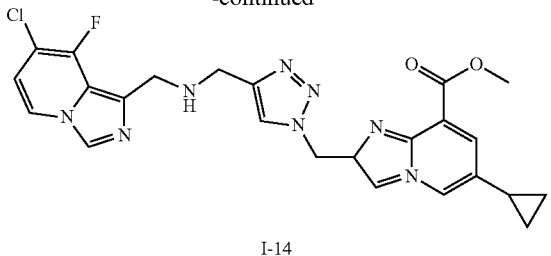

I-14

Synthesis of Methyl 1-((8-bromo-6-cyclopropylimidazo[1,2-a]pyridin-2-yl)methyl)-1H-1,2,3-triazole-4-carboxylate

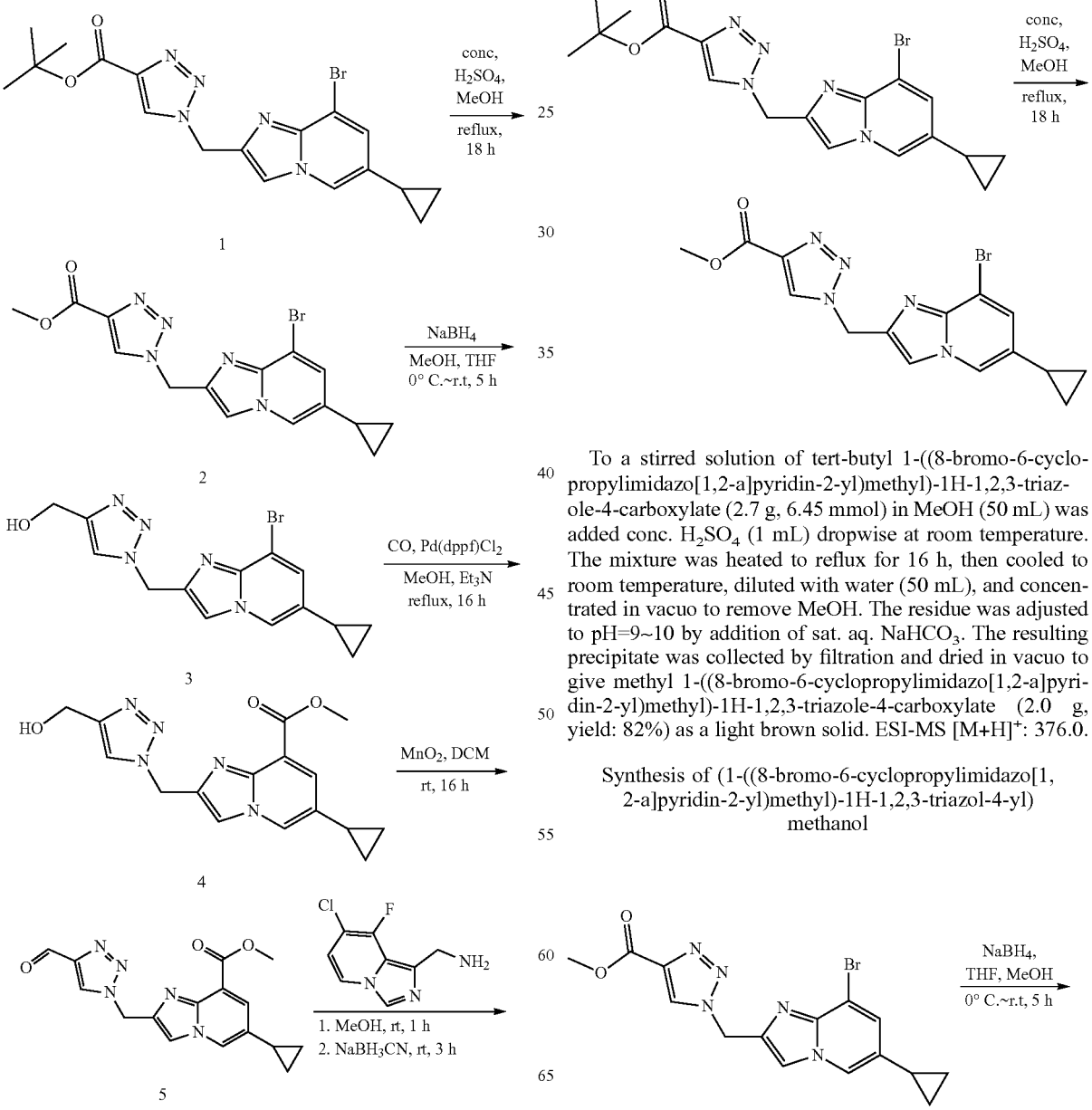

To a stirred solution of tert-butyl 1-((8-bromo-6-cyclopropylimidazo[1,2-a]pyridin-2-yl)methyl)-1H-1,2,3-triazole-4-carboxylate (2.7 g, 6.45 mmol) in MeOH (50 mL) was added conc. H₂SO₄ (1 mL) dropwise at room temperature. The mixture was heated to reflux for 16 h, then cooled to room temperature, diluted with water (50 mL), and concentrated in vacuo to remove MeOH. The residue was adjusted to pH=9~10 by addition of sat. aq. NaHCO₃. The resulting precipitate was collected by filtration and dried in vacuo to give methyl 1-((8-bromo-6-cyclopropylimidazo[1,2-a]pyridin-2-yl)methyl)-1H-1,2,3-triazole-4-carboxylate (2.0 g, yield: 82%) as a light brown solid. ESI-MS [M+H]⁺: 376.0.

Synthesis of (1-((8-bromo-6-cyclopropylimidazo[1,2-a]pyridin-2-yl)methyl)-1H-1,2,3-triazol-4-yl)methanol -continued

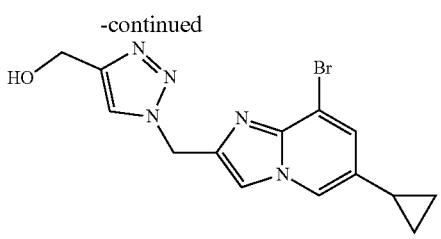

To a stirred solution of methyl 1-((8-bromo-6-cyclopropylimidazo[1,2-a]pyridin-2-yl)methyl)-1H-1,2,3-triazole-4-carboxylate (600 mg, 1.59 mmol) in MeOH (10 mL) and THF (10 mL) was added $NaBH_4$ (693 mg, 18.32 mmol) in portions at 0° C. The mixture was stirred at room temperature for 8 h, then quenched with sat. aq. $NH_4Cl$ (30 mL) and concentrated in vacuo to remove MeOH and THF. The residue was extracted with DCM (40 mL×3). The combined organics were washed with brine (80 mL), dried over $Na_2SO_4$ and concentrated to afford (1-((8-bromo-6-cyclopropylimidazo[1,2-a]pyridin-2-yl)methyl)-1H-1,2,3-triazol-4-yl)methanol (500 mg, yield: 91%) as a light brown solid which was used directly in next step without further purification. ESI-MS [M+H]$^+$: 348.0.

Synthesis of methyl 6-cyclopropyl-2-((4-(hydroxymethyl)-1H-1,2,3-triazol-1-yl)methyl)imidazo[1,2-a]pyridine-8-carboxylate

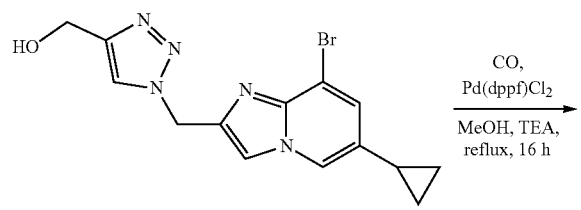

A mixture of (1-((8-bromo-6-cyclopropylimidazo[1,2-a]pyridin-2-yl)methyl)-1H-1,2,3-triazol-4-yl)methanol (500 mg, 1.44 mmol), $Pd(dppf)Cl_2$ (105 mg, 0.143 mmol) and triethylamine (729 mg, 7.218 mmol) in MeOH (20 mL) was refluxed for 16 h, then cooled to room temperature and filtered. The filtrate was concentrated and purified by silica gel chromatography (DCM/MeOH=20/1) to afford methyl 6-cyclopropyl-2-((4-(hydroxymethyl)-1H-1,2,3-triazol-1-yl)methyl)imidazo[1,2-a]pyridine-8-carboxylate (400 mg, yield: 85%) as a yellow solid. ESI-MS [M+H]$^+$: 328.1.

Synthesis of methyl 6-cyclopropyl-2-((4-formyl-1H-1,2,3-triazol-1-yl)methyl)imidazo[1,2-a]pyridine-8-carboxylate

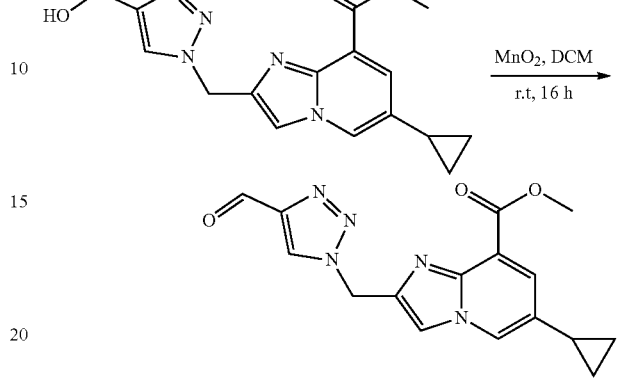

A mixture of methyl 6-cyclopropyl-2-((4-(hydroxymethyl)-1H-1,2,3-triazol-1-yl)methyl)imidazo[1,2-a]pyridine-8-carboxylate (400 mg, 1.22 mmol) and $MnO_2$ (2.12 g, 24.4 mmol) in DCM (15 mL) was stirred at room temperature for 16 h. The reaction mixture was filtered and the filtrate concentrated in vacuo. The residue was purified by silica gel chromatography (DCM/MeOH=20/1) to afford methyl 6-cyclopropyl-2-((4-formyl-1H-1,2,3-triazol-1-yl)methyl)imidazo[1,2-a]pyridine-8-carboxylate (180 mg, yield: 45%) as a yellow solid. ESI-MS [M+H]$^+$: 326.1.

Synthesis of methyl 2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate

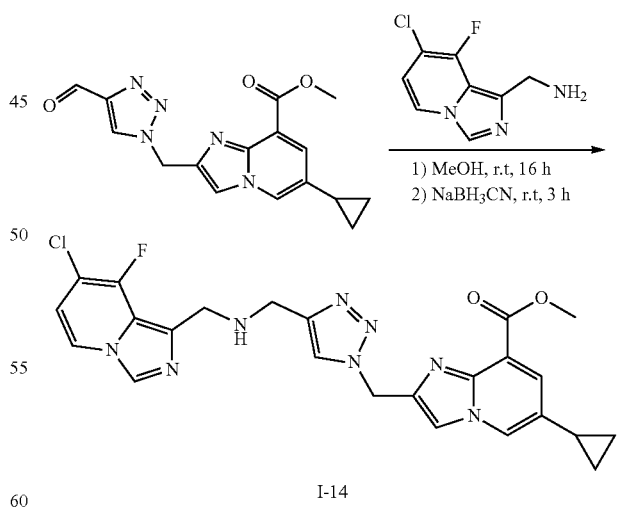

A mixture of methyl 6-cyclopropyl-2-((4-formyl-1H-1,2,3-triazol-1-yl)methyl)imidazo[1,2-a]pyridine-8-carboxylate (180 mg, 0.553 mmol) and (7-chloro-8-fluoroimidazo[1,5-a]pyridin-1-yl)methanamine (144 mg, 0.721 mmol) in MeOH (10 mL) was stirred at room temperature for 1 h. $NaBH_3CN$ (174 mg, 2.77 mmol) was added and the reaction mixture was stirred at room temperature for another 3 h. The reaction mixture was concentrated in vacuo, then diluted with water (40 mL) and extracted with DCM/MeOH (50 mL×3, v/v 10/1). The combined organics were washed with brine (50 mL), dried over $Na_2SO_4$ and concentrated. The residue was purified by silica gel chromatography (DCM/MeOH=20/1) to give methyl 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (130 mg, yield: 46%) as a pale solid. ESI-MS [M+H]+: 509.2.

$^1$H NMR (400 MHz, DMSO) δ 8.58 (s, 1H), 8.47 (s, 1H), 8.20 (d, J=7.4 Hz, 1H), 8.00 (s, 1H), 7.86 (s, 1H), 7.61 (d, J=1.6 Hz, 1H), 6.76 (t, J=6.9 Hz, 1H), 5.70 (s, 2H), 4.07 (s, 2H), 3.92 (s, 2H), 3.84 (s, 3H), 2.03-1.94 (m, 1H), 0.96-0.90 (m, 2H), 0.71-0.65 (m, 2H).

Example 15

2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylic Acid (I-15)

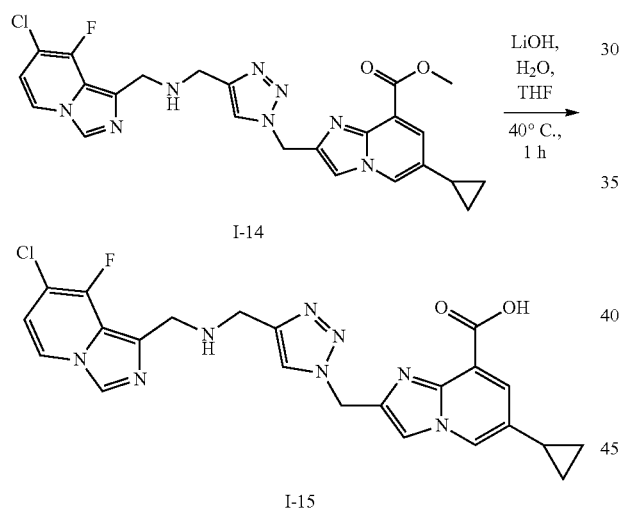

To a solution of methyl 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (110 mg, 0.216 mmol) in THF (4 mL) and water (2 mL) was added lithium hydroxide monohydrate (18 mg, 0.429 mmol). The mixture was stirred at 40° C. for 1 h. The reaction mixture was diluted with water (20 mL), acidified to pH=5-6 by addition of HCl (2 M), and concentrated in vacuo. The residue was purified by prep-HPLC to give 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylic acid (50 mg, yield: 47%) as a white solid. ESI-MS [M+H]+: 495.1.

$^1$H NMR (400 MHz, DMSO) δ 8.59 (s, 1H), 8.48 (s, 1H), 8.21 (d, J=7.4 Hz, 1H), 8.16 (s, 1H), 8.08 (s, 1H), 7.92 (s, 1H), 7.66 (s, 1H), 6.76 (t, J=6.8 Hz, 1H), 5.75 (s, 2H), 4.04 (s, 2H), 3.89 (s, 2H), 2.06-1.98 (m, 1H), 1.00-0.93 (m, 2H), 0.74-0.68 (d, 2H).

Example 16

N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (I-16)

Scheme 16

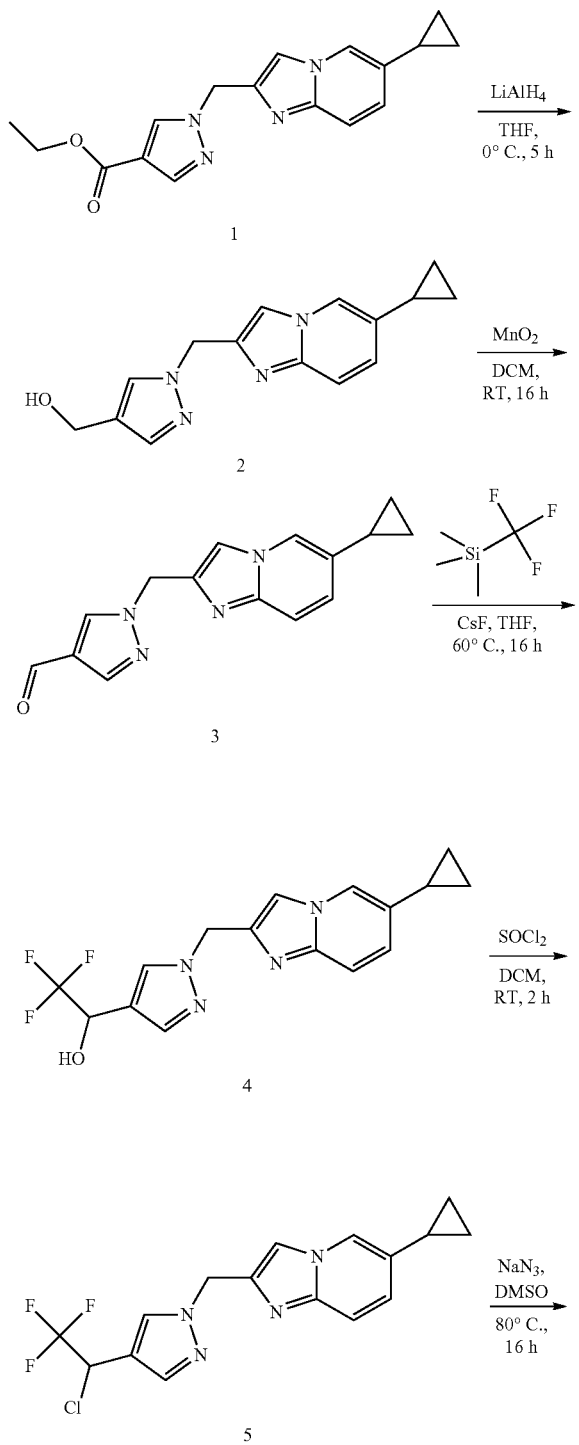

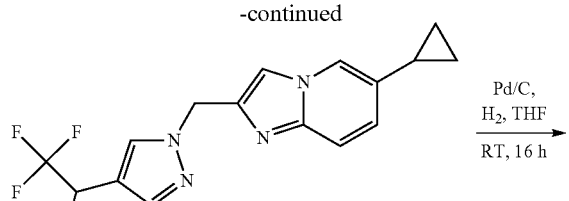

centrated in vacuo to give (1-((6-cyclopropylimidazo[1,2-a]pyridin-2-yl)methyl)-1H-pyrazol-4-yl)methanol as a yellow solid (588 mg, crude) which was used directly in next step without further purification. ESI-MS [M+H]⁺: 269.2.

Synthesis of 1-((6-cyclopropylimidazo[1,2-a]pyridin-2-yl)methyl)-1H-pyrazole-4-carbaldehyde

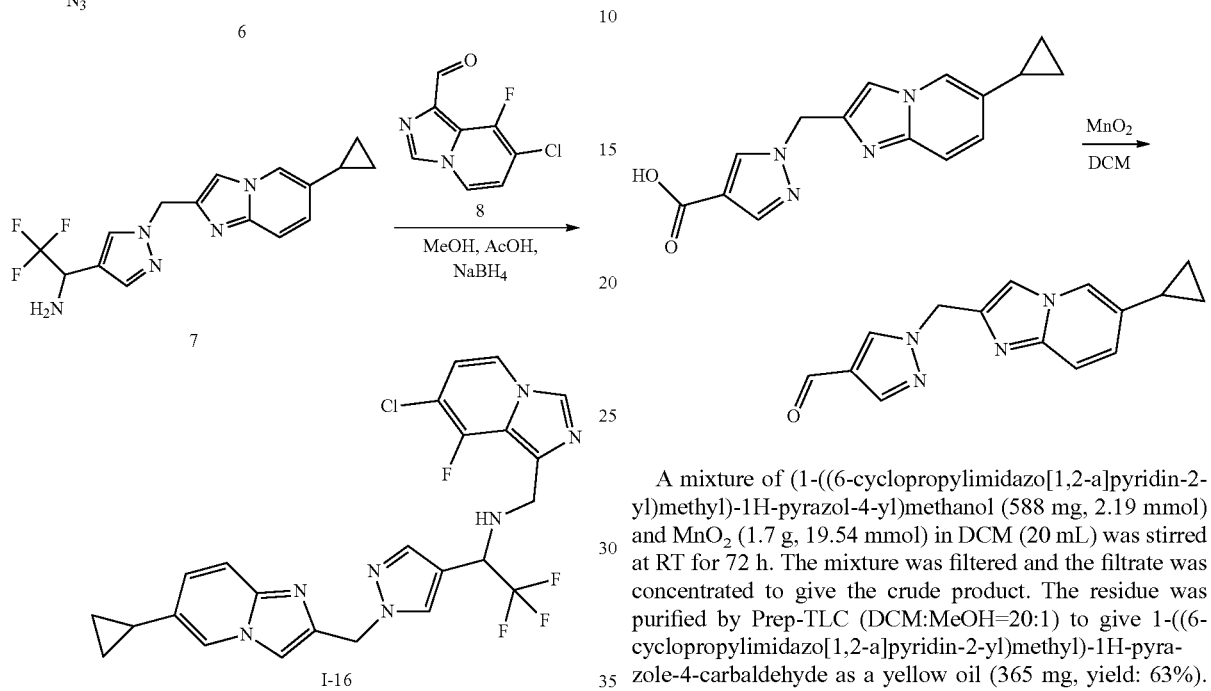

A mixture of (1-((6-cyclopropylimidazo[1,2-a]pyridin-2-yl)methyl)-1H-pyrazol-4-yl)methanol (588 mg, 2.19 mmol) and MnO₂ (1.7 g, 19.54 mmol) in DCM (20 mL) was stirred at RT for 72 h. The mixture was filtered and the filtrate was concentrated to give the crude product. The residue was purified by Prep-TLC (DCM:MeOH=20:1) to give 1-((6-cyclopropylimidazo[1,2-a]pyridin-2-yl)methyl)-1H-pyrazole-4-carbaldehyde as a yellow oil (365 mg, yield: 63%). ESI-MS [M+H]⁺: 267.1.

Synthesis of 1-((6-cyclopropylimidazo[1,2-a]pyridin-2-yl)methyl)-1H-pyrazole-4-carbaldehyde

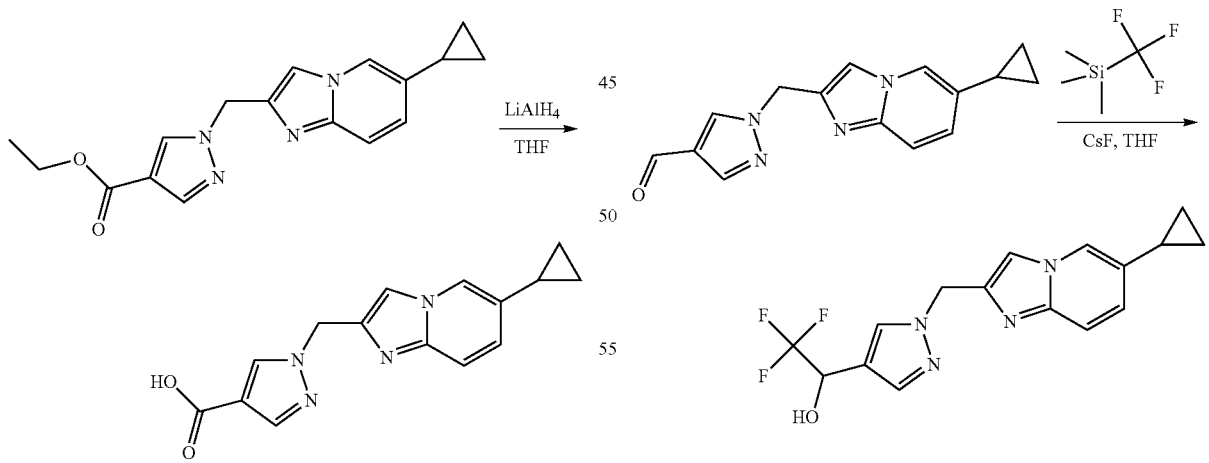

To a solution of ethyl 1-((6-cyclopropylimidazo[1,2-a]pyridin-2-yl)methyl)-1H-pyrazole-4-carboxylate (600 mg, 1.94 mmol) in THF (20 mL) was added LiAH₄ (221 mg, 5.81 mmol) slowly at 0° C. under N₂. The mixture was stirred at 0° C. for 5 h. The mixture was quenched with Na₂SO₄·10H₂O and diluted with EtOAc (50 mL). The resulting suspension was filtered and the filtrate was con- To a solution of 1-((6-cyclopropylimidazo[1,2-a]pyridin-2-yl)methyl)-1H-pyrazole-4-carbaldehyde (365 mg, 1.37 mmol) and CsF (584 mg, 3.845 mmol) in THF (10 mL) was added trimethyl(trifluoromethyl)silane (312 mg, 2.19 mmol) at room temperature. The mixture was stirred at 60° C. for 16 h under nitrogen. Then the mixture was diluted with EtOAc (50 mL) and washed with water (30 mL×3). The organic layer was dried over Na₂SO₄ and concentrated to give 1-(1-((6-cyclopropylimidazo[1,2-a]pyridin-2-yl)methyl)-1H-pyrazol-4-yl)-2,2,2-trifluoroethan-1-ol as a yellow solid (430 mg, yield: 93.5%) which was used directly in next step without further purification. ESI-MS [M+H]⁺: 337.2.

Synthesis of 2-((4-(1-chloro-2,2,2-trifluoroethyl)-1H-pyrazol-1-yl)methyl)-6-cyclopropylimidazo[1,2-a]pyridine

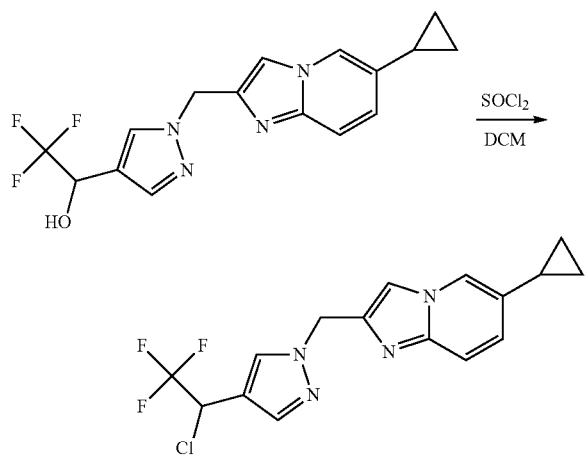

To a mixture of 1-(1-((6-cyclopropylimidazo[1,2-a]pyridin-2-yl)methyl)-1H-pyrazol-4-yl)-2,2,2-trifluoroethan-1-ol (430 mg, 1.27 mmol) in DCM (5 mL) was added SOCl₂ (1.0 mL) at 0° C. The reaction mixture was stirred at rt for 2 h. The mixture was concentrated to give 2-((4-(1-chloro-2,2,2-trifluoroethyl)-1H-pyrazol-1-yl)methyl)-6-cyclopropylimidazo[1,2-a]pyridine (450 mg, crude) as a yellow solid which was used directly in the next step without further purification. ESI-MS [M+H]⁺: 355.1.

Synthesis of 2-((4-(1-azido-2,2,2-trifluoroethyl)-1H-pyrazol-1-yl)methyl)-6-cyclopropylimidazo[1,2-a]pyridine

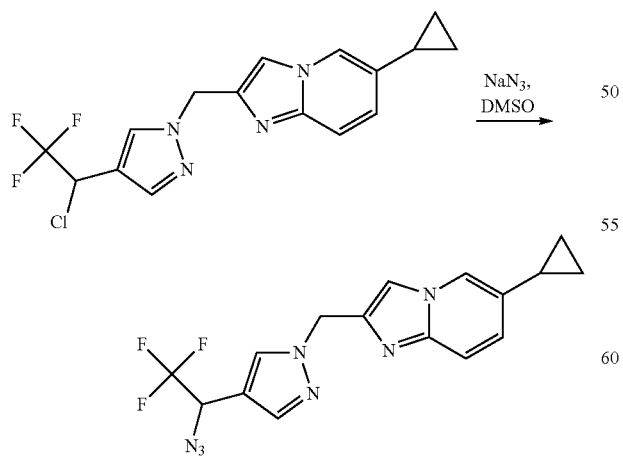

A mixture of 2-((4-(1-chloro-2,2,2-trifluoroethyl)-1H-pyrazol-1-yl)methyl)-6-cyclopropylimidazo[1,2-a]pyridine (450 mg, 1.27 mmol) and NaN₃ (165 mg, 2.54 mmol) in DMSO (5 mL) was stirred at 80° C. under N₂ for 16 h. The reaction mixture was then diluted with EtOAc (50 mL) and washed with water (30 mL×3). The organic layer was washed with brine (30 mL), dried over Na₂SO₄ and concentrated to give 2-((4-(1-azido-2,2,2-trifluoroethyl)-1H-pyrazol-1-yl)methyl)-6-cyclopropylimidazo[1,2-a]pyridine as a yellow solid (450 mg, crude) which was used directly in the next step without further purification. ESI-MS [M+H]⁺: 362.2.

Synthesis of 1-(1-((6-cyclopropylimidazo[1,2-a]pyridin-2-yl)methyl)-1H-pyrazol-4-yl)-2,2,2-trifluoroethan-1-amine

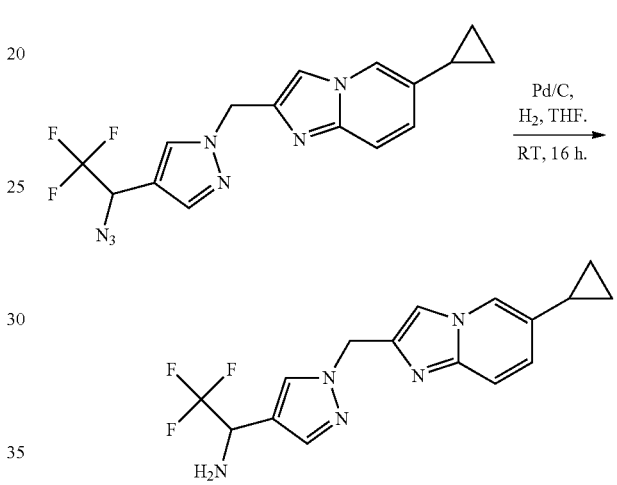

A mixture of 2-((4-(1-azido-2,2,2-trifluoroethyl)-1H-pyrazol-1-yl)methyl)-6-cyclopropylimidazo[1,2-a]pyridine (450 mg, 1.25 mmol) and Pd/C (50 mg) in dry THF (10.0 mL) was stirred at room temperature under H₂ for 16 h. Upon completion, the reaction mixture was filtered and the filtrate concentrated in vacuo to give (1-(1-((6-cyclopropylimidazo[1,2-a]pyridin-2-yl)methyl)-1H-pyrazol-4-yl)-2,2,2-trifluoroethan-1-amine (400 mg, crude) as a light yellow oil which was used directly in the next step without further purification. ESI-MS [M+H]⁺: 336.1.

Synthesis of N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine

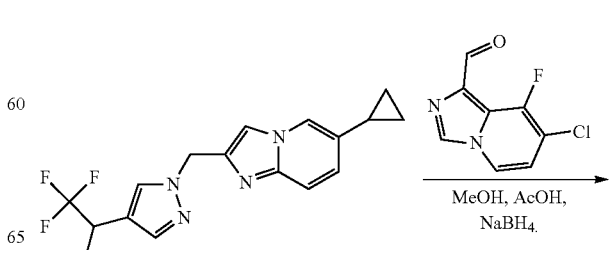

-continued

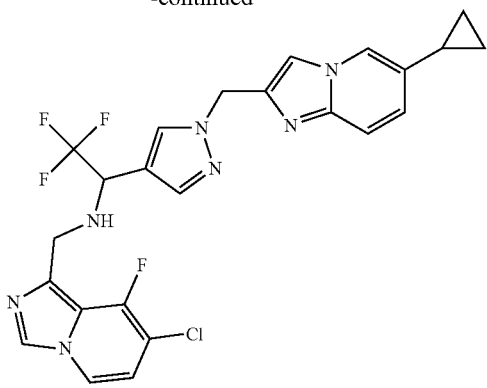

A mixture of 1-(1-((6-cyclopropylimidazo[1,2-a]pyridin-2-yl)methyl)-1H-pyrazol-4-yl)-2,2,2-trifluoroethan-1-amine (50 mg, 0.15 mmol) and 7-chloro-8-fluoroimidazo [1,5-a] pyridine-1-carbaldehyde (29.5 mg, 0.15 mmol) in MeOH/AcOH (5.0 mL/0.1 mL) was stirred at room temperature for 4 h. Then the reaction mixture was cooled to 0° C. and NaBH$_4$ (8.6 mg, 0.227 mmol) was added. The reaction mixture was stirred at RT for another 1 h, then concentrated in vacuo and purified by Prep-HPLC to give N-((7-chloro-8-fluoroimidazo [1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (19.8 mg, yield: 25.49%) as a light yellow solid. ESI-MS [M+H]$^+$: 518.1.

1H NMR (400 MHz, DMSO) δ 8.44 (d, J=2.4 Hz, 1H), 8.34 (s, 1H), 8.18 (s, 1H), 7.81 (s, 1H), 7.69 (s, 1H), 7.48 (s, 1H), 7.41 (d, J=9.3 Hz, 1H), 7.00 (dd, J=9.4, 1.8 Hz, 1H), 6.78-6.68 (m, 1H), 5.37 (s, 2H), 4.48-4.40 (m, 1H), 3.97-3.87 (m, 2H), 2.73-2.64 (m, 1H), 1.98-1.86 (m, 1H), 0.99-0.86 (m, 2H), 0.75-0.60 (m, 2H).

Example 17

Ethyl 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (I-17a)

3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl) propanoic acid (I-17b)

Scheme 17

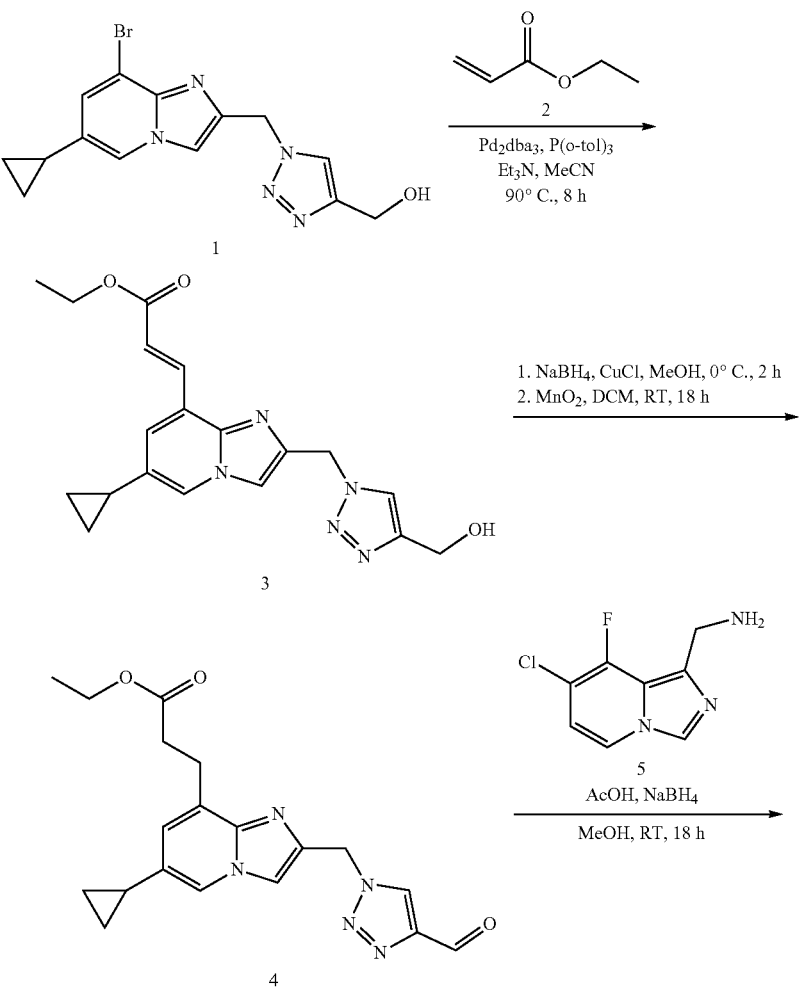

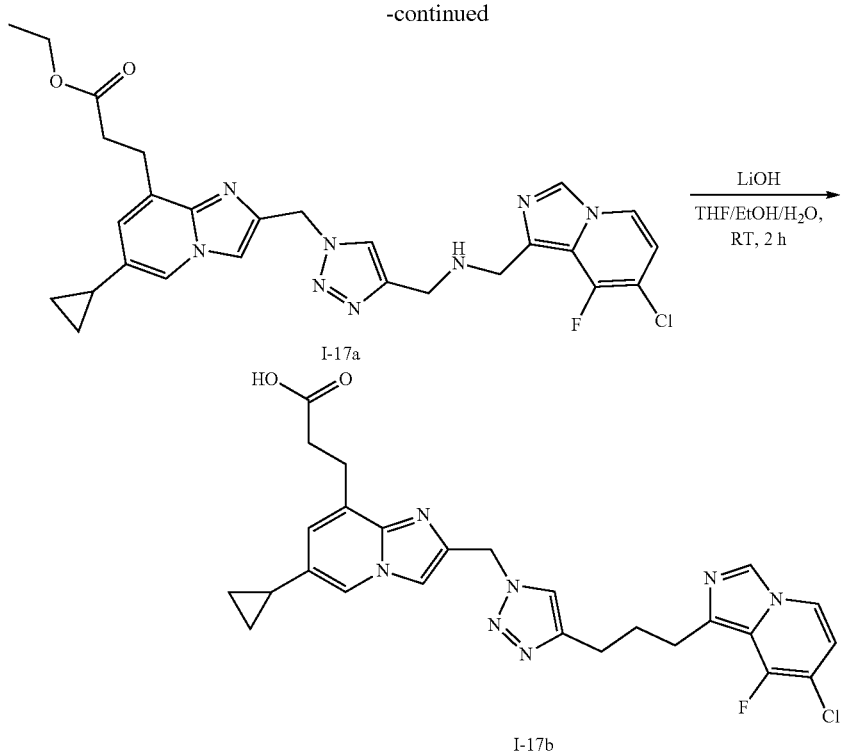

I-17a

I-17b

Synthesis of ethyl (E)-3-(6-cyclopropyl-2-((4-(hydroxymethyl)-1H-1,2,3-triazol-1-yl)methyl)imidazo[1,2-a]pyridin-8-yl)acrylate A mixture of (1-((8-bromo-6-cyclopropylimidazo[1,2-a]pyridin-2-yl)methyl)-1H-1,2,3-triazol-4-yl)methanol (1.4 g, 4.0 mmol), ethyl acrylate (0.81 g, 8.1 mmol), $Pd_2(dba)_3$ (183 mg, 0.2 mmol), (o-$MeC_6H_4$)$_3$P (365 mg, 1.2 mmol) and triethylamine (1.2 g, 12.0 mmol) in MeCN (20 mL) was stirred at 90° C. for 8 h. The reaction mixture was cooled to room temperature, diluted with water (100 mL), and extracted with EtOAc (50 mL×4). The combined organic layers were washed with brine (50 mL), dried over $Na_2SO_4$ and concentrated in vacuo. The crude product was purified by flash column chromatography (PE/EtOAc from 0 to 30%) to give ethyl (E)-3-(6-cyclopropyl-2-((4-(hydroxymethyl)-1H-1,2,3-triazol-1-yl)methyl)imidazo[1,2-a]pyridin-8-yl)acrylate (0.4 g, yield: 27%) as a brown solid.

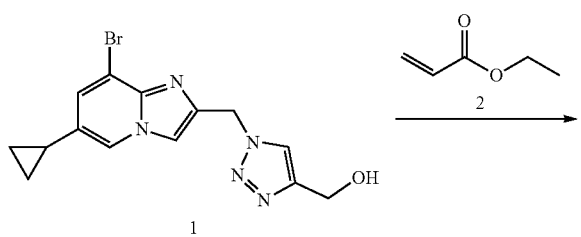

Synthesis of ethyl 3-(6-cyclopropyl-2-((4-formyl-1H-1,2,3-triazol-1-yl)methyl)imidazo[1,2-a]pyridin-8-yl)propanoate

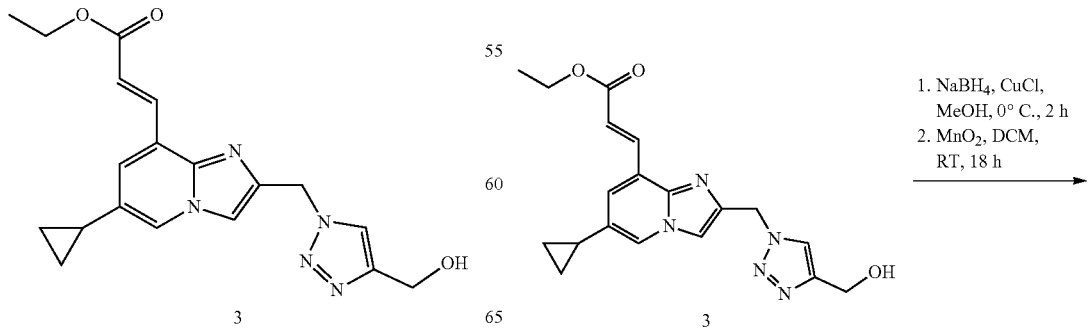

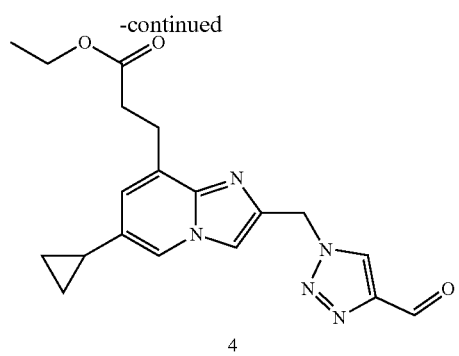

4

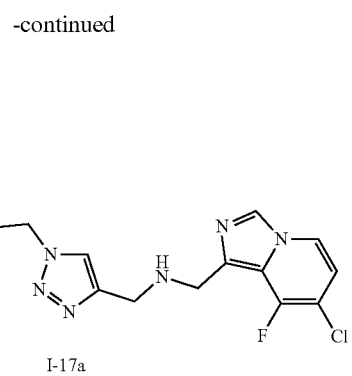

I-17a

To a solution of ethyl (E)-3-(6-cyclopropyl-2-((4-(hydroxymethyl)-1H-1,2,3-triazol-1-yl)methyl)imidazo[1,2-a]pyridin-8-yl)acrylate (400 mg, 1.09 mmol) in MeOH (10 mL) was added CuCl (162 mg, 1.63 mmol) and NaBH$_4$ (245 mg, 6.48 mmol) at 0° C. The mixture was stirred at 0° C. for 1 h, then quenched with water (50 mL) and extracted with EtOAc (40 mL×3). The combined organic layers were washed with brine (50 mL), dried over Na$_2$SO$_4$ and concentrated in vacuo. The crude product was dissolved in DCM (10 mL). MnO$_2$ (1.9 g, 21.8 mmol) was added and the mixture was stirred at room temperature for 18 h, then filtered and concentrated in vacuo. The residue was purified by flash column chromatography (PE/EtOAc from 0 to 20%) to give ethyl 3-(6-cyclopropyl-2-((4-formyl-1H-1,2,3-triazol-1-yl)methyl)imidazo[1,2-a]pyridin-8-yl)propanoate (160 mg, yield: 40%) as a colorless oil.

Synthesis of ethyl 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate

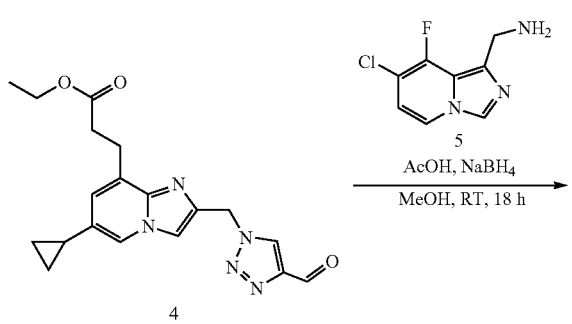

To a mixture of ethyl 3-(6-cyclopropyl-2-((4-formyl-H-1,2,3-triazol-1-yl)methyl)imidazo[1,2-a]pyridin-8-yl)propanoate (160 mg, 0.44 mmol) and (7-chloro-8-fluoroimidazo[1,5-a]pyridin-1-yl)methanamine hydrochloride (87 mg, 0.44 mmol) in EtOH (10 mL) was added a drop of AcOH. The reaction mixture was stirred at room temperature for 18 h. NaBH$_4$ (50 mg, 1.32 mmol) was added and the mixture was stirred at room temperature for another 2 h. The reaction was quenched with sat. aq. NH$_4$C$_1$ (50 mL) and extracted with EtOAc (30 mL×3). The combined organic layers were washed with brine (30 mL), dried over Na$_2$SO$_4$ and concentrated. The residue was purified by prep-HPLC to afford ethyl 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (120 mg, yield: 50%) as white solid. ESI-MS [M+H]$^+$: 551.2.

1H NMR (400 MHz, DMSO) δ 8.44 (d, J=2.4 Hz, 1H), 8.21 (d, J=1.3 Hz, 1H), 8.18 (d, J=7.4 Hz, 1H), 7.93 (s, 1H), 7.74 (s, 1H), 6.83 (s, 1H), 6.75-6.70 (m, 1H), 5.64 (s, 2H), 4.02 (q, J=7.1 Hz, 2H), 3.92 (s, 2H), 3.74 (s, 2H), 3.07 (t, J=7.6 Hz, 2H), 2.77 (t, J=7.7 Hz, 2H), 1.92-1.84 (m, 1H), 1.13 (t, J=7.1 Hz, 3H), 0.93-0.87 (m, 2H), 0.68-0.62 (m, 2H).

Synthesis of 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid

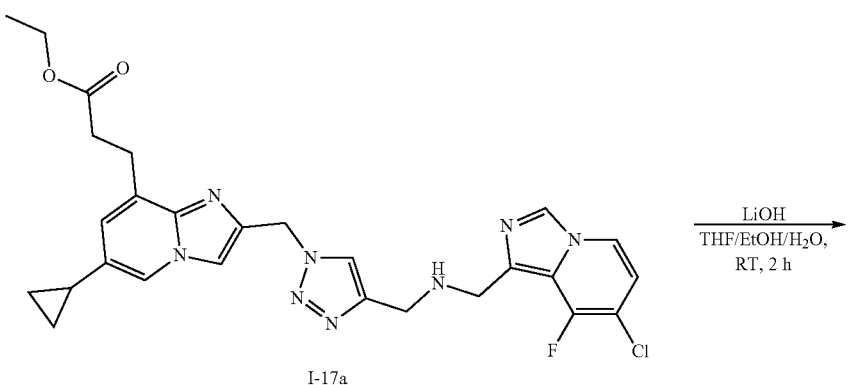

I-17a

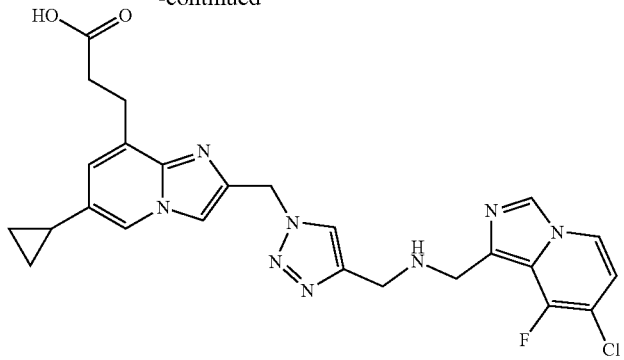

I-17b

A mixture of ethyl 3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (90 mg, 0.16 mmol) and LiOH—H$_2$O (21 mg, 0.50 mmol) in EtOH/THF/H$_2$O (3 mL/3 mL/2 mL) was stirred at room temperature for 2 h. The reaction mixture was adjusted to pH-5 by addition of HCl (2 M) and concentrated in vacuo. The residue was purified by prep-HPLC to afford 3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid (60 mg, yield: 71.5%) as a white solid. ESI-MS [M+H]$^+$: 523.2. Purity: 95.01 (214 nm), 95.35 (254 nm).

1H NMR (400 MHz, DMSO) δ 8.44 (d, J=2.3 Hz, 1H), 8.18 (d, J=7.4 Hz, 1H), 8.13 (s, 1H), 7.94 (s, 1H), 7.70 (s, 1H), 6.82 (s, 1H), 6.75-6.69 (m, 1H), 5.63 (s, 2H), 3.92 (s, 2H), 3.73 (s, 2H), 2.99 (t, J=7.7 Hz, 2H), 2.36 (t, J=7.7 Hz, 2H), 1.90-1.81 (m, 1H), 0.91-0.85 (m, 2H), 0.67-0.61 (m, 2H).

Example 18

1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (I-18)

Scheme 18

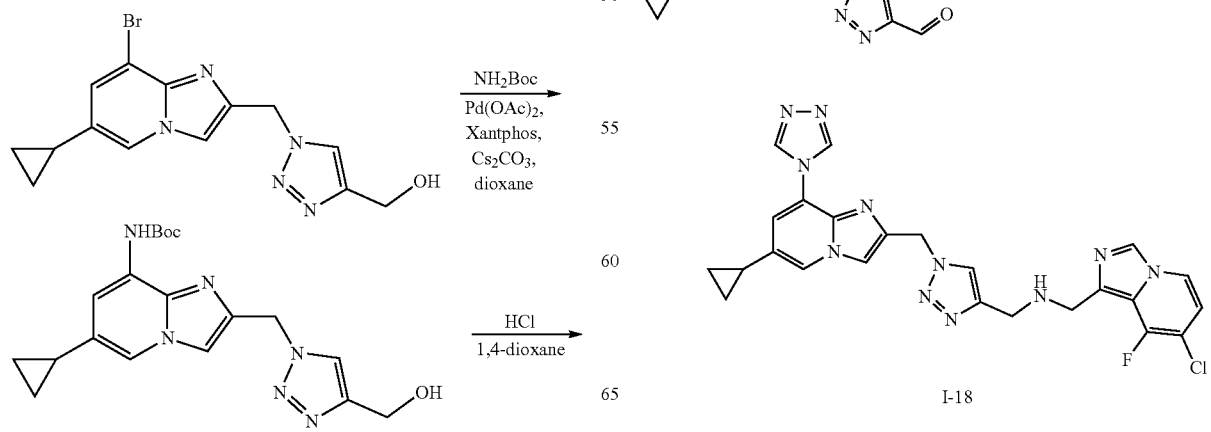

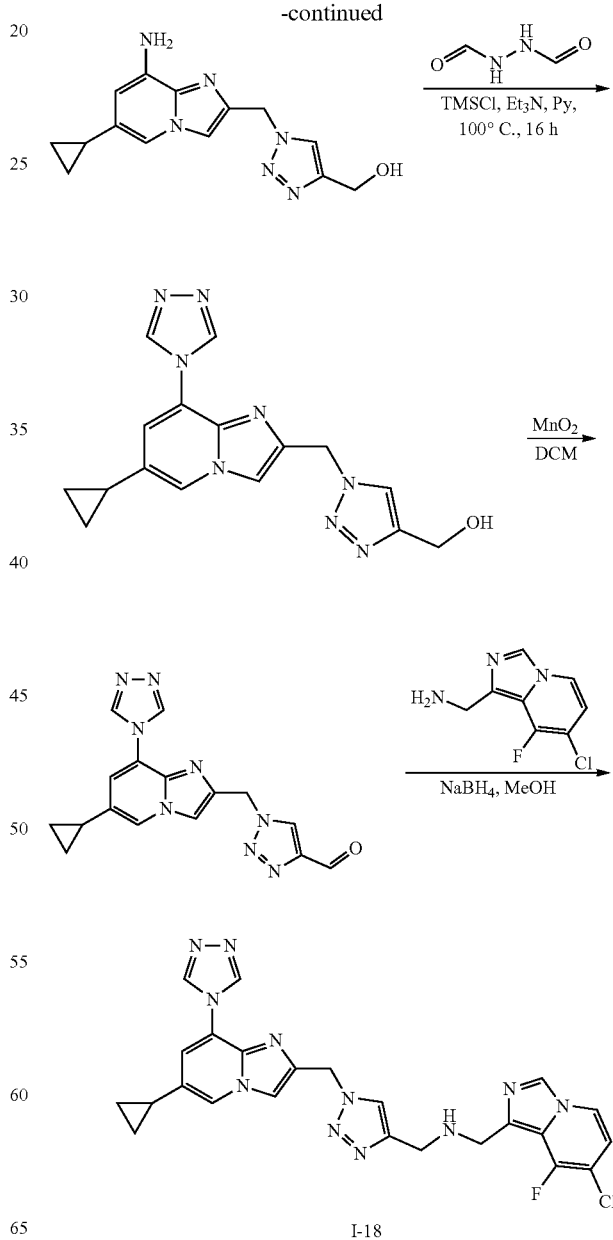

I-18

107

Synthesis of tert-butyl(6-cyclopropyl-2-((4-(hydroxymethyl)-1H-1,2,3-triazol-1-yl)methyl)imidazo[1,2-a]pyridin-8-yl)carbamate

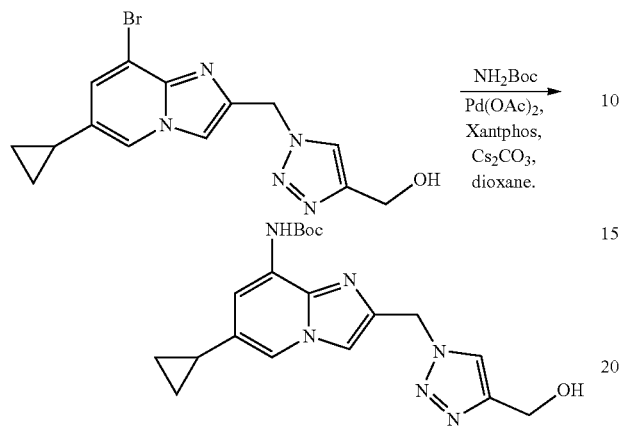

To a solution of (1-((8-bromo-6-cyclopropylimidazo[1,2-a]pyridin-2-yl)methyl)-1H-1,2,3-triazol-4-yl)methanol (450 mg, 1.3 mmol) in dioxane (10 mL) was added NH$_2$Boc (227.6 mg, 1.95 mmol), Pd(OAc)$_2$ (29.1 mg, 0.13 mmol), Xantphos(75.1 mg, 0.13 mmol) and Cs$_2$CO$_3$ (1.27 g, 3.9 mmol) at RT. The mixture was stirred at 95° C. for 16 h under N$_2$. The mixture was concentrated and purified by silica gel chromatography (DCM/MeOH=30/1) to give the product tert-butyl (6-cyclopropyl-2-((4-(hydroxymethyl)-1H-1,2,3-triazol-1-yl)methyl)imidazo[1,2-a]pyridin-8-yl)carbamate as a white solid (90 mg, yield: 18%). ESI-MS [M+H]$^+$: 385.2.

Synthesis of (1-((8-amino-6-cyclopropylimidazo[1,2-a]pyridin-2-yl)methyl)-1H-1,2,3-triazol-4-yl)methanol

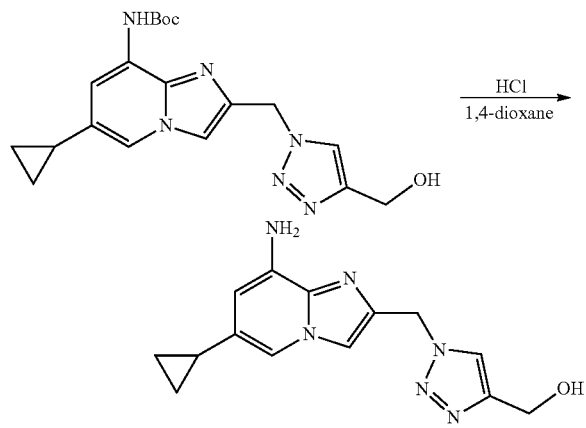

A solution of tert-butyl (6-cyclopropyl-2-((4-(hydroxymethyl)-1H-1,2,3-triazol-1-yl)methyl)imidazo[1,2-a]pyridin-8-yl)carbamate (90 mg, 0.23 mmol) in HCl (4M in dioxane) (5.0 mL) was stirred at RT for 1 h. The mixture was concentrated in vacuo to give (1-((8-amino-6-cyclopropylimidazo[1,2-a]pyridin-2-yl)methyl)-1H-1,2,3-triazol-4-yl) methanol (90 mg, crude) as a yellow solid which was used in the next step directly without further purification. ESI-MS [M+H]$^+$: 285.1.

108

Synthesis of (1-((6-cyclopropyl-8-(4H-1,2,4-triazol-4-y)imidazo[1,2-a]pyridin-2-yl)methyl)-1H-1,2,3-triazol-4-yl)methanol

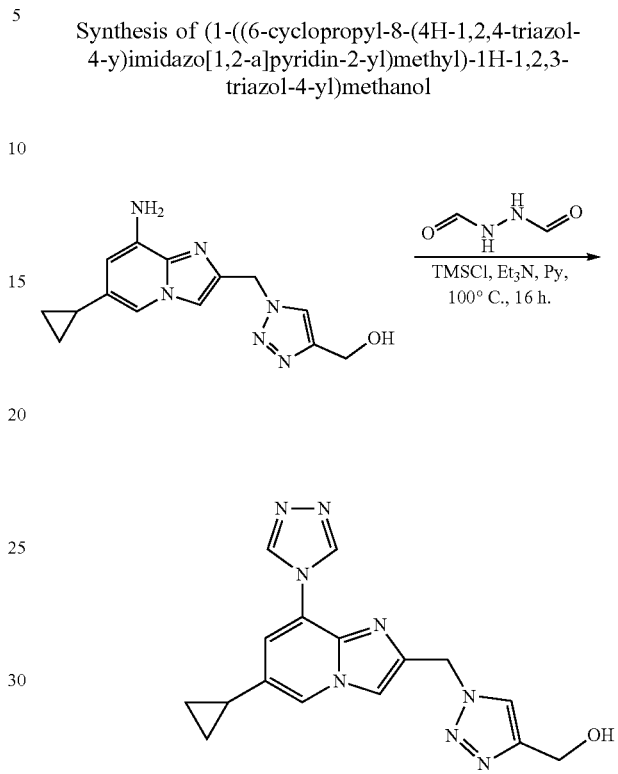

To a solution of (1-((8-amino-6-cyclopropylimidazo[1,2-a]pyridin-2-yl)methyl)-1H-1,2,3-triazol-4-yl)methanol (300 mg, 1.06 mmol) in pyridine (15 mL) was added N'-formylformohydrazide (280 mg, 3.18 mmol) and Et$_3$N (749 mg, 7.42 mmol) at RT. Then the TMSCl (1.72 g, 15.9 mmol) was added at 0° C. under N$_2$. The resulting solution was stirred at 100° C. for 18 h and then cooled to RT. The mixture was concentrated in vacuo and the residue was purified by silica gel chromatography (DCM/MeOH=20/1~10/1) to give (1-((6-cyclopropyl-8-(4H-1,2,4-triazol-4-yl)imidazo[1,2-a]pyridin-2-yl)methyl)-1H-1,2,3-triazol-4-yl)methanol (150 mg, 42%) as a white solid. ESI-MS [M+H]$^+$: 337.1.

Synthesis of 1-((6-cyclopropyl-8-(4H-1,2,4-triazol-4-yl)imidazo[1,2-a]pyridin-2-yl)methyl)-1H-1,2,3-triazole-4-carbaldehyde

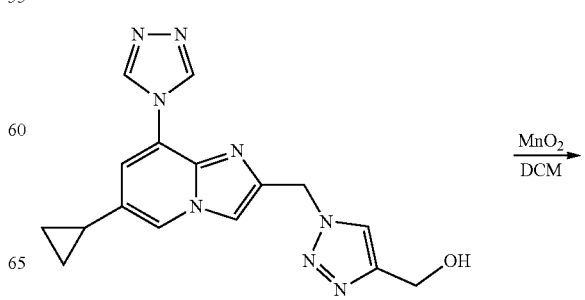

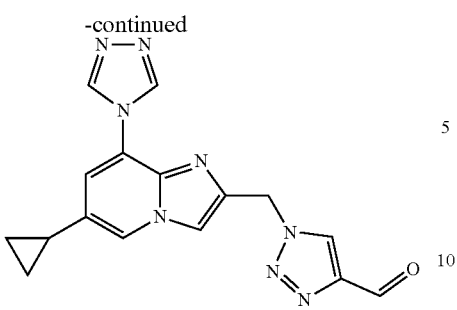

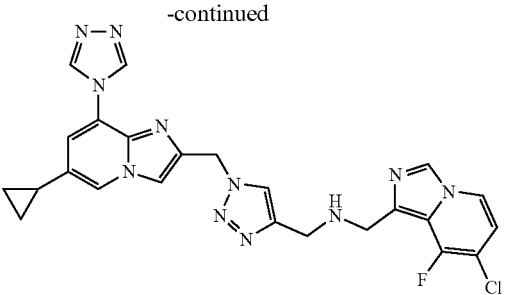

I-18

To a solution of (1-((6-cyclopropyl-8-(4H-1,2,4-triazol-4-yl)imidazo[1,2-a]pyridin-2-yl)methyl)-1H-1,2,3-triazol-4-yl)methanol (60 mg, 0.18 mmol) in DCM (5.0 mL) at RT was added MnO$_2$ (157 mg, 1.8 mmol). The reaction mixture was stirred at RT for 18 h. Additional MnO$_2$ (78 mg. 0.9 mmol) was added and the reaction mixture was stirred for another 3 h. Upon completion, the mixture was filtered and the filtrate was concentrated to give 1-((6-cyclopropyl-8-(4H-1,2,4-triazol-4-yl)imidazo[1,2-a]pyridin-2-yl)methyl)-1H-1,2,3-triazole-4-carbaldehyde (40 mg, crude) as a yellow solid which was used in the next step directly without further purification. ESI-MS [M+H]$^+$: 335.1.

Synthesis of 1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine

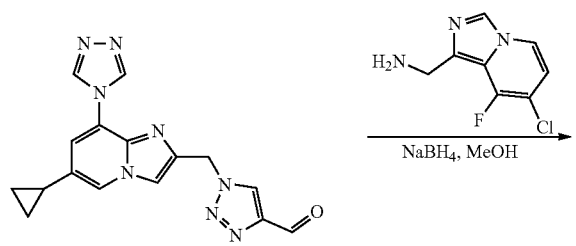

A mixture of 1-((6-cyclopropyl-8-(4H-1,2,4-triazol-4-yl)imidazo[1,2-a]pyridin-2-yl)methyl)-1H-1,2,3-triazole-4-carbaldehyde (40 mg, 0.12 mmol) and (7-chloro-8-fluoroimidazo[1,5-a]pyridin-1-yl)methanamine (30 mg, 0.15 mmol) in MeOH (5.0 mL) was added AcOH (0.1 mL) at RT. The reaction mixture was stirred at RT for 18 h. Then NaBH$_4$ (8.5 mg, 0.22 mmol) was added and the mixture was stirred for another 4 h at RT. The mixture was then concentrated and the residue purified by Prep-TLC (DCM/MeOH=15:1) to give 1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (5 mg, 8%) as a light yellow solid. ESI-MS [M+H]$^+$: 518.2.

1H NMR (400 MHz, DMSO) δ 9.41 (s, 2H), 8.48 (s, 1H), 8.44 (s, 1H), 8.26 (s, 1H), 8.18 (d, J=7.4 Hz, 1H), 8.03 (s, 1H), 7.98 (s, 1H), 7.45 (d, J=0.9 Hz, 1H), 6.73 (t, J=6.9 Hz, 1H), 5.71 (s, 2H), 3.94 (s, 2H), 3.77 (s, 2H), 2.01-1.96 (m, 1H), 1.80-1.72 (m, 1H), 1.02-0.95 (m, 2H), 0.86-0.77 (m, 2H).

Example 19

2-(7-chloroimidazo[1,5-a]pyridin-1-yl)-N-(1-(1-((6-cyclopropylimidazo[1,2-a]pyridin-2-yl)methyl)-1H-pyrazol-4-yl)-2,2,2-trifluoroethyl)acetamide (I-19)

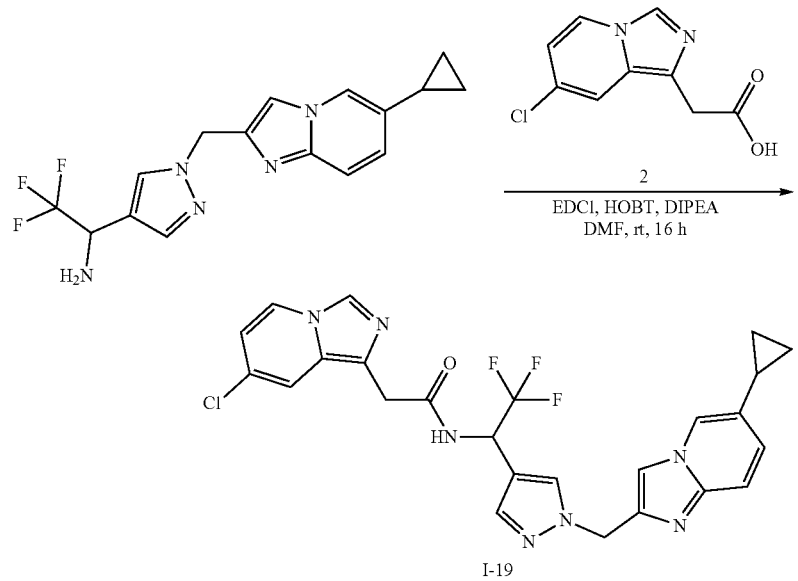

I-19

A mixture of 1-(1-(((6-cyclopropylimidazo[1,2-a]pyridin-2-yl)methyl)-1H-pyrazol-4-yl)-2,2,2-trifluoroethan-1-amine (50 mg, 0.15 mmol), 2-(7-chloroimidazo[1,5-a]pyridin-1-yl) acetic acid (31 mg, 0.15 mmol), EDCI (40.3 mg, 0.21 mmol), HOBt (28.4 mg, 0.21 mmol) and DIPEA (54.2 mg, 0.42 mmol) in DMF (3 mL) was stirred at RT for 16 h. The mixture was diluted with EtOAc (50 mL) and washed with brine (30 mL×3). The organic layer was concentrated and the residue was purified by Prep-HPLC to give 2-(7-chloro-imidazo[1,5-a]pyridin-1-yl)-N-(1-(1-((6-cyclopropylimidazo[1,2-a]pyridin-2-yl)methyl)-1H-pyrazol-4-yl)-2,2,2-tri-fluoroethyl)acetamide (23.9 mg, 30%) as a light yellow solid. ESI-MS [M+H]$^+$: 528.1.

1H NMR (400 MHz, DMSO) δ 9.11 (d, J=9.4 Hz, 1H), 8.35 (s, 1H), 8.32-8.25 (m, 2H), 7.92 (s, 1H), 7.74 (s, 1H), 7.73-7.72 (m, 1H), 7.58 (s, 1H), 7.41 (d, J=9.4 Hz, 1H), 7.00 (dd, J=9.4, 1.7 Hz, 1H), 6.63 (dd, J=7.5, 2.1 Hz, 1H), 5.80-5.64 (m, 1H), 5.39 (s, 2H), 3.78 (s, 2H), 2.01-1.87 (m, 1H), 1.00-0.85 (m, 2H), 0.79-0.53 (m, 2H).

Example 20

N-((7-chloro-8-fluoroimidazo[1,5-a]pyridin-1-yl) methyl)-1-((6-cyclopropyl-8-(4-methylpiperazin-1-yl)imidazo[1,2-a]pyridin-2-yl)methyl)-1H-1,2,3-triazole-4-carboxamide (I-20)

Scheme 20

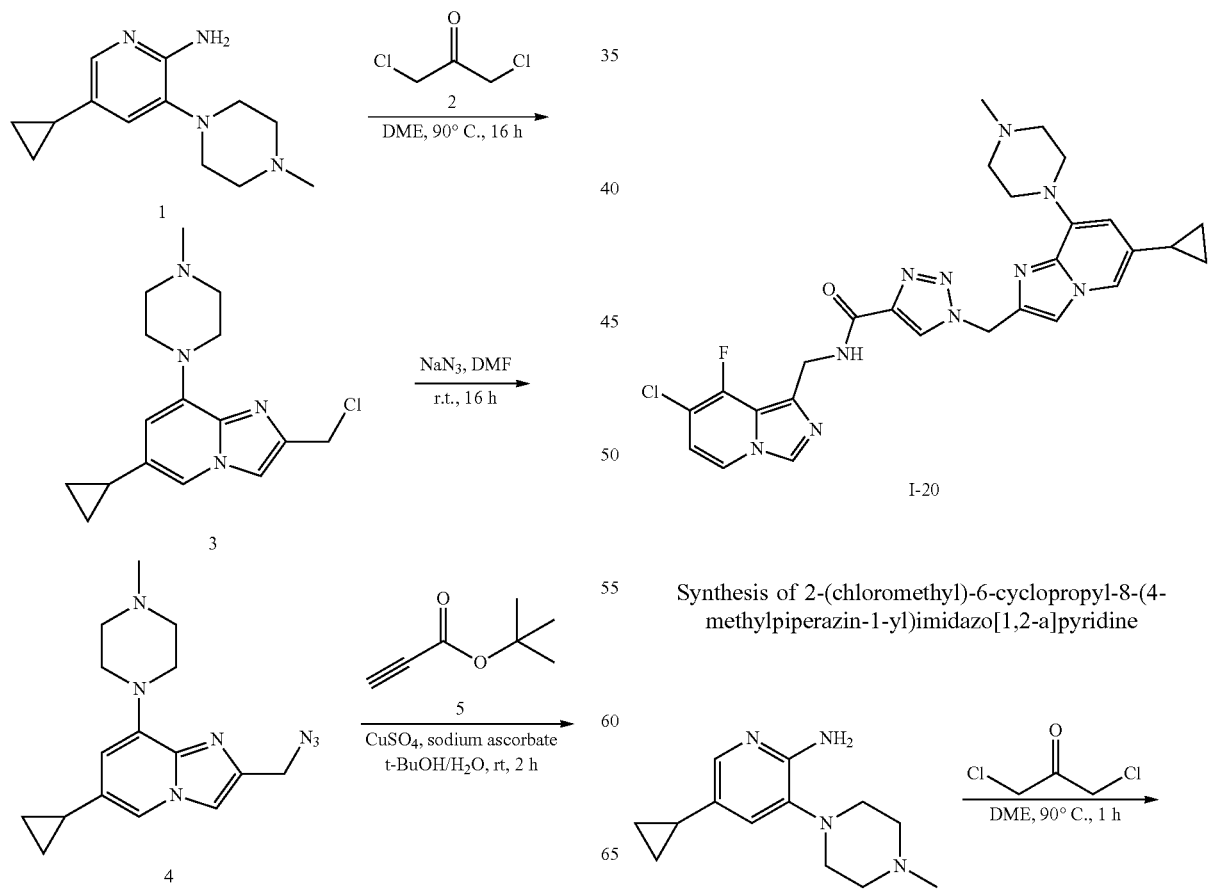

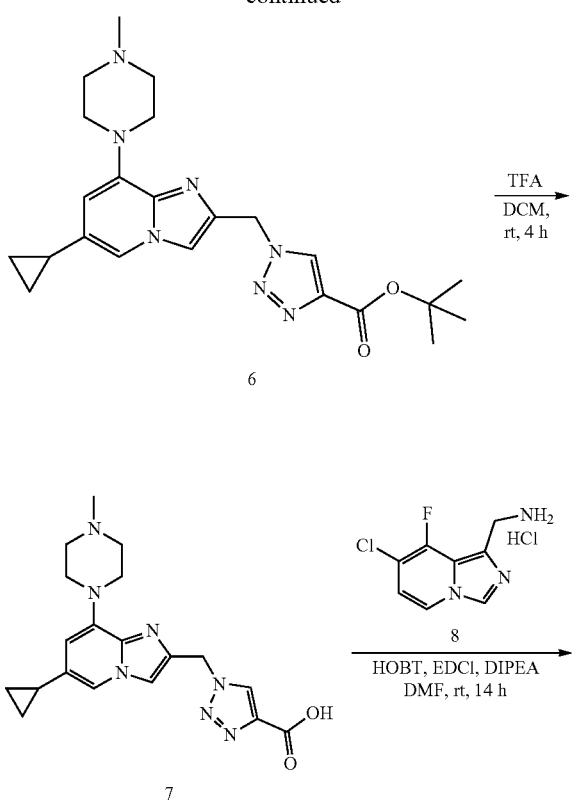

Synthesis of 2-(chloromethyl)-6-cyclopropyl-8-(4-methylpiperazin-1-yl)imidazo[1,2-a]pyridine -continued

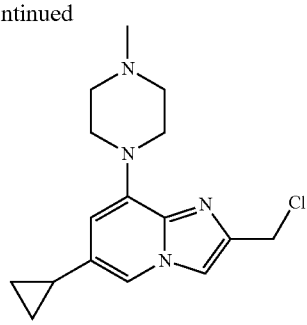

To a mixture of 5-cyclopropyl-3-(4-methylpiperazin-1-yl) pyridin-2-amine (460 mg, 1.98 mmol) in DME (25 mL) was added 1,3-dichloropropan-2-one (620 mg, 5 mmol). The reaction was stirred at 90° C. for 16 h. The reaction mixture was concentrated in vacuo to give 2-(chloromethyl)-6-cyclopropyl-8-(4-methylpiperazin-1-yl)imidazo[1,2-a]pyridine (400 mg, yield: 32%, crude) as a yellow solid which was used in next step directly without further purification. ESI-MS [M+H]$^+$: 305.1.

Synthesis of 2-(azidomethyl)-6-cyclopropyl-8-(4-methylpiperazin-1-yl)imidazo[1,2-a]pyridine

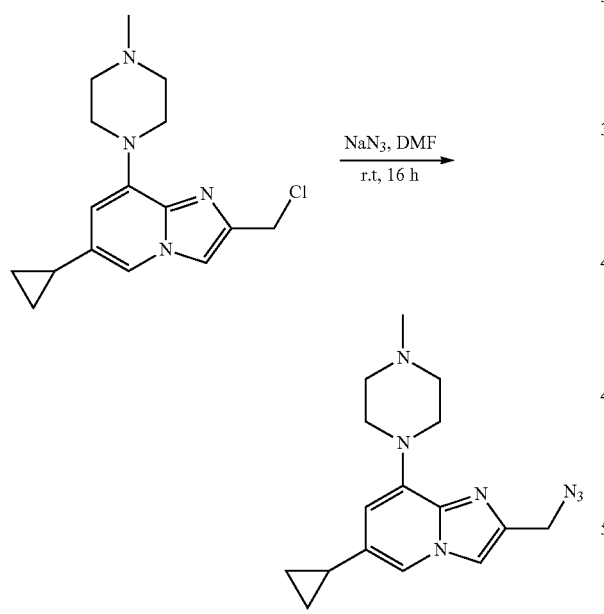

To a mixture of 2-(chloromethyl)-6-cyclopropyl-8-(4-methylpiperazin-1-yl)imidazo[1,2-a]pyridine (400 mg, 1.3 mmol) in DMF (5 mL) was added NaN$_3$ (250 mg, 3.9 mmol). The reaction mixture was stirred at room temperature for 16 h. Water (50 mL) was added and the mixture was extracted with EtOAc (30 ml×3). The combined organic layers were washed with brine (30 ml), dried over Na$_2$SO$_4$ and concentrated in vacuo. The residue was purified by flash column chromatography (MeOH/DCM from 0 to 10%) to give 2-(azidomethyl)-6-cyclopropyl-8-(4-methylpiperazin-1-yl)imidazo[1,2-a]pyridine (100 mg, yield: 25%) as a yellow solid. ESI-MS [M+H]$^+$: 312.1.

Synthesis of tert-butyl 1-((6-cyclopropyl-8-(4-methylpiperazin-1-yl)imidazo[1,2-a]pyridin-2-yl)methyl)-1H-1,2,3-triazole-4-carboxylate

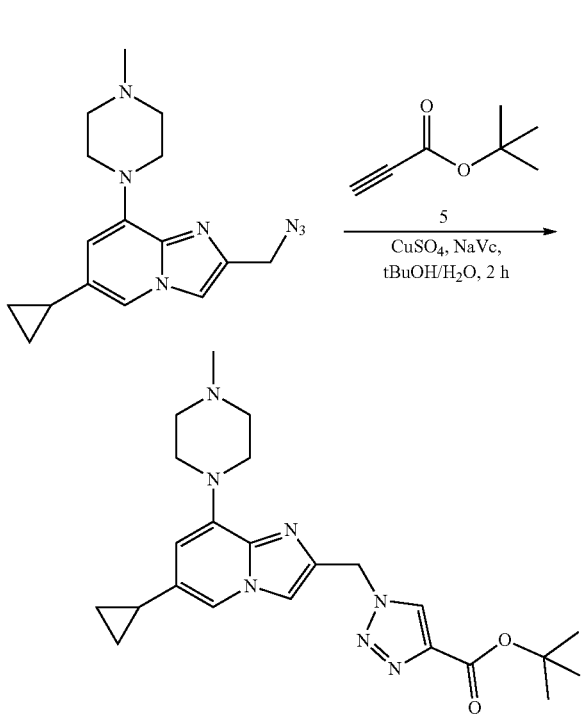

To a mixture of 2-(azidomethyl)-6-cyclopropyl-8-(4-methylpiperazin-1-yl)imidazo[1,2-a]pyridine (100 mg, 0.32 mmol) in t-BuOH (5 mL) and H$_2$O (5 mL) was added tert-butyl propiolate (52 mg, 0.42 mmol), CuSO4 (25 mg, 0.16 mmol) and sodium ascorbate (31 mg, 0.16 mmol). The reaction mixture was stirred at rt for 2 h. Water (30 mL) was added and the mixture was extracted with EtOAc (20 mL×3). The combined organic layers were washed with brine (20 mL), dried over Na2SO4, and concentrated in vacuo. The residue was purified by flash column chromatography (MeOH/DCM from 0 to 10%) to give tert-butyl 1-((6-cyclopropyl-8-(4-methylpiperazin-1-yl)imidazo[1,2-a]pyridin-2-yl)methyl)-1H-1,2,3-triazole-4-carboxylate (20 mg, yield: 14%) as a yellow solid. ESI-MS [M+H]$^+$: 438.2.

Synthesis of 1-((6-cyclopropyl-8-(4-methylpiperazin-1-yl)imidazo[1,2-a]pyridin-2-yl)methyl)-1H-1,2,3-triazole-4-carboxylic Acid

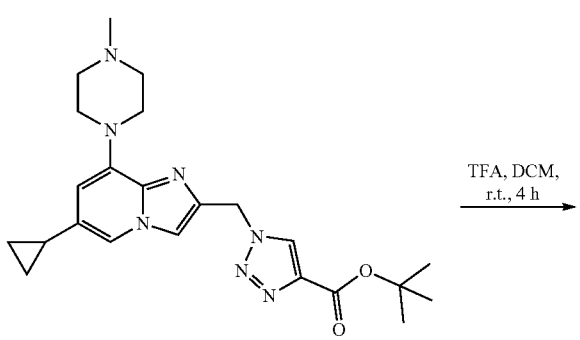

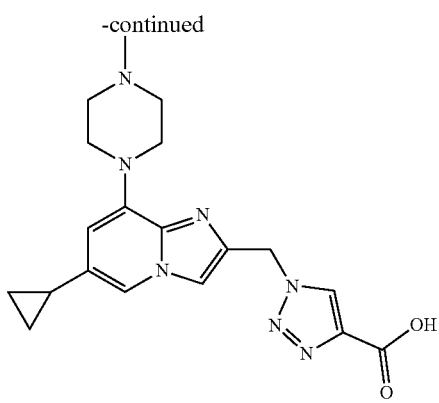

A mixture of tert-butyl 1-((6-cyclopropyl-8-(4-methylpiperazin-1-yl)imidazo[1,2-a]pyridin-2-yl)methyl)-1H-1,2,3-triazole-4-carboxylate (15 mg, 0.034 mmol) in dry DCM (3 mL) and TFA (0.6 mL) was stirred at room temperature for 4 h. The reaction mixture was concentrated in vacuo to give 1-((6-cyclopropyl-8-(4-methylpiperazin-1-yl)imidazo[1,2-a]pyridin-2-yl)methyl)-1H-1,2,3-triazole-4-carboxylic acid (3 mg, yield: 23% crude) as a yellow solid which was used in next step directly without further purification. ESI-MS [M+H]$^+$: 382.1.

Synthesis of N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide

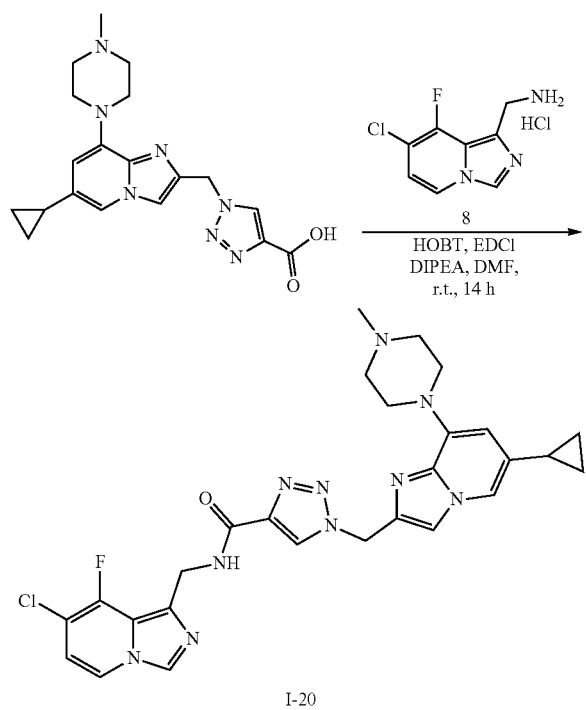

A mixture of 1-((6-cyclopropyl-8-(4-methylpiperazin-1-yl)imidazo[1,2-a]pyridin-2-yl)methyl)-1H-1,2,3-triazole-4-carboxylic acid (20 mg, 0.05 mmol), (7-chloro-8-fluoroimidazo[1,5-a]pyridin-1-yl)methanamine hydrochloride (20 mg, 0.1 mmol), HOBT (10 mg, 0.074 mmol), EDCl (14 mg, 0.075 mmol) and DIPEA (32 mg, 0.25 mmol) in dry DMF (5 ml) was stirred at room temperature for 16 h. Water (50 mL) was added and the mixture was extracted with EtOAc (20 mL×3). The organic layers were washed with brine (20 mL), dried over Na$_2$SO$_4$ and concentrated in vacuo. The residue was purified by Prep-TLC (MeOH/DCM=10%) to give N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide (1 mg, yield: 14%) as a yellow solid. ESI-MS [M+H]$^+$: 563.1.

1H NMR (400 MHz, DMSO) δ 8.66 (t, J=5.4 Hz, 1H), 8.47 (s, 1H), 8.40 (d, J=2.4 Hz, 1H), 8.16 (d, J=7.4 Hz, 1H), 7.86 (s, 1H), 7.67 (s, 1H), 6.75-6.68 (m, 1H), 6.16 (s, 1H), 5.67 (s, 2H), 4.65 (d, J=5.5 Hz, 2H), 3.46 (s, 4H), 2.56 (s, 4H), 2.27 (s, 3H), 1.84-1.80 (m, 1H), 0.84-0.79 (m, 2H), 0.64-0.50 (m, 2H).

Example 21

Inhibitory Activity of Exemplary Compounds against Plasma Kallikrein. Example compounds were evaluated for inhibition of the human activated kallikrein enzyme in two formats of an assay employing a fluorogenic peptide substrate. In one assay format, the concentrations of reagents were as follows: 20 mM Tris pH 7.5, 1 mM EDTA, 150 mM sodium chloride, 0.1% PEG-400, 0.1% Triton X-100, 500 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 10 min at RT and fluorescence emission at 460 nm from 380 nm excitation measured with a microplate reader. In another assay format, the concentrations of reagents were as follows: 20 mM Tris pH 7.5, 1 mM EDTA, 150 mM sodium chloride, 0.1% PEG-400, 0.1% Triton X-100, 5 pM activated kallikrein enzyme, 300 uM Pro-Phe-Arg-7-amido-4-methylcoumarin substrate. Prior to reaction initiation with substrate, enzyme and inhibitors were preincubated for 30 min at RT. After initiation with substrate, reactions were incubated for 18 h at RT and fluorescence emission at 460 nm from 380 nm excitation measured with a microplate reader.

Table 1 provides the results of the assay in the format with 500 pM activated kallikrein assay. For the compounds listed in Table 1, the EC$_{50}$ values are reported according to the following ranges: A≤50 nM; 50 nM<B≤200 nM; 200 nM<C≤1000 nM; 1000 nM<D.

TABLE 1

| Compound | Primary Dose Response Assay: Average EC50 |
|---|---|
| I-1 | A |
| I-2 | D |
| I-3 | B |
| I-4 | C |
| I-5 | C |
| I-6 | A |
| I-7 | A |
| I-8 | A |
| I-9 | C |
| I-10 | A |
| I-11 | A |
| I-12 | B |
| I-13 | A |
| I-14 | A |
| I-15 | C |
| I-16 | A |

TABLE 1-continued

| Compound | Primary Dose Response Assay: Average EC50 |
|---|---|
| I-17a | A |
| I-17b | A |
| I-18 | A |
| I-19 | B |
| 1-20 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A compound of Formula (I):

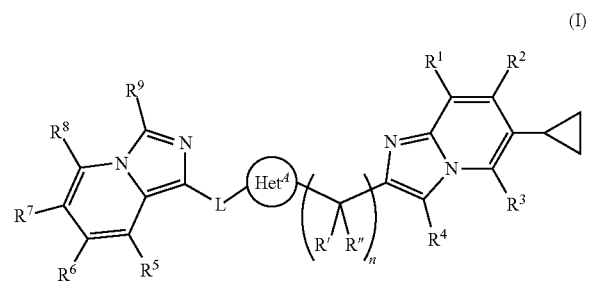

(I)

or a pharmaceutically acceptable salt thereof, wherein:

$Het^4$ is selected from a 3- to 7-membered saturated or partially unsaturated monocyclic heterocyclylene having 1-2 heteroatoms selected from oxygen, nitrogen, or sulfur, a 5- to 6-membered monocyclic heteroarylene having 1-4 heteroatoms selected from oxygen, nitrogen, or sulfur, a 7- to 10-membered saturated or partially unsaturated bicyclic heterocyclylene having 1-4 heteroatoms selected from oxygen, nitrogen, or sulfur, and a 7- to 10-membered bicyclic heteroarylene having 1-5 heteroatoms selected from oxygen, nitrogen, or sulfur, wherein $Het^4$ is substituted with 0-4 $R^4$ groups;

each $R^4$ is independently selected from halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6- membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

L is an optionally substituted $C_{1-6}$ hydrocarbon chain, wherein 1-3 methylene units are independently replaced with —Cy—, —C(R)$_2$—O—, —NR—, —C(O)—, —S(O)$_2$—, —C(O)NR—, —NRC(O)—, —S(O)$_2$NR—, and —NRS(O)$_2$—;

—Cy— is 3- to 7-membered saturated or partially unsaturated monocyclic carbocyclylene, 3- to 7-membered saturated or partially unsaturated monocyclic heterocyclylene having 1-2 heteroatoms selected from oxygen, nitrogen, or sulfur, or 5- to 6-membered heteroarylene having 1-4 heteroatoms selected from oxygen, nitrogen, or sulfur;

R' and R" are independently selected from hydrogen, halogen, —OR, —NR$_2$, —SR, and optionally substituted $C_{1-6}$ aliphatic; wherein R' may be taken together with a monocyclic $Het^4$ to form an optionally substituted fused 7- to 10-membered saturated or partially unsaturated bicyclic heterocyclylene having 1-4 heteroatoms selected from oxygen, nitrogen, or sulfur;

$R^1$, $R^2$, $R^3$, $R^4$, $R^5$, $R^6$, $R^7$, $R^8$, and $R^9$ are independently selected from hydrogen, halogen, —CN, —C(R)=N(R), —C(O)R, —C(O)$_2$R, —C(O)N(R)$_2$, —NO$_2$, —N(R)—N(R)$_2$, —N(R)$_2$, —N(R)C(O)R, —N(R)C(O)$_2$R, —N(R)C(O)N(R)$_2$, —N(R)S(O)$_2$R, —OR, —OC(O)R, —OC(O)N(R)$_2$, —SR, —S(O)R, —S(O)$_2$R, —S(O)N(R)$_2$, —S(O)$_2$N(R)$_2$, or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

each R is independently hydrogen or an optionally substituted group selected from $C_{1-6}$ aliphatic, phenyl, 5- to 6-membered heteroaryl having 1-4 heteroatoms selected from oxygen, nitrogen, or sulfur, 3- to 7-membered saturated or partially unsaturated monocyclic carbocyclyl, and 3- to 7-membered saturated or partially unsaturated monocyclic heterocyclyl having 1-2 heteroatoms selected from oxygen, nitrogen, or sulfur;

or two R groups on the same carbon or nitrogen are taken together with their intervening atoms to form a ring selected from 3- to 7-membered saturated or partially unsaturated monocyclic ring having 0-2 heteroatoms selected from oxygen, nitrogen, or sulfur, and 5- to 6-membered heteroaryl having 1-4 heteroatoms selected from oxygen, nitrogen, or sulfur; and n is 0 or 1.

2. The compound according to claim 1, wherein when L is —(CR$_2$)$_m$NRC(O)— and m is 0 to 2, one of the following (a), (b), or (c) applies:

(a) n is 0;

(b) at least one of $R^5$, $R^6$, $R^7$, $R^8$, and $R^9$ is CN; or (c) $R^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-l-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

3. The compound according to claim 1, wherein L is selected from the group consisting of —C(R)$_2$NRC(O)-#, —C(R)$_2$C(O)NRC(R)$_2$-#, —C(R)$_2$NRC(O)C(R)$_2$-#, —C(R)$_2$NRC(R)$_2$-#, —C(R)$_2$C(R)$_2$NRC(R)$_2$-#, —C(O)NRC(R)$_2$-#, —C(R)$_2$C(O)NR-#, —NRC(O)C(R)$_2$-#, —CR$_2$C(O)NRC(R)$_2$-#, —SO$_2$NRC(R)$_2$-#, and —C(R)$_2$NRSO$_2$-#, wherein # represents the point of attachment to Het$^4$.

4. The compound according to claim 1, wherein when L is —C(R)$_2$NRC(O)-# or —C(R)$_2$C(O)NR-#, one of the following (a), (b), or (c) applies:

(a) n is 0;

(b) at least one of R$^5$, R$^6$, R$^7$, R$^8$, and R$^9$ is CN; or (c) R$^1$ is an optionally substituted saturated monocyclic heterocycle comprising 1-3 nitrogen atoms, with the proviso that the compound is not N-((7-chloroimidazo[1,5-a]pyridin-1-yl)methyl)-1-((6-cyclopropyl-8-(2-oxopyrrolidin-1-yl)imidazo[1,2-a]pyridin-2-yl)methyl)-1H-pyrazole-4-carboxamide, N-((7-chloro-8-fluoroimidazo[1,5-a]pyridin-1-yl)methyl)-1-((6-cyclopropyl-8-morpholinoimidazo[1,2-a]pyridin-2-yl)methyl)-1H-1,2,3-triazole-4-carboxamide, N-((7-chloro-8-fluoroimidazo[1,5-a]pyridin-1-yl)methyl)-1-(( 6-cyclopropyl-8-(2-oxopyrrolidin-1-yl)imidazo[1,2-a]pyridin-2-yl)methyl)-1H-1,2,3-triazole-4-carboxamide, N-((7-chloro-8-fluoroimidazo[1,5-a]pyridin-1-yl)methyl)-1-((6-cyclopropyl-8-(2-oxooxazolidin-3-yl)imidazo[1,2-a]pyridin-2-yl)methyl)-1H-1,2,3-triazole-4-carboxamide, or 4-(2-((4-(((7-chloro-8-fluoroimidazo[1,5-a]pyridin-1-yl)methyl)carbamoyl)-1H-1,2,3-triazol-1-yl)methyl)-6-cyclopropylimidazo[1,2-a]pyridin-8-yl)morpholine-2-carboxylic acid.

5. The compound according to claim 1, wherein the compound has a structure of Formula (I-a), Formula (I-b), Formula (I-c), or Formula (I-d), (I-a)

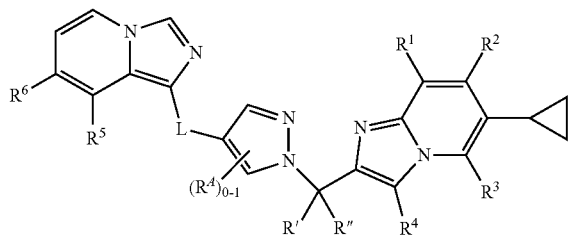

(I-b)

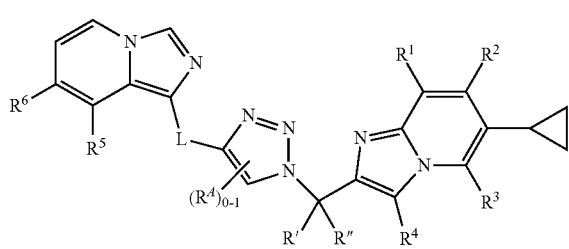

(I-c)

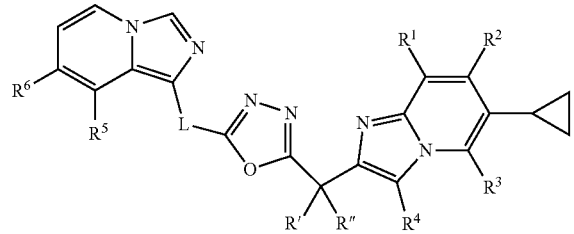

(I-d)

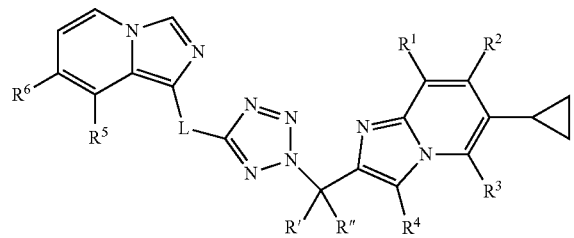

or a pharmaceutically acceptable salt thereof.

6. The compound according to claim 1, wherein the compound has a structure of Formula (II):

(II)

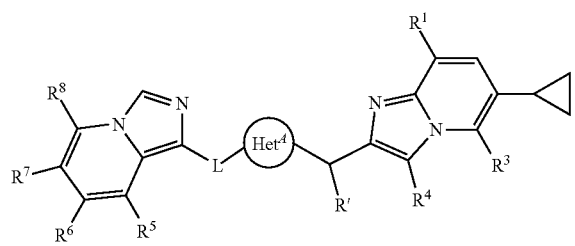

(III-a)

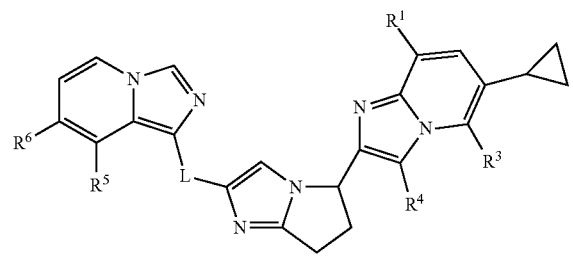

(III-b)

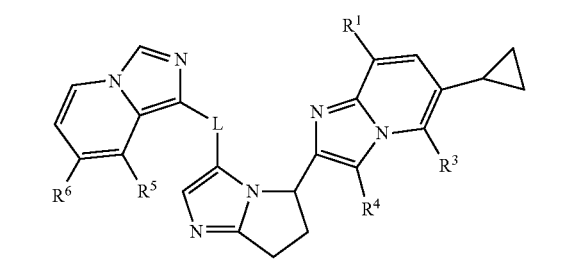

or a pharmaceutically acceptable salt thereof.

7. The compound according to claim 1, wherein the compound has a structure of Formula (II-a) or Formula (II-b):

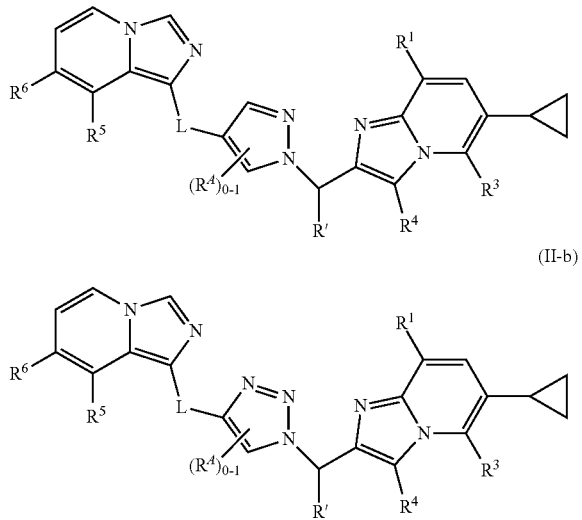

(II-a)

(II-b)

or a pharmaceutically acceptable salt thereof.

8. The compound according to claim 1, wherein R' is taken together with a monocyclic Het⁴ to form an optionally substituted fused ring and the compound has a structure of Formula (III):

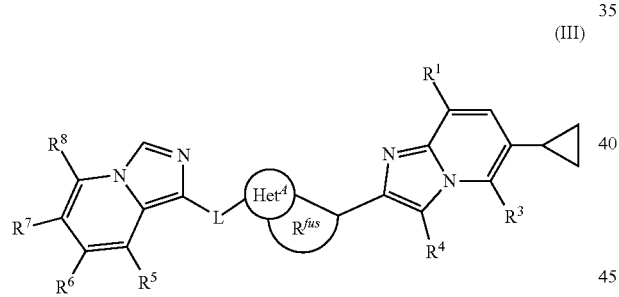

(III)

wherein $R^{fus}$ is fused with Het⁴ to form a fused 7- to 10-membered saturated or partially unsaturated bicyclic heterocyclylene having 1-4 heteroatoms selected from oxygen, nitrogen, or sulfur, or a pharmaceutically acceptable salt thereof.

9. The compound according to claim 1, wherein the compound has a structure of Formula (III-a) or Formula (III-b):

N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide (I-4), N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide (I-5), 7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-sulfonamide (I-6), 7-chloro-N-(1-(1-((6-cyclopropylimidazo[1,2-a]pyridin-2-yl)methyl)-1H-1,2,3-triazol-4-yl)ethyl)-8-fluoroimidazo[1,5-a]pyridine-1-sulfonamide (I-7), N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (I-8), N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-3-carboxamide (I-9), N-((7-cyanoimidazo[1,5-a]pyridin-1-yl)methyl)-1-((6-cyclopropylimidazo[1,2-a]pyridin-2-yl)methyl)-1H-pyrazole-4-carboxamide (I-10), 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (I-11), N-((7-chloro-8-fluoroimidazo[1,5-a]pyridin-1-yl)methyl)-1-(1-((6-cyclopropylimidazo[1,2-a]pyridin-2-yl)methyl)-1H-1,2,3-triazol-4-yl)ethan-1-amine (I-12), 2-(7-chloroimidazo[1,5-a]pyridin-1-yl)-N-(1-(((6-cyclopropylimidazo[1,2-a]pyridin-2-yl)methyl)-1H-1,2,3-triazol-4-yl)ethyl)acetamide (I-13), methyl 2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (I-14), 2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylic acid (I-15), N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (I-16), ethyl 3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (I-17a), 3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid (I-17b), 1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (I-18), 2-(7-chloroimidazo[1,5-a]pyridin-1-yl)-N-(1-(1-((6-cyclopropylimidazo[1,2-a]pyridin-2-yl)methyl)-1H-pyrazol-4-yl)-2,2,2-trifluoroethyl)acetamide (I-19), N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide (I-20);

or a pharmaceutically acceptable salt thereof.

10. The compound according to claim 1, wherein Het⁴ is a 5-membered monocyclic heteroarylene having 1-4 heteroatoms selected from oxygen, nitrogen, or sulfur, wherein Het⁴ is substituted with 0-2 R⁴ groups.

11. The compound according to claim 1, wherein Het⁴ is selected from:

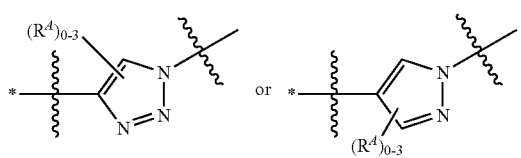

wherein * represents to point of attachment to L.

12. The compound according to claim 1, wherein a single instance of $R^A$ is $C_{1-6}$ aliphatic substituted with halogen.

13. The compound of claim 1, wherein the compound is selected from:
- 2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1),
- 1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine (I-2),
- 7-chloro-N-1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (I-3), or a pharmaceutically acceptable salt thereof.

14. A pharmaceutical composition comprising a compound of claim 1 and a pharmaceutically acceptable excipient.

15. A method of treating a plasma kallikrein-mediated disease or disorder comprising administering to a patient in need thereof a compound of claim 1, or a pharmaceutically acceptable salt thereof.

16. The method of claim 15, wherein the disease or disorder is hereditary angioedema or diabetic macular edema.

17. A method of treating hereditary angioedema or diabetic macular edema comprising administering to a patient in need thereof a compound of claim 1, or pharmaceutically acceptable salt thereof.

* * * * *

UNITED STATES PATENT AND TRADEMARK OFFICE
CERTIFICATE OF CORRECTION

PATENT NO. : 11,370,803 B2
APPLICATION NO. : 17/024189
DATED : June 28, 2022
INVENTOR(S) : Papaioannou et al.

Page 1 of 4

It is certified that error appears in the above-identified patent and that said Letters Patent is hereby corrected as shown below:

In the Claims

Column 120, Lines 44-64, please delete the structures:

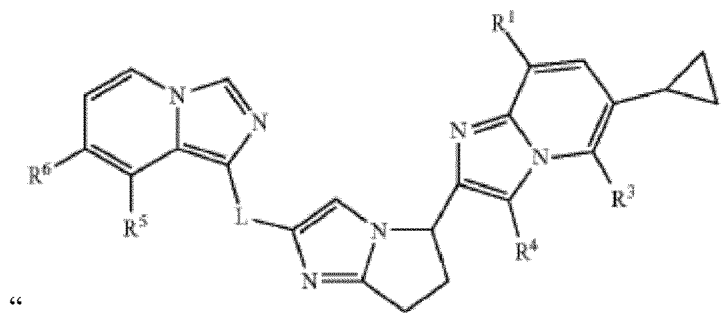

"

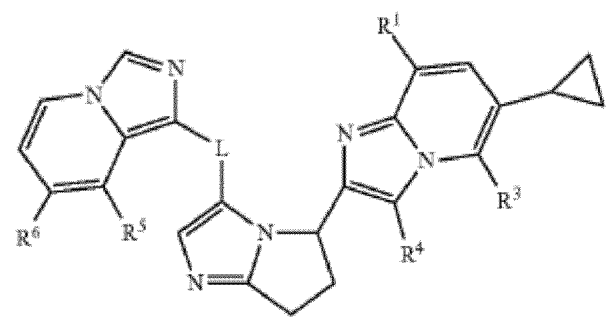

".

Column 121, Line 56 through Column 122, Line 51, please delete the text:
"N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide (I-4),
N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide (I-5), Signed and Sealed this
Twenty-second Day of November, 2022

Katherine Kelly Vidal
*Director of the United States Patent and Trademark Office*

7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-sulfonamide (I-6),
7-chloro-N-(1-(1-((6-cyclopropylimidazo[1,2-a]pyridin-2-yl)methyl)-1H-1,2,3-triazol-4-yl)ethyl)-8-fluoroimidazo[1,5-a]pyridine-1-sulfonamide (I-7),
N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (I-8),
N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-3-carboxamide (I-9),
N-((7-cyanoimidazo[1,5-a]pyridin-1-yl)methyl)-1-((6-cyclopropylimidazo[1,2-a]pyridin-2-yl)methyl)-1H-pyrazole-4-carboxamide (I-10),
1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (I-11),
N-((7-chloro-8-fluoroimidazo[1,5-a]pyridin-1-yl)methyl)-1-(1-((6-cyclopropylimidazo[1,2-a]pyridin-2-yl)methyl)-1H-1,2,3-triazol-4-yl)ethan-1-amine (I-12),
2-(7-chloroimidazo[1,5-a]pyridin-1-yl)-N-(1-(((6-cyclopropylimidazo[1,2-a]pyridin-2-yl)methyl)-1H-1,2,3-triazol-4-yl)ethyl)acetamide (I-13),
methyl 2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (I-14),
2-((4-((((7-chloro-8-fluoroimidazo[1,5-a]pyridin-1-yl)methyl)amino)methyl)-1H-1,2,3-txiazol-1-yl)methyl)-6-cyclopropylimidazo[1,2-a]pyridine-8-carboxylic acid (I-15),
N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (I-16),
ethyl 3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (I-17a),
3-(2-((4-((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid (I-17b),
1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (I-18),
2-(7-chloroimidazo[1,5-a]pyridin-1-yl)-N-(1-(1-((6-cyclopropylimidazo[1,2-a]pyridin-2-yl)methyl)-1H-pyrazol-4-yl)-2,2,2-trifluoroethyl)acetamide (I-19),
N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide (I-20);"
And insert the structures:

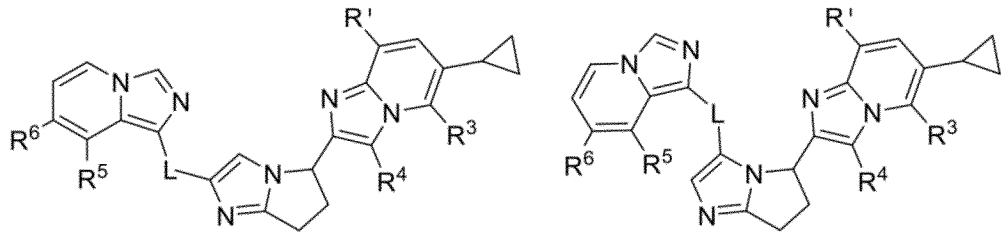

(III-a)             (III-b)--.

Column 123, Lines 6-15, please delete the text:
"2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1),

CERTIFICATE OF CORRECTION (continued)
U.S. Pat. No. 11,370,803 B2

1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine (I-2),
7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (I-3),"
And insert the text:
--2-(7-chloroimidazo[1,5-a]pyridin-1-yl)-N-((1-((6-cyclopropylimidazo[1,2-a]pyridin-2-yl)methyl)-1H-1,2,3-triazol-4-yl)methyl)acetamide (I-1),
1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)-2,2,2-trifluoroethan-1-amine (I-2),
7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-carboxamide (I-3),
N-((7-chloro-8-fluoroimidazo[1,5-a]pyridin-1-yl)methyl)-1-((6-cyclopropylimidazo[1,2-a]pyridin-2-yl)methyl)-1H-pyrazole-4-sulfonamide (I-4),
N-((7-chloro-8-fluoroimidazo[1,5-a]pyridin-1-yl)methyl)-1-((6-cyclopropylimidazo[1,2-a]pyridin-2-yl)methyl)-1H-1,2,3-triazole-4-sulfonamide (I-5),
7-chloro-N-((1-((6-cyclopropylimidazo[1,2-a]pyridin-2-yl)methyl)-1H-1,2,3-triazol-4-yl)methyl)-8-fluoroimidazo[1,5-a]pyridine-1-sulfonamide (I-6),
7-chloro-N-(1-(1-((6-cyclopropylimidazo[1,2-a]pyridin-2-yl)methyl)-1H-1,2,3-triazol-4-yl)ethyl)-8-fluoroimidazo[1,5-a]pyridine-1-sulfonamide (I-7),
N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-2-carboxamide (I-8),
N-((7-chloro-8-fluoroimidazo[1,5-a]pyridin-1-yl)methyl)-5-(6-cyclopropylimidazo[1,2-a]pyridin-2-yl)-6,7-dihydro-5H-pyrrolo[1,2-a]imidazole-3-carboxamide (I-9),
N-((7-cyanoimidazo[1,5-a]pyridin-1-yl)methyl)-1-((6-cyclopropylimidazo[1,2-a]pyridin-2-yl)methyl)-1H-pyrazole-4-carboxamide (I-10),
1-(7-chloro-8-fluoroimidazo[1,5-a]pyridin-1-yl)-N-((1-((6-cyclopropylimidazo[1,2-a]pyridin-2-yl)methyl)-1H-1,2,3-triazol-4-yl)methyl)methanamine (I-11),
N-((7-chloro-8-fluoroimidazo[1,5-a] pyridine-1-yl)methyl)-1-(1-((6-cyclopropylimidazo[1,2-a]pyridine-2-yl)methyl)-1H-1,2,3-triazol-4-yl)ethan-1-amine (I-12),
2-(7-chloroimidazo[1,5-a]pyridin-1-yl)-N-(1-(1-((6-cyclopropylimidazo[1,2-a]pyridin-2-yl)methyl)-1H-1,2,3-triazol-4-yl)ethyl)acetamide (I-13),
methyl 2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylate (I-14),
2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridine-8-carboxylic acid (I-15),
N-((7-chloro-8-fluoroimidazo[1,5-a]pyridin-1-yl)methyl)-1-(1-((6-cyclopropylimidazo[1,2-a]pyridin-2-yl)methyl)-1H-pyrazol-4-yl)-2,2,2-trifluoroethan-1-amine (I-16),
ethyl 3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoate (I-17a),
3-(2-((4-(((((7-chloro-8-fluoroimidazo[1,5-a]pyridin-1-yl)methyl)amino)methyl)-1H-1,2,3-triazol-1-yl)methyl)-6-cyclopropylimidazo[1,2-a]pyridin-8-yl)propanoic acid (I-17b),
1-(7-chloro-8-fluoroimidazo[1,5-a]pyridin-1-yl)-N-((1-((6-cyclopropyl-8-(4H-1,2,4-triazol-4-yl)imidazo[1,2-a]pyridin-2-yl)methyl)-1H-1,2,3-triazol-4-yl)methyl)methanamine (I-18),
2-(7-chloroimidazo[1,5-a]pyridin-1-yl)-N-(1-(1-((6-cyclopropylimidazo[1,2-a]pyridin-2-yl)methyl)-1H-pyrazol-4-yl)-2,2,2-trifluoroethyl)acetamide (I-19), N-((7-chloro-8-fluoroimidazo[1,5-a]pyridin-1-yl)methyl)-1-((6-cyclopropyl-8-(4-methylpiperazin-1-yl)imidazo[1,2-a]pyridin-2-yl)methyl)-1H-1,2,3-triazole-4-carboxamide (I-20);--.